US010513695B2

United States Patent
Bruno-Barcena et al.

(10) Patent No.: US 10,513,695 B2
(45) Date of Patent: *Dec. 24, 2019

(54) BETA-HEXOSYL-TRANSFERASES AND USES THEREOF

(71) Applicant: North Carolina State University, Raleigh, NC (US)

(72) Inventors: Jose M. Bruno-Barcena, Raleigh, NC (US); Suzanne Dagher, Dearborn, MI (US); Maria Azcarate-Peril, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/702,438

(22) Filed: Sep. 12, 2017

(65) Prior Publication Data

US 2018/0037873 A1    Feb. 8, 2018

Related U.S. Application Data

(63) Continuation of application No. 14/649,819, filed as application No. PCT/US2013/073870 on Dec. 9, 2013, now Pat. No. 9,783,789.

(60) Provisional application No. 61/734,742, filed on Dec. 7, 2012.

(51) Int. Cl.

| | |
|---|---|
| C12N 15/54 | (2006.01) |
| C12N 9/10 | (2006.01) |
| C12N 9/24 | (2006.01) |
| A23G 9/34 | (2006.01) |
| A23G 9/40 | (2006.01) |
| C07K 14/395 | (2006.01) |
| A23C 9/12 | (2006.01) |
| A23L 29/00 | (2016.01) |
| A23L 19/00 | (2016.01) |

(52) U.S. Cl.
CPC .......... *C12N 9/1051* (2013.01); *A23C 9/1216* (2013.01); *A23G 9/34* (2013.01); *A23G 9/40* (2013.01); *A23L 19/00* (2016.08); *A23L 29/06* (2016.08); *C07K 14/395* (2013.01); *C12N 9/2402* (2013.01); *C12Y 204/01* (2013.01); *C12Y 302/01023* (2013.01); *A23V 2002/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 4,944,952 A | 7/1990 | Kobayashi et al. | |
| 9,783,789 B2 * | 10/2017 | Bruno-Barcena | C12N 9/2402 |
| 2005/0084972 A1 * | 4/2005 | Barr | C07K 14/811 |
| | | | 435/483 |

FOREIGN PATENT DOCUMENTS

| | | |
|---|---|---|
| CN | 101864439 A | 10/2010 |
| EP | 0266177 B1 | 5/1988 |
| EP | 1283876 B1 | 2/2003 |

OTHER PUBLICATIONS

Kumagai et al., "Conversion of Starch to Ethanol in a Recombinant *Saccharomyces cerevisiae* Strain Expressing Rice α-Amylase from a Novel Pichia pastoris Alcohol Oxidase Promoter", Biotechnology (NY) 11:606-610, 1993 (Year: 1993).*
Dagher et al., "A novel N-terminal region of the membrane b-hexosyltransferase: its role in secretion of soluble protein by Pichia pastoris", Microbiology 162:23-34, 2016 (Year: 2016).*
Singaporean Third Written Opinion dated Sep. 15, 2017 from related Singaporean Application No. 11201504482V.
Second Chinese Office action dated Sep. 21, 2017 from related Chinese Application No. 201380069561.0 (including English translation).
Japanese Office action dated Nov. 7, 2017 from related Japanese Application No. 2015-545909 (including English translation).
"Sporobolomyces singularis bjIA gene for beta-galactosidase-like enzyme, complete cds", GeneBank, Jun. 28, 2008.
European Examination Report dated Jul. 12, 2017 from related European Application No. 13812374.0.
New Zealand First Examination Report dated Aug. 15, 2017 from related New Zealand Application No. 709120.
Australian Examination Report issued in counterpart AU Application No. 2013354937 dated Oct. 12, 2018 (four (4) pages).
Chinese Notification to Grant Patent Right issued in counterpart CN Application No. 201380069561.0 dated Nov. 13, 2018 with English translation (four (4) pages).
Communication pursuant to Article 94(3) EPC issued in counterpart EP Application No. 13812374.0 dated Feb. 23, 2018 (five (5) pages).
Chinese-language Office Action issued in counterpart CN Application No. 201380069561.0 dated Mar. 27, 2018, with English translation (twelve (12) pages).
New Zealand Examination Report issued in counterpart NZ Application No. 709120 dated Apr. 16, 2018 (four (4) pages).
Singapore fourth Written Opinion issued in counterpart SG Application No. 11201504482V dated Jul. 30, 2018 (eight (8) pages).
Communication under Rule 71(3) EPC issued in counterpart EP Application No. 13812374.0 dated Aug. 2, 2018 (one-hundred and twenty-nine (129) pages).
Japanese-language Office Action issued in counterpart JP Application No. 2015-545909 dated Sep. 4, 2018, with English translation (six (6) pages).

(Continued)

*Primary Examiner* — David Steadman
(74) *Attorney, Agent, or Firm* — Olive Law Group, PLLC; Nathan P. Letts

(57) ABSTRACT

This invention relates generally to the discovery of novel recombinant forms of β-hexosyl-transferases (BHT) and uses thereof to produce galacto-oligosaccharides (GOS) or as food additives.

9 Claims, 16 Drawing Sheets

Figure 3:
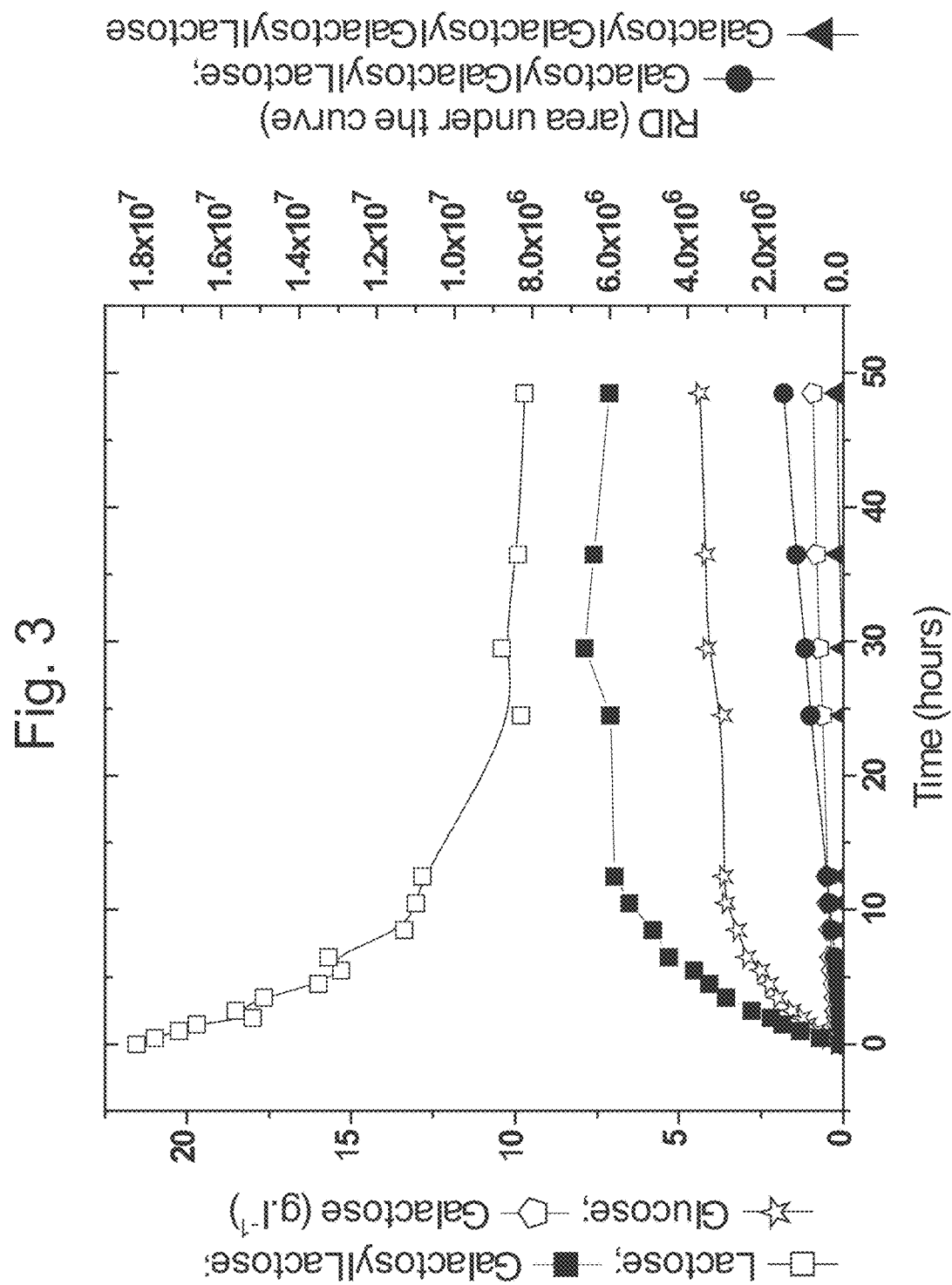

Specification includes a Sequence Listing.

(56) References Cited

OTHER PUBLICATIONS

Japanese-language Decision to Grant a Patent issued in counterpart JP Application No. 2015-545909 dated Apr. 9, 2019 (two (2) pages) with English translation.
European Communication under Rule 71(3) EPC Intention to grant issued in counterpart EP Application No. 13812374.0 dated Jan. 3, 2019.
Chinese Office action dated Jan. 22, 2017 from related Chinese Application No. 201380069561.0 (including English translation).
Cho, Youn-Jeung et al.; "Purification and biochemical properties of a galactooligosaccharide producing β-galactosidase from Bullera singularis", Biotechnology Letters; vol. 25, pp. 2107-2111 (2003).
Dagher, S.F. et al.; "Gene expression of recombinant hexosyl transferase from Sporobolomyces singularis in Pichia pastoris and in vitro production of galacto oligosaccharides", GenBank JF298281 1782 bp DNA; Sep. 8, 2012.
Dagher, S.F. et al.; "Heterologous Expression of a Bioactive-Hexosyltransferase, an Enzyme Producer of Prebiotics, from Sporobolomyces singularis" Applied and Environmental Microbiology; vol. 79(4): pp. 1241-1249 (2013).
Daly, R. et al.; "Expression of heterologous proteins in Pichia pastoris:a useful experimental tool in protein engineering and production", Journey of Molecular Recognition; vol. 18, pp. 119-138 (2005).
Yanchun et al.; "Expression, purificiation, and characterization of recombinant human keratinocyte growth factor-2 in Pichia pastoris", J. Biotechnol. vol. 132, pp. 44-48, (2007).
Damasceno, L.M. et al.; "Protein secretion in Pichia pastoris and advances in protein production" Appl Microbicl Biotechnol; vol. 93: pp. 31-39 (2012).
De Schutter et al.; "Genome sequence of the recombinant protein production host Pichia pastories" Nature Biotech. vol. 27, pp. 561-569, (2009)
European Examination Report dated Nov. 14, 2016 from related European Application No. 13812374.0.

Gosling, A. et al.; "Recent advances refining galactooligosaccharide production from lactose" Food Chemistry 121 (2), pp. 307-318 (2010).
International Search Report and Written Opinion dated Feb. 19, 2014, for International Application No. PCT/US2013/073870.
Ishikawa et al.; "Identification, cloning, and characterization of a Sporobolomyces singularis beta-galactosidase-like enzyme involved in galacto-oligosaccharide production" J Biosci Bioeng. Apr. 2005;99(4):331-9.
Torres, Durrate P.M. et al.; "Galacto-Oligosaccharides: Production, Properties,Applications, and Significance as Prebiotics", Comprehensive Reviews in Food Science and Food Safety: vol. 9: pp. 438-454 (2010).
Li et al.; "In Vivo Pharmacokinetics of Hesperdin are Affected by Treatment with Glucosidase-like BgIA Protein Isolated from Yeasts" J. Argic. Food Chem. vol. 56: pp. 5550-5557, (2008).
Park, Ah-Reum et al.; "Galacto-oligosaccharide production using microbial β-galactosidase: current state and perspectives" Appl Microbiol Biotechnol; vol. 85, pp. 1279-1286 (2010).
Rastall, R.A. et al.; "Prebiotics and synbiotics: towards the next generation" Current Opinion in Biotechnology; vol. 13(5), pp. 490-496 (2002).
Sang, Helen "Propects from transgenesis in the chick" Mechanisms of Development, vol. 121, pp. 1179-1186, (2004).
Singaporean Second Written Opinion dated Feb. 14, 2014 from related Singaporean Application No. 11201504482V.
Skory, C.D. et al.; "Expression and secretion of the Candida wickerhamii extracellular b-glucosidase gene, bgIB, in *Saccharomyces cerevisiae*" Curr Genet; vol. 30: pp. 417-422 (1996).
Terpe, K. "Overview of tag protein fusions: from molecular and biochemical fundamentals to commercial systems" Appl. Microbiol. Biotechnol. vol. 60 pp. 523-533, (2003).
Singaporean First Written Opinion dated Apr. 25, 2016 from related Singaporean Application No. 11201504482V.
Australian Notice of Acceptance issued in counterpart AU Application No. 201334937 dated Sep. 9, 2019.

\* cited by examiner

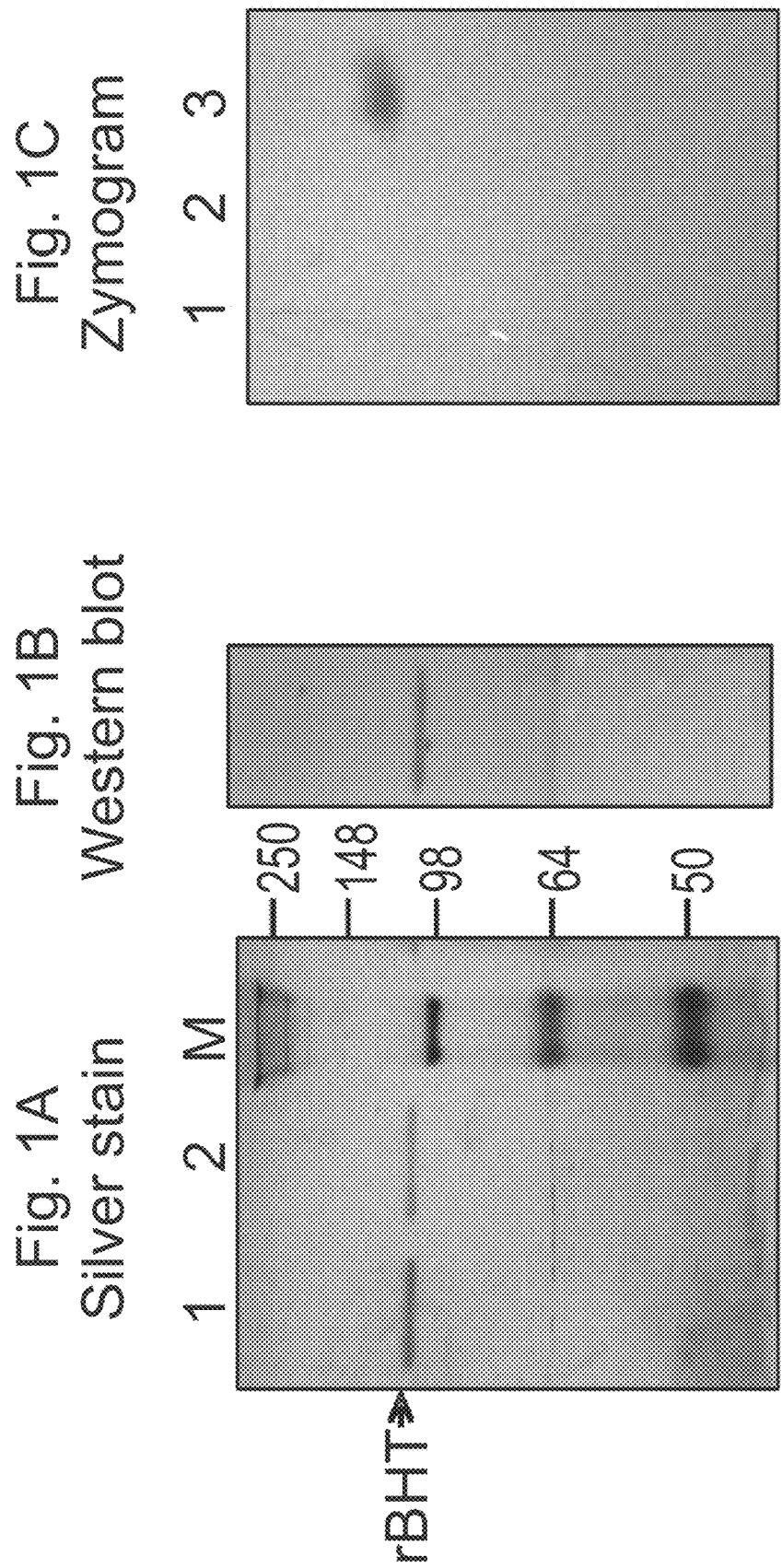

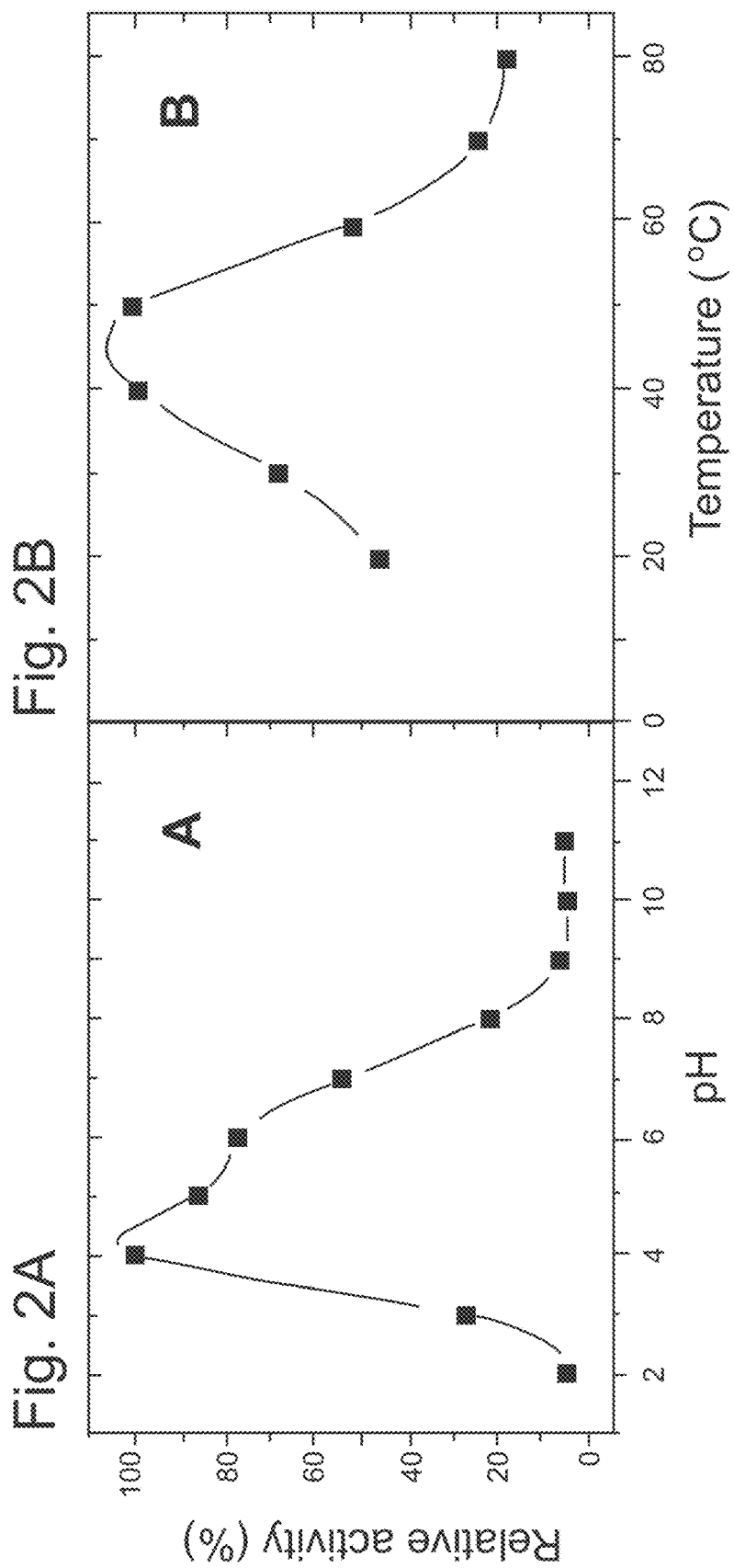

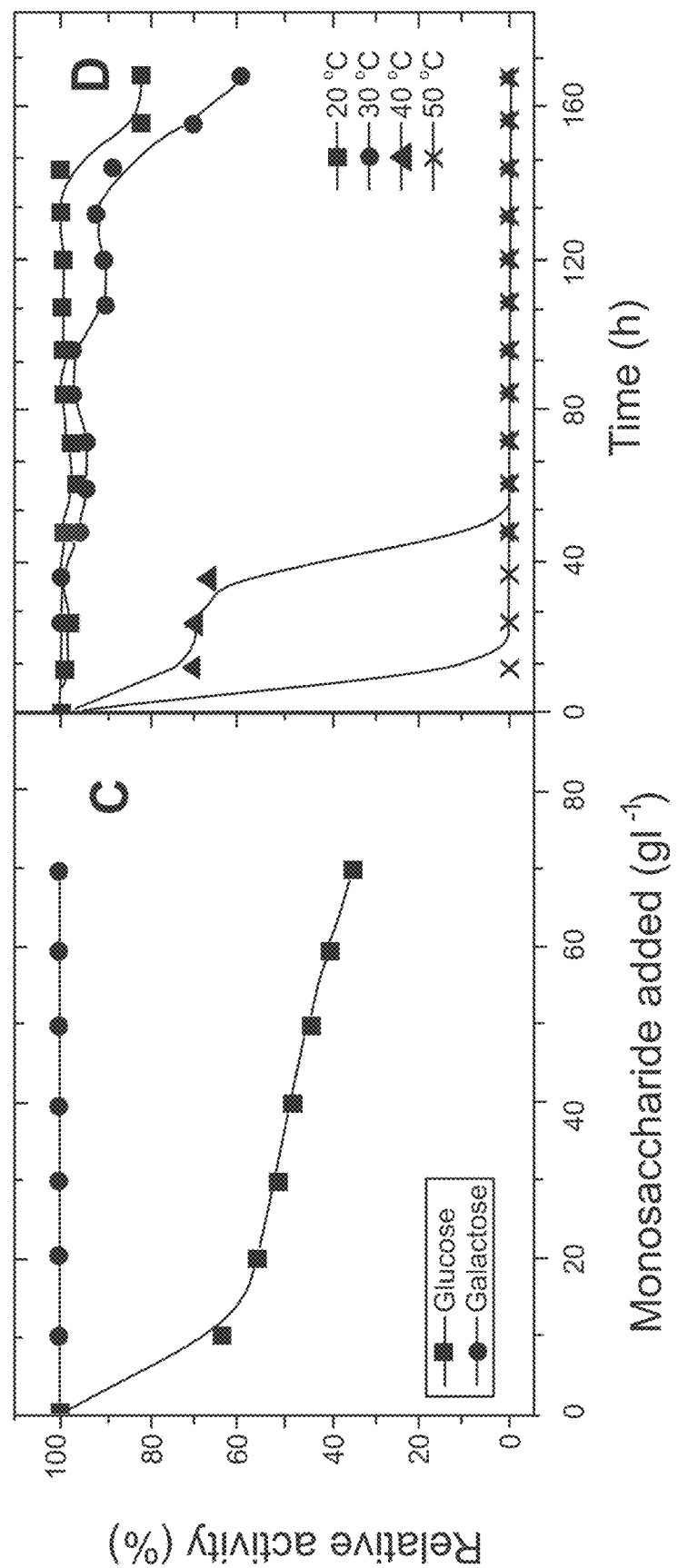

| FP # | Name | Protein Construct | | | | | |
|---|---|---|---|---|---|---|---|
| 1 | aMF-6XHIS-TEV(Q/M)-rBHT | aMF— | 6XHIS—TEV— | 1-22 | 23-110 | 111-394 | —COOH |
| 2 | aMF-6XHIS-TEV(Q/M)-aMF-rBHT-6XHIS | aMF— | 6XHIS—TEV— | 1-22 | 23-110 | 111-394 | —6XHIS—COOH |
| 3 | aMF-rBHT-6XHIS | | aMF— | 1-22 | 23-110 | 111-394 | —6XHIS—COOH |
| 4 | aMF-rBHT | | aMF— | 1-22 | 23-110 | 111-394 | —COOH |
| 5 | aMF-rBHT(?1-22) - 6XHIS | | | aMF— | 23-110 | 111-394 | —6XHIS—COOH |
| 6 | aMF-rBHT(?1-22) | | | aMF— | 23-110 | 111-394 | —COOH |
| 7 | rBHT-6XHIS | | | 1-22 | 23-110 | 111-394 | —6XHIS—COOH |
| 8 | rBHT(?1-22)-6XHIS | | | | 23-110 | 111-394 | —6XHIS—COOH |
| 9 | aMF-rBHT(?1-110)-6XHIS | | | aMF— | | 111-394 | —6XHIS—COOH |

(A) Kyte and Doolittle hydropathy plot for BHT. (B) Graphic representation of the constructs created. Contact codes: *Ala* helix contact, Xxx membrane contact, Xxx cleavage.

Fig. 6B

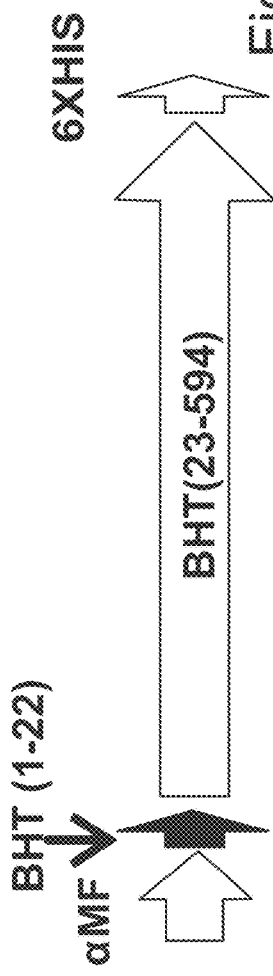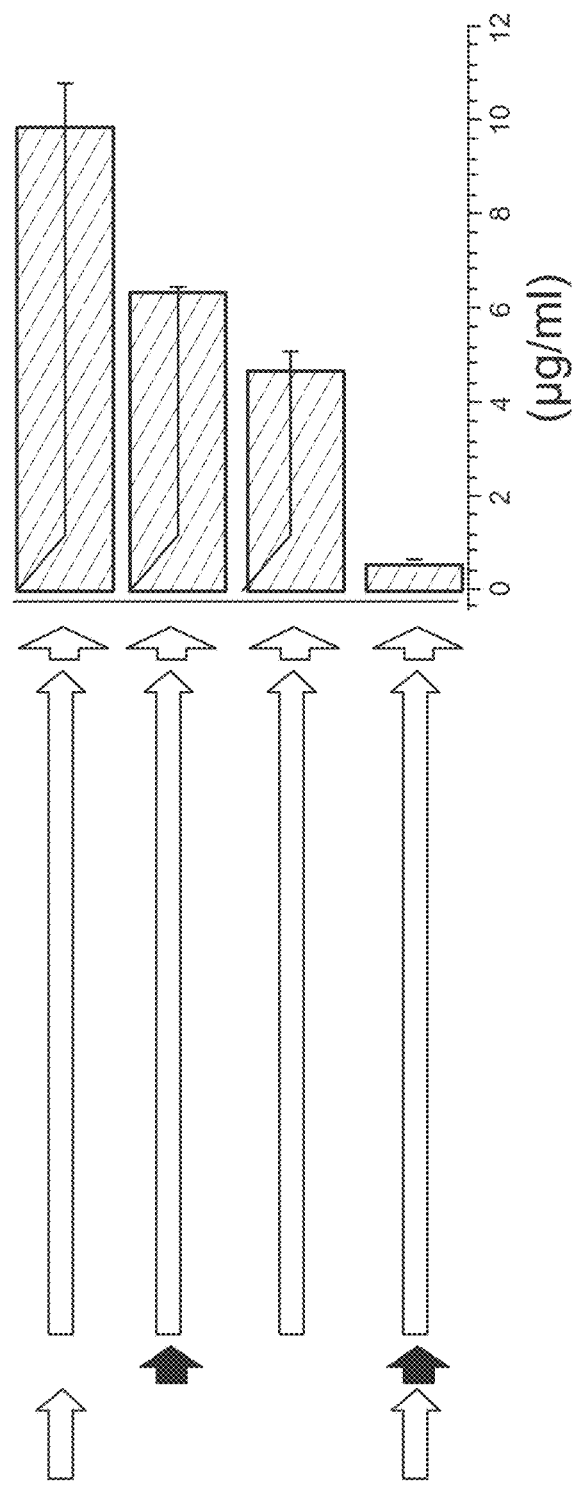

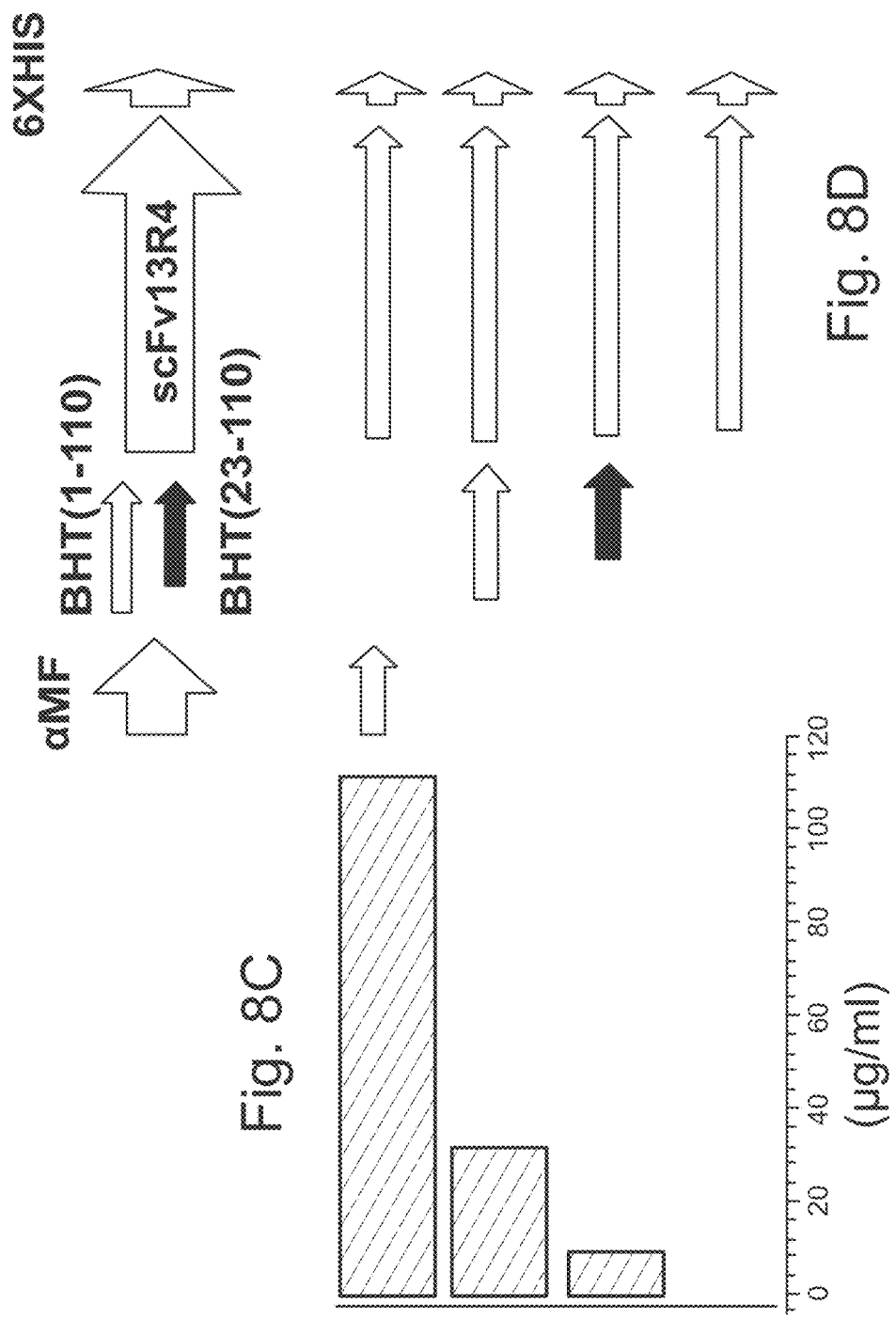

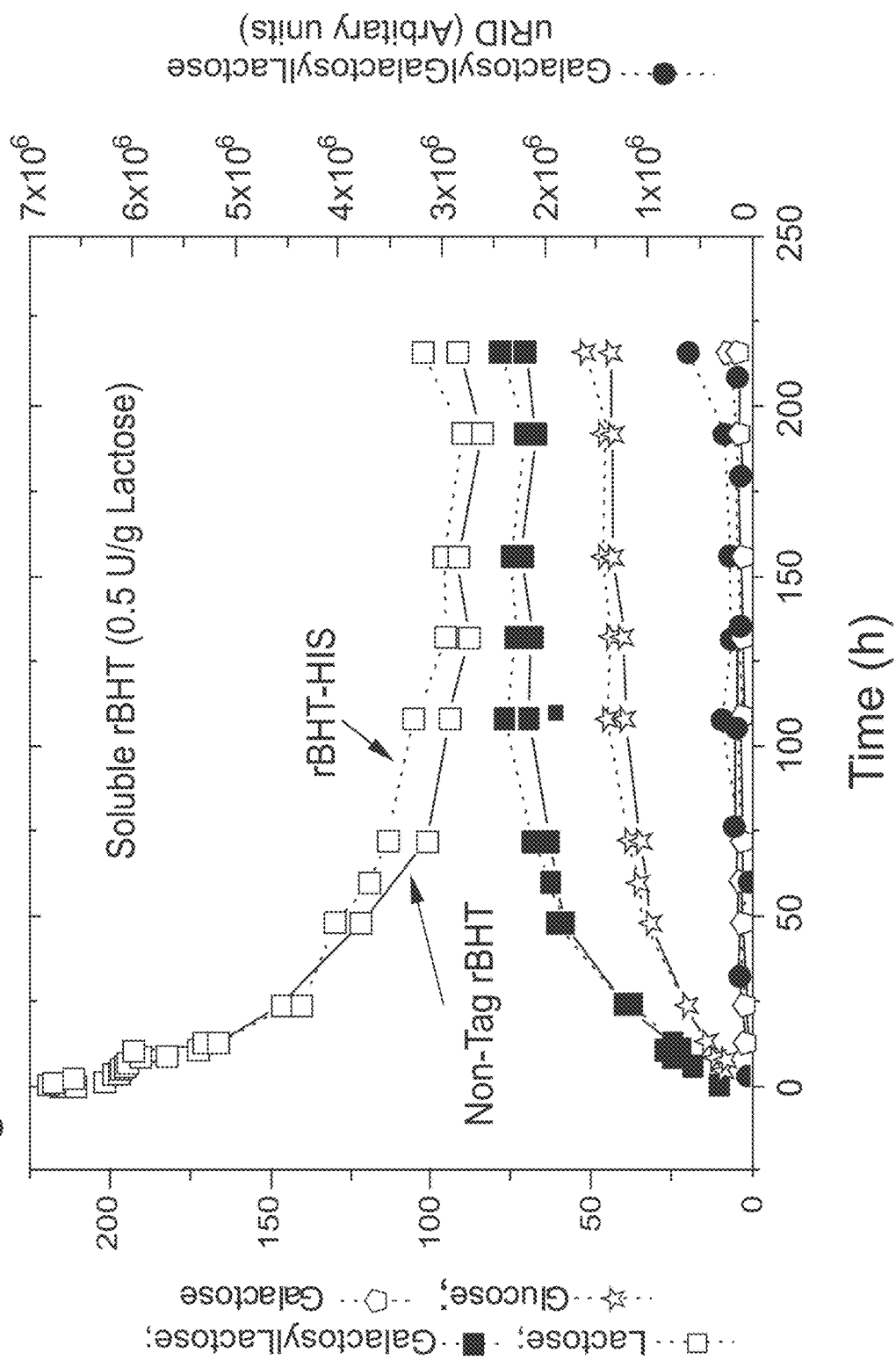

BETA-HEXOSYL-TRANSFERASES AND USES THEREOF

CROSS REFERENCE TO RELATED APPLICATIONS

This application is a continuation application of U.S. Ser. No. 14/649,819, filed Jun. 4, 2015, which is a § 371 U.S. National Stage of International Application PCT/US2013/073870, filed Dec. 9, 2013, which claims the benefit of U.S. Provisional Appn. No. 61/734,742 filed Dec. 7, 2012, Bruno-Barcena et al., entitled "Beta-hexosyl-transferases and Uses Thereof" which are hereby incorporated by reference in their entireties.

1. FIELD OF THE INVENTION

This invention relates generally to the discovery of novel recombinant forms of β-hexosyl-transferases (BHT) and uses thereof to produce galacto-oligosaccharides (GOS).

2. BACKGROUND OF THE INVENTION 2.1. Introduction

The complex interaction between diet, normal intestinal microbiota, and wellbeing has encouraged the development of strategies to promote the selective proliferation of beneficial microorganisms into the gastrointestinal track of humans. Probiotics are microorganisms that positively affect human health with attributed powerful antipathogenic and anti-inflammatory properties (27) (Table 1).

TABLE 1

Health Benefits of Probiotics

| Intestinal | Immunity | Reduce disease risk |
|---|---|---|
| Helicobacter pylori infection | Reducing allergic reactions | Coronary heart disease High blood pressure |
| Lactose intolerance | Reducing opportunity of infection by pathogens | Upper respiratory tract infections |
| Irritable bowel syndrome | | Urinary tract disease |
| Ulcerative colitis | | Reduced cholesterol and lipids |
| Crohn'sdisease | | |
| Diarrhea | | |
| Constipation | | Aid in prevention of colon cancer |
| Stimulate mineral adsorption | | |

Also, years of probiotic research indicate that a selective modification of the intestinal microbiota and its associated biochemical activities can be promoted by selective prebiotics. Osborn D A, Sinn J K. Prebiotics in infants for prevention of allergic disease and food hypersensitivity. Cochrane Database of Systematic Reviews 2007. Prebiotics are non-digestible oligosaccharides (NDOs) that have a dual ability. First they reduce the intestinal colonizing efficiency of harmful bacteria and second they act as selective substrate to promote the growth and thereby increasing the number of specific probiotic bacteria.

In addition, an increasing number of studies have shown that probiotics work best when combined with prebiotics. Mayer et al. 2003 Research for creation of functional foods with Bifidobacteria. *Acta Alimentaria* 32 27-39. This combined form of delivery is known as a synbiotic. Gibson G R, Roberfroid M B. 1995 Dietary Modulation of the Human Colonic Microbiota—Introducing the Concept of Prebiotics. *Journal of Nutrition* 125:1401-12.

Galacto-oligosaccharides (GOS) are considered one of the preferred choices of prebiotics and in the gastrointestinal tract, GOS are resistant to enzymes and transit though the small intestine without being digested, but in the large intestine GOS are fermented and can activate growth of intestinal bifidobacteria such as *Lactobacillus acidophilus* and *L. casei*, hence acting as a prebiotic(26, 27, 37).

GOS are non-digestible oligosaccharides owing to the conformation of their anomeric C atom ($C_1$ or $C_2$), which allows their glycosidic bonds to evade hydrolysis by digestive enzymes in the stomach or small intestine. Free oligosaccharides are found in the milk of all placental mammals, providing a natural example of prebiotic feeding during infancy. According to the latest definition by the International Scientific Association for Probiotics and Prebiotics (ISAPP) "a dietary prebiotic is a selectively fermented ingredient that results in specific changes in the composition and/or activity of the gastrointestinal microbiota, thus conferring benefit(s) upon host health" (30). The composition of human milk oligosaccharides (HMO) is very complex, which makes it unlikely to find alternative sources containing oligosaccharides of analogous composition. Improved colonic health among breastfed infants has been attributed to the presence of GOS in the mother's milk (2). In fact, infant formula with added GOS replicated the bifidogenic effect of the human milk with respect to metabolic activity of colonic microbiota and bacterial numbers (6,21). Among non-milk oligosaccharides, GOS are of special interest as their structure resembles the core molecules of HMOs (3). However, GOS concentration and composition vary with the method and the enzyme utilized for their generation, which in turn may influence their prebiotic effects and the proliferation of colonic probiotic strains (29). Traditionally, GOS have been produced using β-galactosidases from mesophilic microorganisms. Mesophilic β-galactosidases require high initial concentrations of lactose to drive the reaction away from lactose hydrolysis and towards GOS synthesis. Since lactose is more soluble at elevated temperatures, thermostable β-galactosidases exhibiting high initial velocities and increased half-lives have been utilized to reach a favorable equilibrium for the transgalactosylation reaction (27,37). However, competitive inhibition by glucose and/or galactose is another obstacle that remains which may be overcome by incorporating cells in the reaction (16,20,25,27,35).

The basidiomycete yeast *Sporobolomyces singularis* (formerly *Bullera singularis*) cannot utilize galactose to grow but proliferates on lactose due to the activity of its β-hexosyl-transferase (BHT, EC 3.2.1.21). Studies have shown that the BHT has transgalactosylation activity even at low lactose concentrations and very limited lactose hydrolysis. In addition, the enzyme does not appear to be inhibited by lactose concentrations above 20% and has the potential for conversions into GOS close the maximum theoretical of 75% (1,9,10,28). Unlike β-galactosidases, the BHT from *S. singularis* simultaneously carries out glycosyl-hydrolase and β-hexosyl-transferase activities, converting lactose to GOS without extracellular accumulation of galactose. Two molecules of lactose are required during the transgalactosylation event: one molecule is hydrolyzed and the second acts as galactose acceptor, generating the trisaccharide galactosyl-lactose (β-D-Gal(1-4)-β-D-Gal(1-4)-β-D-Glc) and residual glucose. Galactosyl-lactose can also act as acceptor of a new galactose to generate the tetrasaccharide galactosylgalactosyl-lactose (β-D-Gal(1-4)-β-D-Gal(1-4)-β-D-Gal(1-4)-β-D-Glc), and similarly for the tetrasaccharide and subsequent products. The tri, tetra, and penta saccharides accumulating in *S. singularis* have been collectively designated GOS (9,10).

For practical interests, a recombinant secreted BHT could have several advantages over the native enzyme, including improved large scale production and purification. Currently, purification of active enzyme from *S. singularis* requires cell lysis followed by multiple chromatography steps (1,4,16). Previous attempts to express recombinant β-hexosyl-transferase in *E. coli* BL21 have resulted in high levels of production, but the enzyme was inactive and insoluble (16).

3. SUMMARY OF THE INVENTION

In particular non-limiting embodiments, the present invention provides an isolated DNA coding for a recombinant β-hexosyl-transferase (rBHT) protein having the amino acid sequence set forth in SEQ ID NO. 2, 4, 6, 8, 10, 12, 14, 16, 18 or 20. The isolated DNA coding for the recombinant β-hexosyl-transferase (rBHT) protein may have the nucleic acid sequence set forth in SEQ ID NO. 1, 3, 5, 7, 9, 11, 13, 15, 17 or 19.

The invention also provides, an enzymatically active recombinant β-hexosyl-transferase (rBHT) protein wherein the protein has the amino acid sequence set forth in SEQ ID NO. 2, 4, 6, 8, 10, 12, 14, 16, 18 or 20. The rBHT protein may be membrane bound or may be a soluble enzyme.

The enzymatically active rBHT producing GOS may, or may not be, inhibited by galactose.

The invention also provides a method for producing enzymatically active recombinant β-hexosyl-transferase (rBHT) protein in a eukaryotic host cell which comprises transforming the eukaryotic host cell with a plasmid under the control of a suitable promotor wherein the plasmid contains an isolated DNA coding for an rBHT protein having the amino acid sequence set forth in SEQ ID NO. 2, 4, 6, 8, 10, 12, 14, 16, 18 or 20.

In some embodiments, the isolated DNA is linked to a DNA coding for a signal peptide. The signal peptide may be an *S. cerevisiae* α-factor signal peptide and the suitable promotor may be an alcohol oxidase promotor.

In some embodiments, the enzymatically active rBHT protein has a specific activity of about 8 U·mg$^{-1}$ at 20° C.

The eukaryotic host cell may be a yeast cell such as *Pichia pastoris*.

The invention also provides method for producing galacto-oligosaccharides (GOS) which comprises reacting lactose with an enzymatically active recombinant β-hexosyl-transferase (rBHT) protein having the amino acid sequence set forth in SEQ ID NO. 2, 4, 6, 8, 10, 12, 14, 16, 18 or 20 under suitable conditions so as to produce GOS.

The enzymatically active rBHT protein may be immobilized on a solid support. The solid support may be in a batch or continuous stirred-tank reactor, a packed-bed reactor, or an ultrafiltration membrane reactor. Alternatively, the enzymatically active rBHT protein may be used directly in a batch or continuous stirred-tank reactor, a packed-bed reactor, or an ultrafiltration membrane reactor. The method may further comprise a glucose removal system to avoid competitive glucose inhibition such as a generally recognized as safe (GRAS) organism. The glucose removal system may be used simultaneously with the enzymatically active rBHT protein.

The invention is also directed to a modified lactose-containing foodstuff or food byproduct comprising a recombinant β-hexosyl-transferase (rBHT) protein having the amino acid sequence set forth in SEQ ID NO. 2, 4, 6, 8, 10, 12, 14, 16, 18 or 20. The lactose-containing foodstuff or food byproduct may be a dairy product or byproduct such as whey. In some embodiments, the foodstuff or food byproduct is a baby dessert, a baby juice, a baby snack, a baby yoghurt drink, an energy drink, a fitness water or thirst quencher, a frozen dairy dessert, a fruit drink (vitamin/mineral fortified), a fruit pie filling, a fruit preparation, an infant formula, an infant meal replacement drink, a jelly jam, a meal replacement drink, a milk, a milk-based drink, a milk substitute, a syrup flavoring for milk, a yoghurt, or a whey.

4. BRIEF DESCRIPTION OF THE FIGURES

FIG. 1A-1C. Gel electrophoresis of purified rBHT expressed in *P. pastoris*. (1A) SDS-PAGE of purified rBHT silver stained: Lane 1, 0.5 μg rBHT; lane 2, 0.1 μg rBHT. (1B) Western blot analysis with anti-rBHT antiserum. Lane M indicates the molecular masses (kDa) of the marker proteins are shown to the right of Panel A. (1C) Zymogram of rBHT. Lane 1, purified rBHT-6xHIS expressed in *E. coli* BLR cultures; Lane 2, broth from untransformed methanol induced GS115; Lane 3, broth from methanol induced recombinant GS115/rBHT. Activity was visualized by the formation of a blue precipitate resulting from enzymatic cleavage of X-GAL.

FIG. 2A-2D. rBHT relative activity dependence on (2A) pH. (2B) Temperatures from 20° C. to 80° C. (2C) Concentration of galactose (solid circle) and glucose (solid square). (2D) Thermal stability at 20° C. to 50° C. Samples were removed every 12 h and assayed for activity at 20° C. Enzyme activity assays were conducted in 50 mM sodium phosphate (pH 5.0) containing 1.3 mM ONP-Glu at 20° C., except for (A) which used sodium phosphate (pH 5-11) or citrate (pH 2-5) buffers. Enzyme activities were calculated relative to the value taken at time zero (100%). The initial concentration of tested enzyme was 0.2 U·ml$^{-1}$ assayed at 20° C. ($K_m$=–0.37 mM and $V_{max}$=0.09 mM·min$^{-1}$). Data represents the means of two experiments with a reliability of ±5%.

FIG. 3. Synthesis of galactosyl-lactose from lactose (2%) using partially purified rBHT (0.5 U·g$^{-1}$ lactose) in 5 mM sodium phosphate buffer pH 5.0 incubated at 42° C. Concentrations of lactose, glucose, galactose and galactosyl-lactose are shown in g·l$^{-1}$. The residual non-quantified GOS species are shown as signal intensity readings from the refractive-index detector. Data represents the means of two experiments with a reliability of ±5%.

Figure 4A:
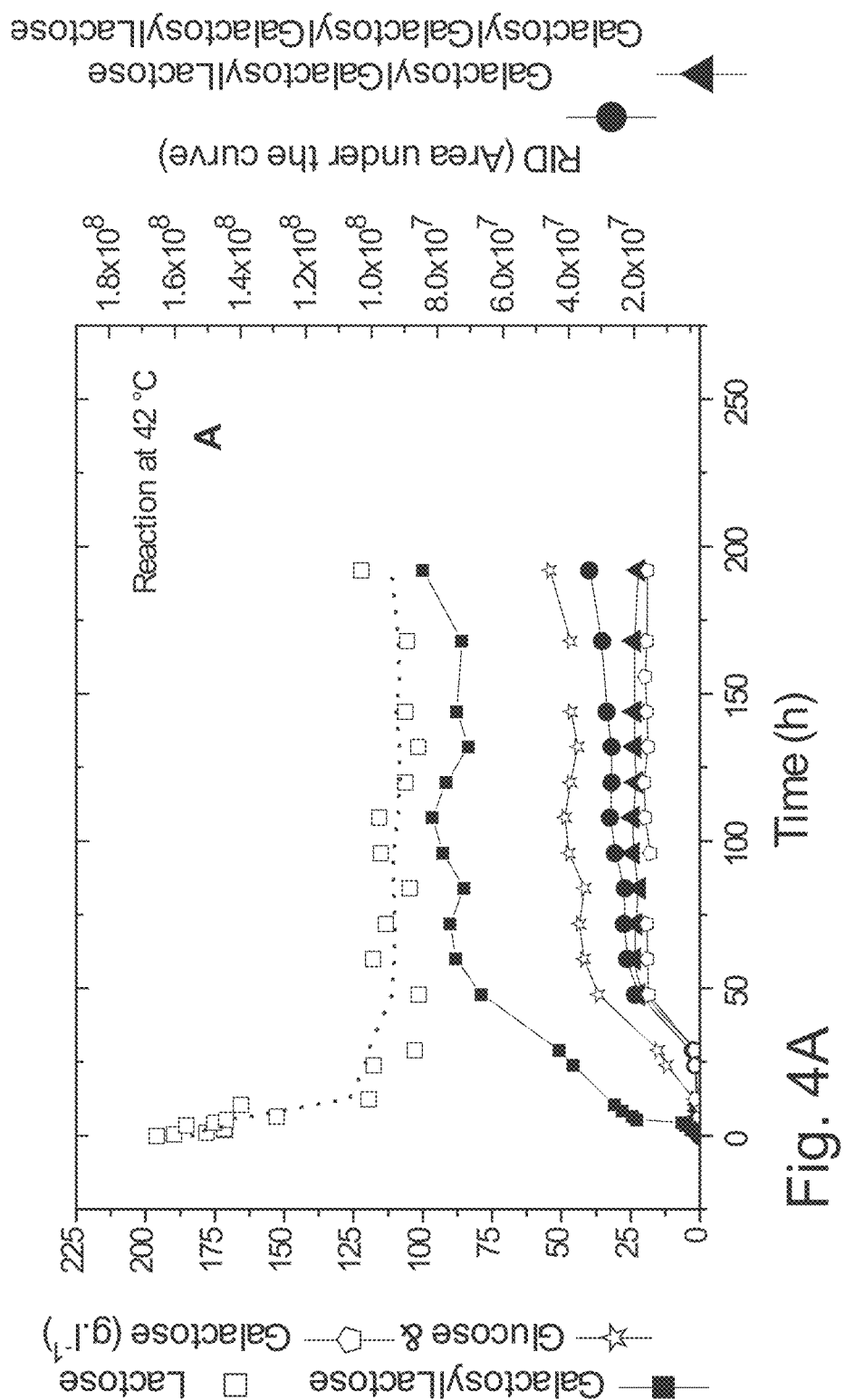
Figure 4B:
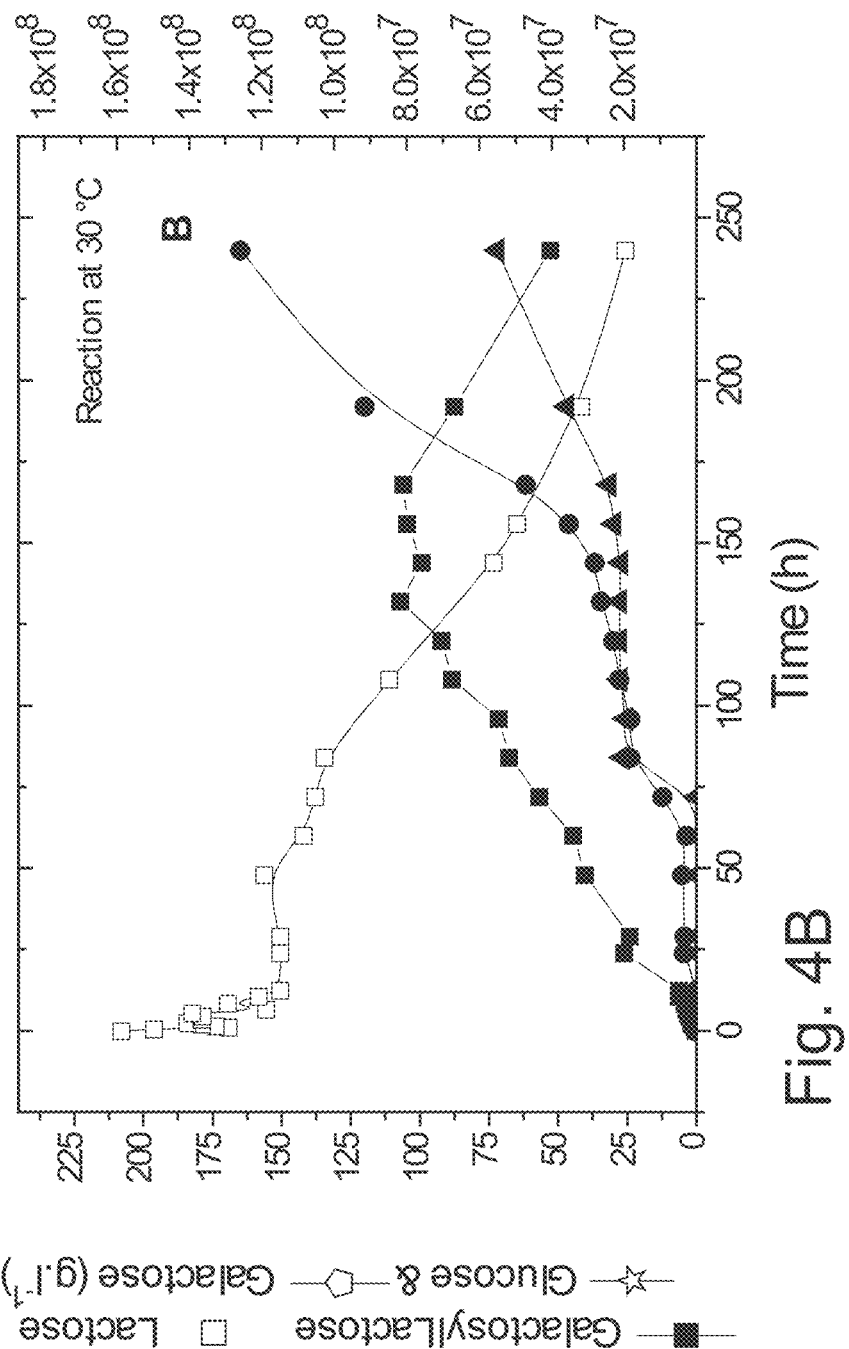

FIG. 4A-4B. Synthesis of galacto-oligosaccharides from lactose (20%) using *P. pastoris* resting cells (harboring membrane-bound rBHT at 0.5 U·g$^{-1}$ lactose) in 5 mM sodium phosphate buffer pH 5.0 incubated at 42° C. (4A) or 30° C. (4B). Concentrations of lactose, glucose, galactose and galactosyl-lactose are shown in g·l$^{-1}$. The residual non-quantified GOS species are shown as signal intensity readings from the refractive-index detector. Data represents the means of two experiments with a reliability of ±5%.

Figure 5:
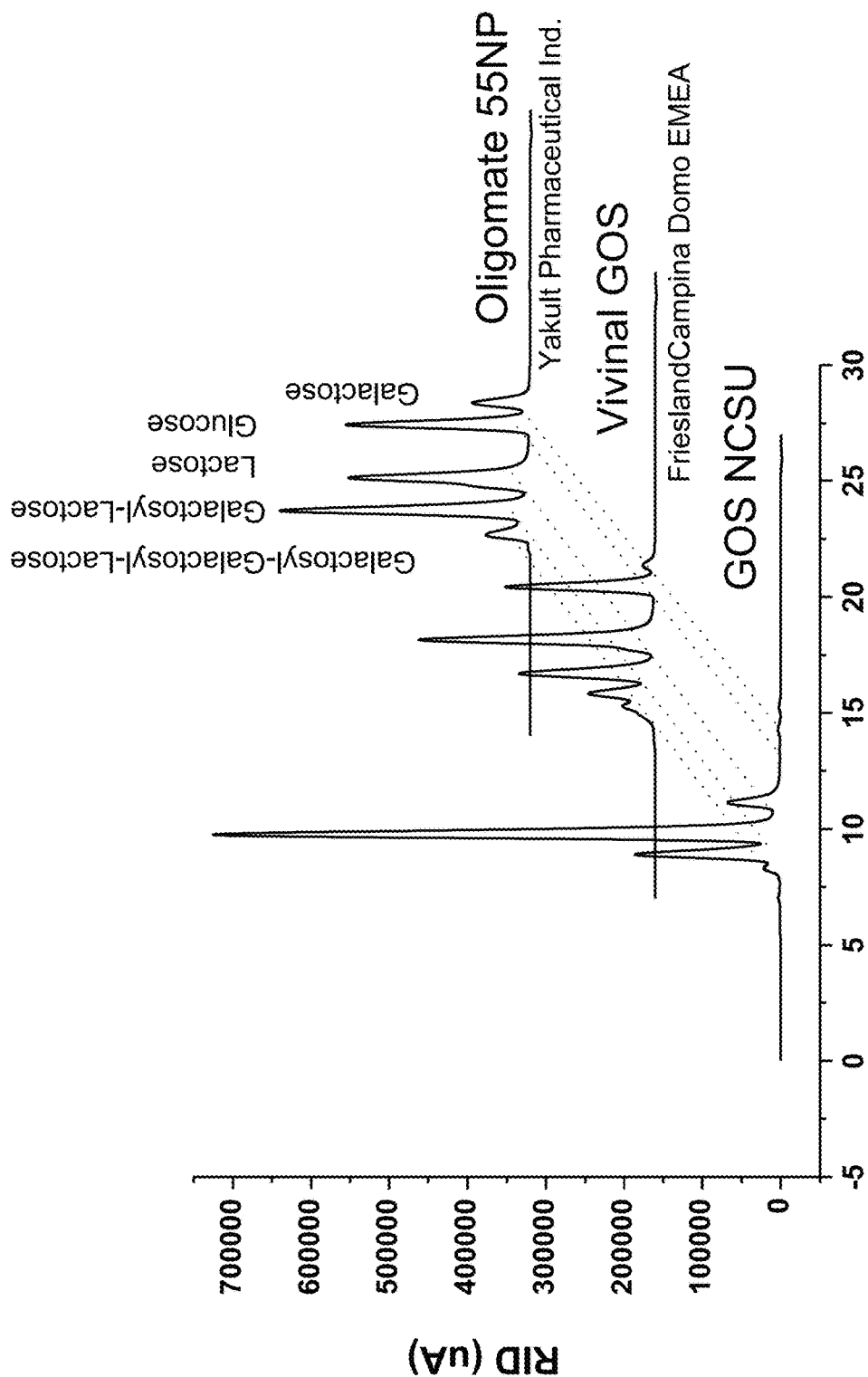

FIG. 5. Shows a comparison of the enzymatic activities and the sugars including GOS produced by the rBHT described herein (GOS NCSU) and two commercially available enzymes Vivinal GOS and Oligomate 55NP from Yakalt Pharmaceuticals, Inc. at 30° C. See the procedure in Section 6.3.

Figure 6A:
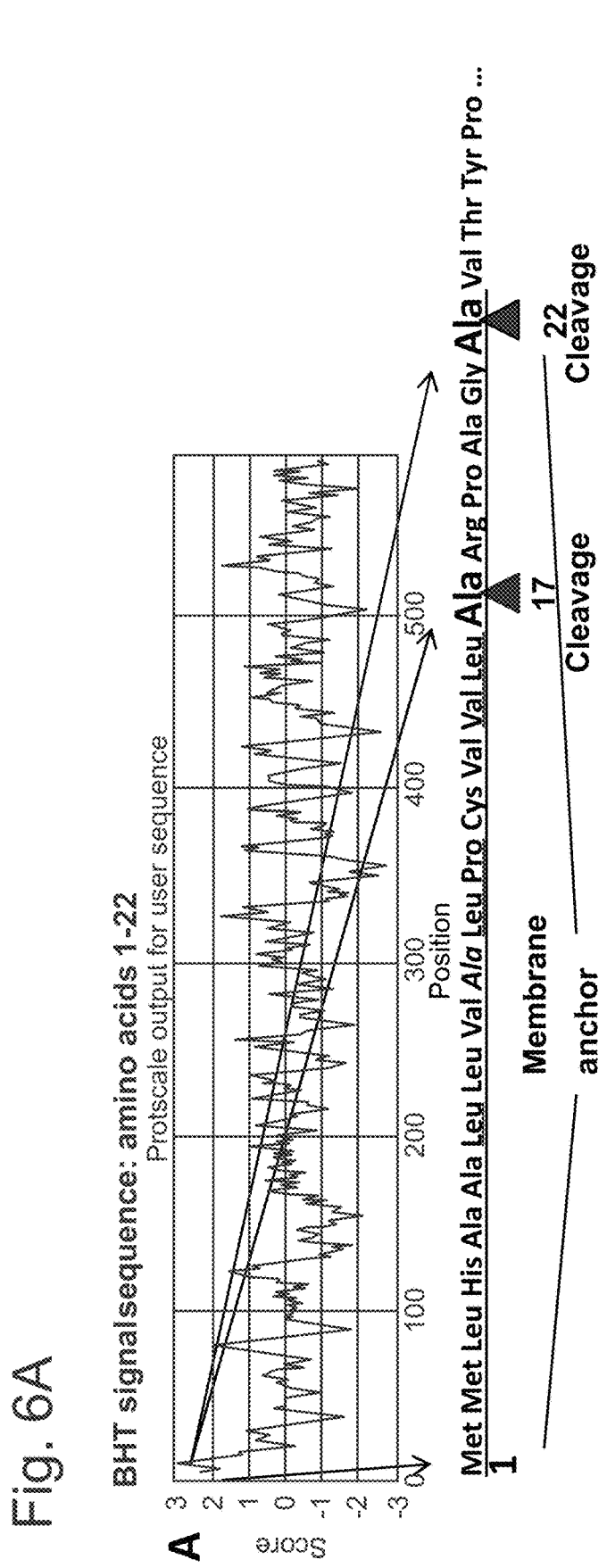

FIG. 6A-6B. Kyte and Doolittle hydropathy plot for BHT. The amino acid sequence for the predicted membrane anchor/signal sequence has been amplified (residues 1-26 of SEQ ID NO:2). The transmembrane region prediction algorithm (www.ch.embnet.org/software/TMPRED_form DOT html) also forecasted a stretch of hydrophobic residues 1-17 in BHT typical for integral membrane spanning proteins and the SignalP algorithm (www.cbs.dtu.dk/services/SignalP/) predicted a possible signal sequence for the same residues and possible cleavage site between residues 17 and 18 and between 22 and 23. The signal sequence was retained in constructions 1, 2, 3, 4 and 7 to serve as a natural membrane anchor.

Figure 7A:
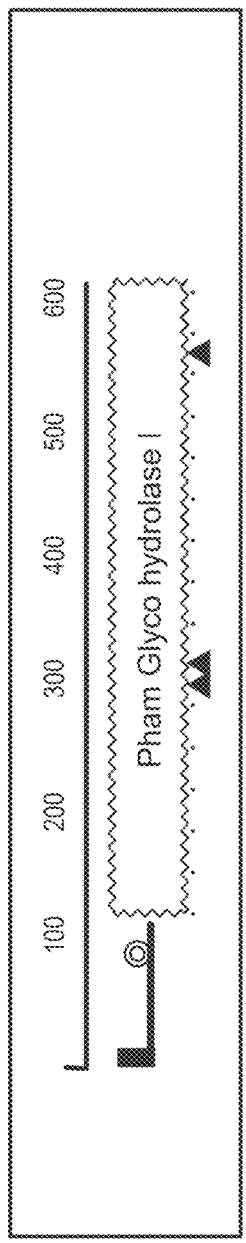
Figure 7B:
Figure 7C:
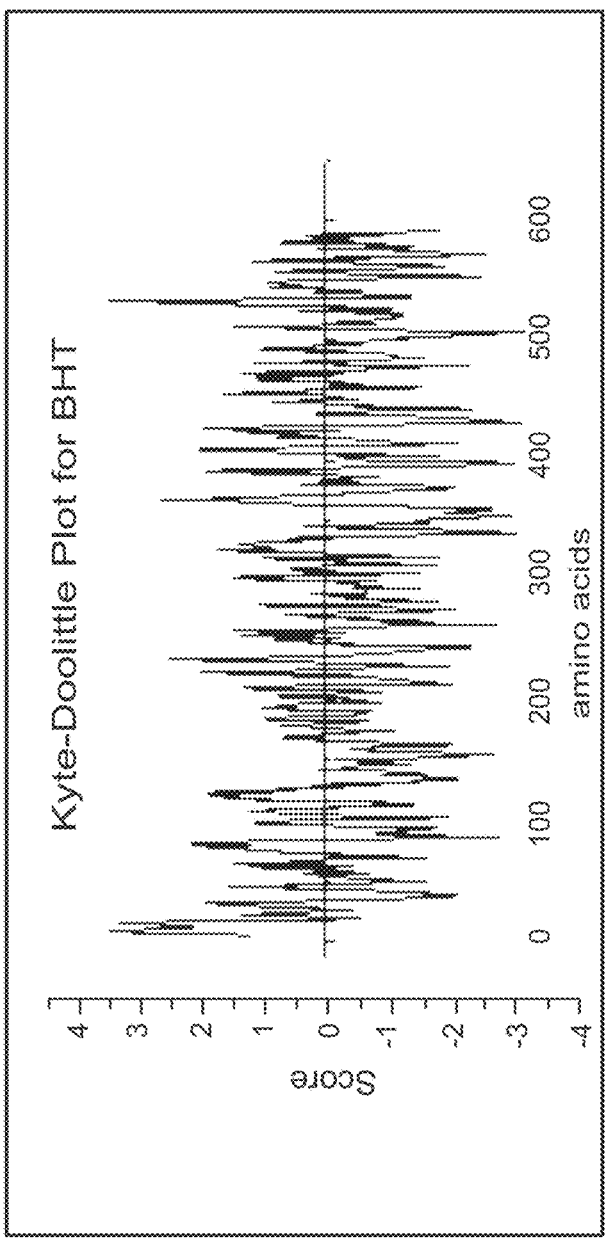

FIG. 7A-7C. Sequence analysis of BHT. (7A) Schematic representation of the BHT polypeptide from *S. singularis* determined by the web-based SMART program (smart.embl-heidelberg.de). The leader peptide represented by a solid square was determined by the SignalP program. Segment of low compositional complexity represented by a solid circle was determined by the SEG program (mendel.imp.ac.at/METHODS/seg.server DOT html). Hits only found by BLAST are indicated by the Glyco hydrolase domain. Solid triangles indicate the positions of the three putative N-glycosylation sites determined by NetNGlyc 1.0 (www.cbs.dtu.dk/services/NetNGlyc/). (7B) Schematic representation of the leader peptide calculated by the RHYTHM transmembrane prediction method. The amino acid sequence for the predicted membrane anchor peptide has been amplified (residues 1-23 of SEQ ID NO:2). Membrane contact amino acids are in large bold type and the helix contact amino acid is in large type and underlined. Also indicted are the positions of predicted cytoplasmic and extracellular regions. Arrows indicate possible cleavage sites. (7C) Hydropathy plot. The plot was generated using Kyte-Doolittle method of calculating hydrophilicity over a window length of nine amino acids. The number of amino acids is shown below the X-axis. Zero on the Y-axis separates hydrophobic and hydrophilic amino acids.

FIG. 8A-8D. Concentration of secreted protein by each recombinant *P. pastoris* strain. Graphic representations of recombinant strains containing rBht and scFv13R4 are shown to the left (8A) and right (8D) of the plots, respectively. (8B) rBHT-HIS secreted. (8C) scFv13R4-HIS secreted. The values of secreted protein were normalized for $OD_{600}$ and represented the mean±SE. Secreted proteins were analyzed from the following recombinant strains: (8A and 8B) row 1, GS115::αMF-rBht$_{(23-594)}$-HIS; row 2, GS115::rBht-HIS; row 3, GS115::rBht$_{(23-594)}$-HIS; row 4, GS115::αMF-rBht-HIS. (8C and 8D) row 1, GS115::αMF-scFv13R4-HIS; row 2, GS115::rBht$_{(1-110)}$-scFv13R4-HIS; row 3, GS115::rBht$_{(23-110)}$-scFv13R4-HIS; row 4, GS115::scFv13R4-HIS.

Figure 9A:
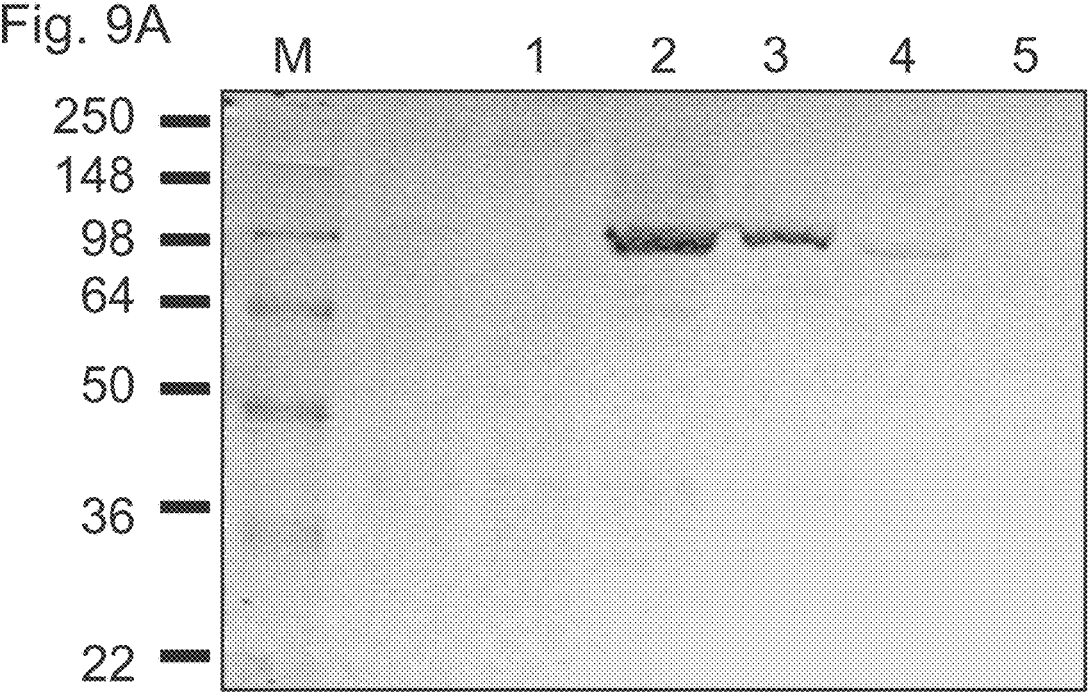
Figure 9B:
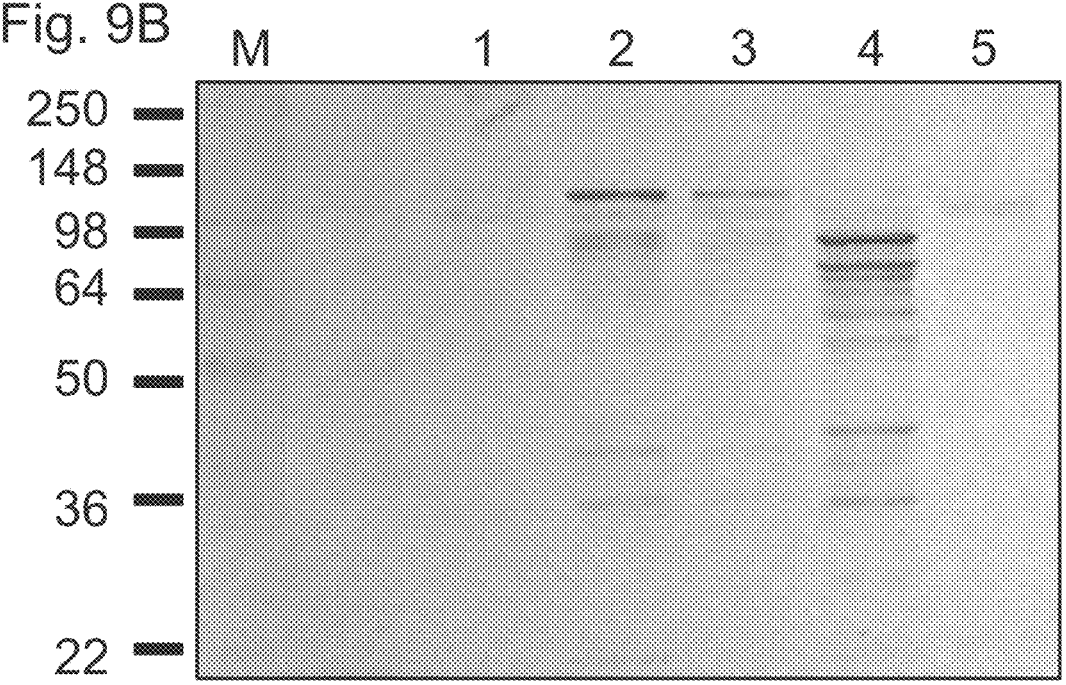
Figure 9C:
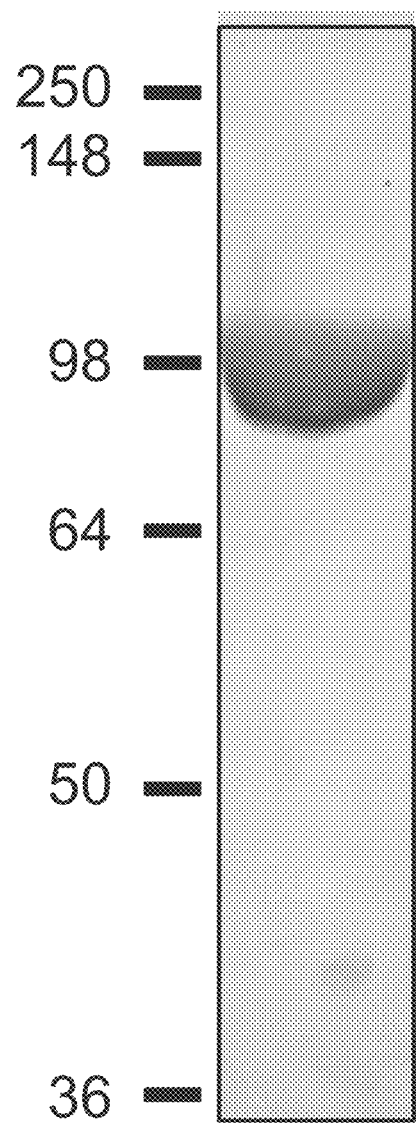

FIG. 9A-9C. SDS-PAGE (8%) separation and Western blots revealed anti-His antiserum showing secreted, cell associated, or purified rBHT-HIS expressed by different *P. pastoris* GS115 recombinants. (9A) Protein cell free extracts (secreted proteins) generated by all recombinants were concentrated 20 fold. (9B) Cell associated proteins were obtained from five $OD_{600}$ of recombinant cells disrupted with glass beads in 1× Laemmli buffer. Lane 1, GS115::αMF-rBht-HIS; lane 2, GS115::αMF-rBht$_{(23-594)}$-HIS; lane 3, GS115::rBht-HIS; lane 4, GS115::rBht$_{(23-594)}$-HIS; and lane 5, GS115 control. (9C) Silver stain of rBHT-HIS expressed by GS115::αMF-rBht$_{(23-594)}$-HIS purified using nickel affinity chromatography and resolved in SDS-PAGE (8%). M indicates marker lane. The molecular masses (kDa) of the marker proteins are shown to the left of the panels.

Figure 10B:
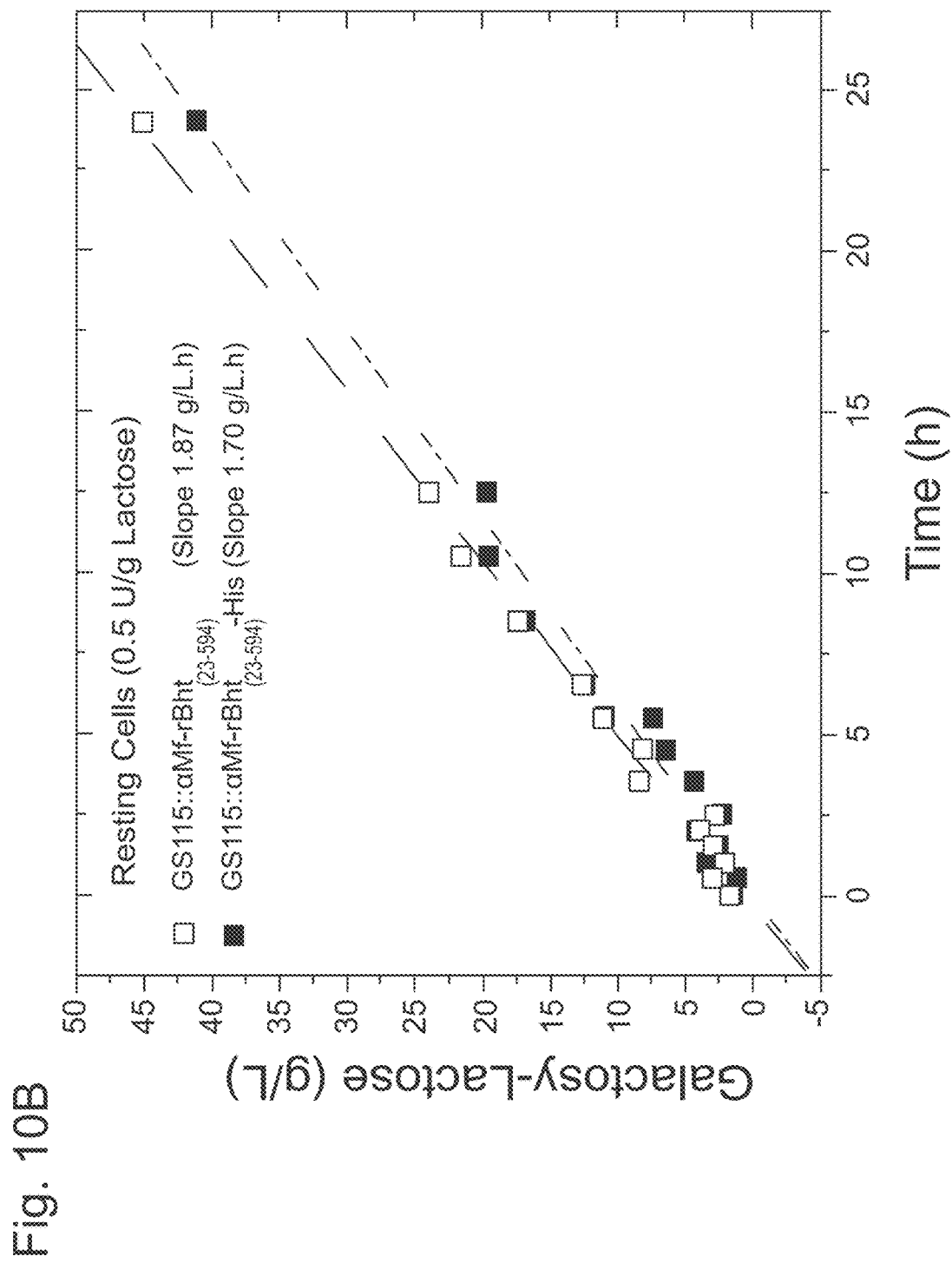

FIG. 10A-10B. Time course of galactosyl-lactose synthesis using soluble rBHT or *P. pastoris* resting cells containing membrane bound rBHT (0.5 U rBHT.g$^{-1}$ lactose). (10A) Synthesis by secreted rBHT-HIS expressed by GS115::αMF-rBht$_{(23-594)}$-HIS (solid line) and rBHT by GS115:: αMF-rBht$_{(23-594)}$ (dashed line). (10B) The rate of galactosyl-lactose synthesis by resting cells GS115::αMF-rBht$_{(23-594)}$-HIS (solid square) and GS115::αMF-rBht$_{(23-594)}$ (open square). Assays contained 200 g·L$^{-1}$ lactose and purified enzyme or resting cells of *P. pastoris* in 5 mM sodium phosphate buffer pH 5.0 and incubated at 30° C. Samples were removed periodically and analyzed by HPLC. Concentrations of lactose, glucose, galactose and galactosyl-lactose are shown in g·L$^{-1}$. The residual non-quantified GOS species are shown as signal intensity readings from the refractive-index detector. Data represents the means of two independent experiments.

5. DETAILED DESCRIPTION OF THE INVENTION

This invention reports several methods for the expression of the *S. singularis* BHT including, but not limited to, a method using a codon optimized, synthetic rBht gene (GenBank accession number JF29828) expressed in *Pichia pastoris*. We investigated the kinetics of GOS production from lactose by the secreted recombinant β-hexosyl-transferase (rBHT) as compared to *P. pastoris* resting cells harboring membrane-bound rBHT.

"rBHT proteins," as meant herein, includes full length rBHT proteins and fragments and/or variants thereof, which includes proteins encoded by naturally-occurring allelic variants of the rBHT gene, as well as recombinantly-produced rBHT proteins, which may contain some sequence changes relative to naturally-occurring rBHT proteins.

A "recombinant" protein is one resulting from the process of genetic engineering. The term "genetic engineering" refers to a recombinant DNA or nucleic acid method used to create a cell that expresses a gene at elevated levels or at lowered levels, or expresses a mutant form of the gene. In other words, the cell has been transfected, transformed or transduced with a recombinant polynucleotide molecule, and thereby altered so as to cause the cell to alter expression of a desired polypeptide.

"galacto-oligosaccharide" or "GOS" means a galactose-containing polysaccharide with two or more sugar units such as Gal-Gal or [Gal]$_n$-Glc (1≤n≤8), including β-D-Gal(1→4)-β-D-Gal(1→4)-β-D-Glc, β-D-Gal(1→4)-β-D-Gal(1→4)-β-D-Gal(1→4)-β-D-Glc, and β-D-Gal(1→4)-β-D-Gal(1→4)-β-D-Gal(1→4)-β-D-Gal(1→4)-β-D-Glc.

5.1. Signal Sequences

Soluble secreted proteins and proteins expressed on the cell surface often comprise an N-terminal "signal sequence," which is a hydrophobic sequence that mediates insertion of the protein through the membrane bounding the endoplasmic reticulum (ER) in a eukaryotic cell. Type 1 transmembrane proteins also comprise signal sequences. "Signal sequences," as meant herein are amino-terminal hydrophobic sequences which are usually enzymatically removed following the insertion of part or all of the protein through the ER membrane into the lumen of the ER. Thus, it is known in the art that a signal sequence can be present as part of a precursor form of a secreted or transmembrane protein, but will generally be absent from the mature form of the protein. When a protein is said to comprise a signal sequence, it is to be understood that, although a precursor form of the protein does contain the signal sequence, a mature form of the protein will likely not contain the signal sequence. Signal sequences may contain a residue adjacent to and immediately upstream from the cleavage site (position −1) and another residue at position −3, which are important for this enzymatic cleavage. Nielsen et al. 1997

*Protein Eng* 10(1) 1-6; von Heijne 1983 *Eur J Biochem* 133(1) 7-21; von Heijne 1985 *J Mol Biol* 184 99-105, the portions of which describe signal sequences and how to identify them are incorporated herein by reference. Signal sequences can be identified as described by Nielsen et al. (supra). Examples of signal peptides or sequences that are functional in mammalian host cells include the following: the *Saccharomyces cerevisiae* pre-pro-alpha-mating factor signal sequence the signal sequence for interleukin-7 (IL-7) described in U.S. Pat. No. 4,965,195: the signal sequence for interleukin-2 receptor described in Cosman et al. 1984 *Nature* 312 768-771); the interleukin-4 receptor signal peptide described in EP Patent 0 367 566; the type 1 interleukin-1 receptor signal sequence described in U.S. Pat. No. 4,968,607; the type II interleukin-1 receptor signal peptide described in EP Patent 0 460 846. Many other signal sequences are known in the art.

5.2. rBHT Protein

The instant invention encompasses secreted, soluble versions of rBHT, as well as versions comprising a transmembrane domain that can be expressed on a cell surface. Such proteins can be isolated, that is, be part of a purified protein preparation in which the rBHT protein constitutes at least 80% or at least 90% of the protein present in the preparation. The invention further includes rBHT proteins encoded by the rBHT nucleic acids described below. An rBHT protein, as meant herein, encompasses a protein comprising the amino acid sequence of SEQ ID NO. 2, 4, 6, 8, 10, 12, 14, 16, 18 or 20, as well as fragments, derivatives, and variants thereof, including fusion proteins. The amino acid sequence of SEQ ID NO. 2, 4, 6, 8, 10, 12, 14, 16, 18 or 20 includes a signal sequence.

5.3. Conservative Substitutions

In some embodiments the substitutions can be conservative amino acid substitutions. Examples of conservative amino acid substitutions, unlikely to affect biological activity, include the following: alanine for serine, valine for isoleucine, aspartate for glutamate, threonine for serine, alanine for glycine, alanine for threonine, serine for asparagine, alanine for valine, serine for glycine, tyrosine for phenylalanine, alanine for proline, lysine for arginine, aspartate for asparagine, leucine for isoleucine, leucine for valine, alanine for glutamate, aspartate for glycine, and these changes in the reverse. See e.g. Neurath et al., *The Proteins*, Academic Press, New York (1979), the relevant portions of which are incorporated herein by reference. Further, an exchange of one amino acid within a group for another amino acid within the same group is a conservative substitution, where the groups are the following: (1) alanine, valine, leucine, isoleucine, methionine, norleucine, and phenylalanine: (2) histidine, arginine, lysine, glutamine, and asparagine; (3) aspartate and glutamate; (4) serine, threonine, alanine, tyrosine, phenylalanine, tryptophan, and cysteine; and (5) glycine, proline, and alanine.

5.4. Glycosylation rBHT proteins may be glycosylated to varying degrees or not glycosylated. As an illustration, an rBHT protein of the invention may comprise one or more N- or O-linked glycosylation sites in addition to those already found in a protein comprising SEQ ID NO. 2, 4, 6, 8, 10, 12, 14, 16, 18 or 20. One of skill in the art would be aware that asparagine residues that are part of the sequence Asn Xxx Ser/Thr (where Xxx is any amino acid except proline) can serve as sites of addition for N-glycans. In addition, there are many serine and threonine residues that may serve as O-linked glycosylation sites. Glycosylation may increase in vivo half-life or alter biological activity. Variants of rBHT proteins also include proteins comprising one, two, three, four, five, six, seven, eight, nine, or ten more N- and/or O-linked glycosylation sites than are present in SEQ ID NO. 2, 4, 6, 8, 10, 12, 14, 16, 18 or 20 as long as the resulting protein can act as a glycosyl hydrolase and a β-hexosyl-transferase. Variant rBHT proteins also include those that have one, two, three, four, or five fewer N- and/or O-linked glycosylation sites than are present in SEQ ID NO. 2, 4, 6, 8, 10, 12, 14, 16, 18 or 20 as long as they can act as a glycosyl hydrolase and a β-hexosyl-transferase.

rBHT proteins, as meant herein, can be fusion proteins comprising at least one rBHT polypeptide, which can comprise an amino acid sequence that is a variant and/or a fragment of SEQ ID NO. 2, 4, 6, 8, 10, 12, 14, 16, 18 or 20 (as explained above), and at least one other moiety. The other moiety can also be a non-protein moiety such as, for example, a polyethylene glycol (PEG) moiety or a cytotoxic, cytostatic, luminescent, and/or radioactive moiety. Attachment of PEG has been shown to increase the in vivo half-life of at least some proteins. Moreover, cytotoxic, cytostatic, luminescent, and/or radioactive moieties have been fused to antibodies for diagnostic or therapeutic purposes.

A variety of polypeptides other than rBHT can be fused to an rBHT polypeptide for a variety of purposes such as, for example, to increase in vivo half-life of the protein, to facilitate identification, isolation and/or purification of the protein, to increase the activity of the protein, and to promote oligomerization of the protein.

Many polypeptides can facilitate identification and/or purification of a recombinant fusion protein of which they are a part. Examples include polyarginine, polyhistidine, or HATrM (Clontech), which is a naturally-occurring sequence of non-adjacent histidine residues that possess a high affinity for immobilized metal ions. rBHT proteins comprising these polypeptides can be purified by, for example, affinity chromatography using immobilized nickel or TALON™ resin (Clontech), which comprises immobilized cobalt ions. See e.g. Knol et al. 1996 *J Biol Chem* 27(26) 15358-15366. Polypeptides comprising polyarginine allow effective purification by ion exchange chromatography. Other useful polypeptides include, for example, the antigenic identification peptides described in U.S. Pat. No. 5,011,912 and in Hopp et al. 1988 *Bio/Technology* 6 1204. One such peptide is the FLAG™ peptide, which is highly antigenic and provides an epitope reversibly bound by a specific monoclonal antibody, enabling rapid assay and facile purification of expressed recombinant fusion protein. A murine hybridoma designated 4E11 produces a monoclonal antibody that binds the FLAG peptide in the presence of certain divalent metal cations, as described in U.S. Pat. No. 5,011,912. The 4E11 hybridoma cell line has been deposited with the American Type Culture Collection under Accession No. HB 9259. Monoclonal antibodies that bind the FLAG peptide can be used as affinity reagents to recover a polypeptide purification reagent that comprises the FLAG peptide. Other suitable protein tags and affinity reagents are: 1) those described in GST-Bind™ system (Novagen), which utilizes the affinity of glutathione-S-transferase fusion proteins for immobilized glutathione; 2) those described in the T7-TAG® affinity purification kit, which utilizes the affinity of the amino terminal 11 amino acids of the T7 gene 10 protein for a monoclonal antibody; or 3) those described in the STREP-TAG® system (Novagen), which utilizes the affinity of an engineered form of streptavidin for a protein tag. Some of the above-mentioned protein tags, as well as others, are described in Sassenfeld 1990 *TIBTECH* 8: 88-93, Brewer et al., in *Purification and Analysis of Recombinant*

*Proteins*, pp. 239-266, Seetharam and Sharma (eds.), Marcel Dekker, Inc. (1991), and Brewer and Sassenfeld, in *Protein Purification Applications*, pp. 91-111, Harris and Angal (eds.), Press, Inc., Oxford England (1990). The portions of these references that describe protein tags are incorporated herein by reference. Further, fusions of two or more of the tags described above, such as, for example, a fusion of a FLAG tag and a polyhistidine tag, can be fused to an rBHT protein of the invention.

5.5. rBHT Nucleic Acids

The invention encompasses isolated nucleic acids, including, for example DNAs and RNAs, that encode the rBHT proteins described herein, which include proteins comprising the amino acid sequence of SEQ ID NO. 2, 4, 6, 8, 10, 12, 14, 16, 18 or 20 and fragments and/or variants thereof. Preferably, the proteins have the amino acid sequence of SEQ ID NO. 12 or 14. These nucleic acids are useful for, inter alia, producing recombinant proteins having glycosyl hydrolase and a β-hexosyl-transferase activity. Such nucleic acids can be modified genomic DNA or cDNA. Preferably, the nucleic acids can comprise an uninterrupted open reading frame encoding an rBHT protein. Nucleic acid molecules of the invention include DNA and RNA in both single-stranded and double-stranded form, as well as the corresponding complementary sequences. An "isolated nucleic acid" is a nucleic acid that has been separated from adjacent genetic sequences present in the genome of the organism from which the nucleic acid was isolated, in the case of nucleic acids isolated from naturally-occurring sources, in the case of nucleic acids synthesized chemically, such as oligonucleotides, or enzymatically from a template, such as polymerase chain reaction (PCR) products or cDNAs, it is understood that the nucleic acids resulting from such processes are isolated nucleic acids. An isolated nucleic acid molecule refers to a nucleic acid molecule in the form of a separate fragment or as a component of a larger nucleic acid construct.

The present invention also includes nucleic acids comprising the sequence of SEQ ID NO. 1, 3, 5, 7, 9, 11, 13, 15, 17, 19, or a fragment thereof or nucleic acids that hybridize under moderately stringent conditions, and optionally highly stringent conditions, to nucleic acids comprising the nucleotide sequence of SEQ ID NO 1, 3, 5, 7, 9, 11, 13, 15, 17, 19, which is the nucleotide sequence of the full length rBHT cDNA, wherein the nucleic acid encodes a protein that can act as a glycosyl hydrolase and a β-hexosyl-transferase. Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, 1989) and *Current Protocols in Molecular Biology* (F. M. Ausubel et al., eds., John Wiley & Sons, Inc., sections 2.10 and 6.3-6.4 1995), the relevant portions of which are incorporated by reference herein. Moderately stringent conditions for filter hybridizations include hybridization in about 50% formamide, 6×SSC at a temperature from about 42° C. to 55° C. and washing at about 60° C. in 0.5×SSC, 0.1% SDS. Highly stringent conditions are defined as hybridization conditions as above, but with washing at approximately 68° C. in 0.2×SSC, 0.1% SDS. SSPE (1×SSPE is 0.15 M NaCl, 10 mM $NaH_2PO_4$, and 1.26 mM EDTA, pH 7.4) can be substituted for SSC (1×SSC is 0.15 M NaCl and 15 mM sodium citrate) in the hybridization and wash buffers; washes, optionally at least two washes, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids (for example, using GAP) and identifying the region or regions of optimal sequence complementarity. The hybridization temperature for hybrids anticipated to be less than 50 base pairs in length should be 5° C. to 10° C. less than the melting temperature (Tm) of the hybrid, where Tm is determined according to the following equations. For hybrids less than 18 base pairs in length, Tm (degrees C.)=2(# of A+T bases)+4(# of G+C bases). For hybrids above 18 base pairs in length, Tm (degrees C.)=81.5+16.6 $(\log_{10}[Na^+])$+0.41 (% G+C)−(600 N), where N is the number of bases in the hybrid, and $[Na^+]$ is the concentration of sodium ions in the hybridization buffer. Each such hybridizing nucleic acid has a length that is at least 15 nucleotides (or at least 18 nucleotides, or at least 20, or at least 25, or at least 30, or at least 40, or at least 50, or at least 100. Sambrook et al., supra.

rBHT nucleic acids include nucleic acids comprising the following polynucleotides: (1) all or a fragment of SEQ ID NO. 1, 3, 5, 7, 9, 11, 13, 15, 17, 19, wherein the fragment encodes an rBHT protein that can act as a glycosyl hydrolase and a β-hexosyl-transferase; (2) a polynucleotide including nucleotide sequences at least 80%. 85%, 90%. 95%, 97%, 98%, 99%, 99.5%, or 99.7% identical to SEQ ID NO. 1, 3, 5, 7, 9, 11, 13, 15, 17, 19, wherein the alignment window is at least 100, 125, 150, 175, 200, 225, 250, 300, 400, 500, 600, 800, 1000. or 1200 nucleotides long and wherein the sequence encodes an rBHT protein that can act as a glycosyl hydrolase and a β-hexosyl-transferase; (3) a polynucleotide that comprises not more than 1, 2, 3, 4, 6. 8, 10, 15, 20, 25, or 30 alteration(s) of a single nucleotide relative to SEQ ID NO. 1, 3, 5, 7, 9, 11, 13, 15, 17, 19, wherein an alteration can be an insertion, deletion or substitution of a single nucleotide, and wherein the polynucleotide encodes an rBHT protein can act as a glycosyl hydrolase and a β-hexosyl-transferase; and (4) a polynucleotide that encodes an rBHT protein as described herein, which includes fragments, derivatives and variants of a rBHT protein. In a preferred embodiment, the rBHT protein is produced by replacing the leader sequence with a heterologous secretion signal peptide.

5.6. Methods of Making rBHT Proteins rBHT proteins can be made as follows. A nucleic acid that encodes an rBHT protein, as described herein, can be introduced into a vector, which can be introduced into a host cell. Vectors and host cells comprising nucleic acids encoding an rBHT protein are encompassed by the invention. The host cell containing the nucleic acids encoding an rBHT protein can be cultured under conditions such that the rBHT protein can be expressed. The expressed rBHT protein can then be obtained from the medium in which the cells are cultured or from the cells and purified by any of the many appropriate means known in the art. In addition, genetic engineering methods for the production of rBHT proteins include the expression of the polynucleotide molecules in cell free expression systems, in cellular hosts, in tissues, and in animal models, according to known methods.

The vector can include a selectable marker and an origin of replication, for propagation in a host. The vector can further include suitable transcriptional or translational regulatory sequences, such as those derived from mammalian, microbial, viral, or insect genes, operably linked to the nucleic acid encoding the rBHT protein. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to an rBHT nucleic sequence if the promoter nucleotide sequence directs the transcription of the rBHT protein-encoding sequence. If the rBHT protein is a fusion protein, a nucleic acid sequence encoding a portion of the fusion protein, for example, a signal sequence, can be part of a vector, and a nucleic acid encoding an rBHT protein can be inserted into the vector such that a protein comprising the added signal sequence plus the rBHT protein is encoded by the vector.

Suitable host cells for expression of rBHT proteins include prokaryotic cells, yeast cells, plant cells, insect cells, and higher eukaryotic cells. The regulatory sequences in the vector will be chosen such that they are operable in the host cell. Suitable prokaryotic host cells include bacteria of the genera *Escherichia, Bacillus*, and *Salmonella*, as well as members of the genera *Pseudomonas, Streptomyces*, and *Staphylococcus*. For expression in prokaryotic cells, for example, in *E. coli* the polynucleotide molecule encoding an rBHT protein preferably includes an N-terminal methionine residue to facilitate expression of the recombinant polypeptide. The N-terminal methionine may optionally be cleaved from the expressed polypeptide. Suitable yeast host cells include cells from genera including *Saccharomyces, Pichia*, and *Kluveromyces*. Preferred yeast hosts are *S. cerevisiae* and *P. pastoris*. A suitable system for expression in an insect host cell is described, for example, in the review by Luckow and Summers (1988 *BioTechnology* 6 47-55), the relevant portions of which are incorporated herein by reference. Suitable mammalian host cells include the COS-7 line of monkey kidney cells (Gluzman et al. 1981 *Cell* 23 175-182), baby hamster kidney (BHK) cells, Chinese hamster ovary (CHO) cells (Puck et al. 1958 *PNAS USA* 60 1275-1281), CV-1 (Fischer et al. 1970 *Int J Cancer* 5 21-27), 293 cells from human kidney (American Type Culture Collection (ATCC®) catalog no. CRL-10852™), and human cervical carcinoma cells (HELA) (ATCC® CCL 2). The relevant portions of the references referred to in this paragraph are incorporated herein by reference.

Expression vectors for use in cellular hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pGEM vectors (Promega), pSPORT vectors, and pPROEX vectors (InVitrogen, Life Technologies, Carlsbad, Calif.), Bluescript vectors (Stratagene), and pQE vectors (Qiagen). Yeast vectors will often contain an origin of replication sequence from a yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast a-factor leader sequence at the 5' end of the rBHT-encoding nucleotide sequence. Brake 1989 *Biotechnology* 13 269-280.

Examples of suitable expression vectors for use in mammalian host cells include pcD A3.1/Hygro (Invitrogen), pDC409 (McMahan et al. 1991 *EMBO J* 10: 2821-2832), and pSVL (Pharmacia Biotech). Expression vectors for use in mammalian host cells can include transcriptional and translational control sequences derived from viral genomes. Commonly used promoter sequences and enhancer sequences that can be used to express rBHT RNA include, but are not limited to, those derived from human cytomegalovirus (CMV). Adenovirus 2, Polyomavirus, and Simian virus 40 (SV40). Methods for the construction of mammalian expression vectors are disclosed, for example, in Okayama and Berg (1982 *Mol Cell Biol* 2: 161-170), Cosman et al. (1986 *Mol Immunol* 23:935-941), Cosman et al. (1984 *Nature* 312: 768-771), EP-A-0367566, and WO 91/18982. The relevant portions of these references are incorporated herein by reference.

5.7. Purification Tags

In addition to the 6×HIS tag described herein a variety of purification methods may be used such as affinity tags, such as antigenic tags (e.g., FLAG (Sigma-Aldrich, Hopp et al. 1988 *Nat Biotech* 6:1204-1210), hemagluttanin (HA) (Wilson et al., 1984 *Cell* 37:767), Intein fusion expression systems (New England Biolabs, USA) Chong et al. 1997 *Gene* 192(2), 271-281, or maltose-binding protein (MBP)), glutathione S transferase (GST)/glutathione, poly His/Ni or Co (Gentz et al., 1989 *PNAS USA* 86:821-824). Fusion proteins containing GST-tags at the N-terminus of the protein are also described in U.S. Pat. No. 5,654,176 (Smith). Magnetic separation techniques may also be used such as Strepavidin-DynaBeads® (Life Technologies, USA). Alternatively, photo-cleavable linkers may be used, e.g., U.S. Pat. No. 7,595,198 (Olejnik & Rothchild). Many other systems are known in the art and are suitable for use with the present invention.

5.8. Methods of Making Galacto-Oligosaccharides (GOS)

In one embodiment of the invention, the galacto-oligosaccharides (GOS) are produced by incubating the cell expressing the rBHT in a medium that comprises a disaccharide substrate such as for example lactose or cellobiose. In one embodiment, the GOS is produced from lactose simultaneously with a glucose removal system. The glucose removal system may be a generally recognized as safe (GRAS) organism.

5.9. Formulations

Another aspect of the invention concerns use of the rBHT protein or cells expressing rBHT to produce a foodstuff or a dietary supplement containing galacto-oligosaccharides (GOS). The foodstuff may be diary foodstuff such as yogurt, cheese or fermented dairy products. The rBHT or cell expressing rBHT may be part added to the foodstuff or dietary supplements. The rBHT may be dried using Spray Dry; a quick and gentle method of obtaining even the smallest quantities of temperature sensitive substances in powder form. The dried rBHT also may be encapsulated form using the Spray dryer's ability to coat particles, immobilize solid material in a matrix and manufacture microcapsules (www.buchi.com/Mini_Spray_Dryer_B-290.179.0 DOT html). Other drug delivery applications using functional GRAS encapsulating agents and technologies may be used. The dried rBHT tablet and powder forms may be analysed for rBHT rate of activity once rehydrated in buffer containing lactose and in milk products.

Examples of the foodstuffs include, but are not limited to, infant formula, dairy products, beverages, and dietary supplements. See Table 2 below.

TABLE 2

| Food group | Food group category |
| --- | --- |
| Infant formulas for term infants and baby foods | Infant formula<br>Infant meal replacement drinks<br>Baby juice<br>Baby yoghurt drinks<br>Baby dessert<br>Baby snack |
| Dairy products | Yoghurt<br>Frozen dairy desserts |
| Milk beverages | Milk<br>Milk drinks<br>Syrup flavoring for milk<br>Meal replacement drinks<br>Milk substitutes |
| Fruit drinks and water quenchers | Fruit drinks (vitamin/mineral fortified) and energy drinks<br>Fitness waters and thirst quenchers |
| Fruit preparations | Fruit pie filling<br>Fruit prep<br>Jelly jam |

Any of the above-described rBHT proteins may be delivered in the form of a composition, that is, with one or more additional components such as a physiologically acceptable carrier, excipient, or diluent. For example, a composition may comprise a soluble rBHT protein as described herein plus a buffer, an antioxidant such as ascorbic acid, a low molecular weight polypeptide (such as those having less than 10 amino acids), a protein, amino acids, carbohydrates such as glucose, sucrose, or dextrin, chelating agent such as EDTA, glutathione, and/or other stabilizers, excipients, and/or preservatives. The composition may be formulated as a liquid or a freeze-dried powder. Further examples of components that may be employed in pharmaceutical formulations are presented in *Remington's Pharmaceutical Sciences*, 16$^{th}$ Ed., Mack Publishing Company, Easton, Pa., (1980), the relevant portions of which are incorporated herein by reference.

Compositions comprising therapeutic molecules described above can be administered by any appropriate means including, but not limited to, parenteral, topical, oral, nasal, vaginal, rectal, or pulmonary (by inhalation) administration. If injected, the composition(s) can be administered intra-articularly, intravenously, intraarterially, intramuscularly, intraperitoneally or subcutaneously by bolus injection or continuous infusion. Localized administration, that is, at the site of disease, is contemplated, as are transdermal delivery and sustained release from implants, skin patches, or suppositories. Delivery by inhalation includes, for example, nasal or oral inhalation, use of a nebulizer, inhalation in aerosol form, and the like. Administration via a suppository inserted into a body cavity can be accomplished, for example, by inserting a solid form of the composition in a chosen body cavity and allowing it to dissolve. Other alternatives include eye drops, oral preparations such as pills, lozenges, syrups, and chewing gum, and topical preparations such as lotions, gels, sprays, and ointments. In most cases, therapeutic molecules that are polypeptides can be administered topically or by injection or inhalation.

The therapeutic molecules described above can be administered at any dosage, frequency, and duration that can be effective to treat the condition being treated. The dosage depends on the molecular nature of the therapeutic molecule and the nature of the disorder being treated. Treatment may be continued as long as necessary to achieve the desired results. The periodicity of treatment may or may not be constant throughout the duration of the treatment. For example, treatment may initially occur at weekly intervals and later occur every other week. Treatments having durations of days, weeks, months, or years are encompassed by the invention. Treatment may be discontinued and then restarted.

Maintenance doses may be administered after an initial treatment. Dosage may be measured as milligrams per kilogram of body weight (mg/kg) or as milligrams per square meter of skin surface (mg/m$^2$) or as a fixed dose, irrespective of height or weight. These are standard dosage units in the art. A person's skin surface area is calculated from her height and weight using a standard formula. For example, a therapeutic rBHT protein can be administered at a dose of from about 0.05 mg kg to about 10 mg/kg or from about 0.1 mg/kg to about 1.0 mg kg. Alternatively, a dose of from about 1 mg to about 500 mg can be administered. Or a dose of about 5 mg, 10 mg. 15 mg 20 mg, 25 mg, 30 mg. 35 mg, 40, mg, 45, mg, 50 mg, 55 mg, 60 mg, 100 mg, 200 mg, or 300 mg can be administered.

The article "a" and "an" are used herein to refer to one or more than one (i.e., to at least one) of the grammatical objects of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

The following Examples further illustrate the invention and are not intended to limit the scope of the invention.

6. EXAMPLES

6.1. Materials and Methods

Design of a Codon Optimized β-Hexosyl-Transferase Gene.

The DNA coding sequence for the *S. singularis* β-hexosyl-transferase gene (16) (GenBank accession number AB 126324; 1,782 bp) was assembled by joining exons using Clone Manager software (Cary, N.C.). The coding sequence was redesigned based on *P. pastoris* and *E. coli* preferred codons, optimized for minimum free energy (−619.9), specific restriction sites (5' NcoI and 3' NotI), and GC content (48.89%). This redesigned version of the gene was labeled rBht (GenBank accession number JF29828), synthesized and inserted into pGS21a and pUC57 to generate pJB100 and pJB107, respectively (Table 1). The DNA sequence of rBht was confirmed (GenScript, Piscataway, N.J.).

Construction of Plasmids Containing rBht for Expression in *E. coli*.

Cloning procedures were carried out as previously described (32). *E. coli* strains used for cloning and expression of rBHT are listed in Table 3. Restriction endonucleases and T4 DNA ligase were obtained from New England Biolabs (Beverly, Mass.). The plasmids pJB100 and pJB107 were digested with NcoI and NotI, and the fragment containing the rBht gene was inserted into Novagen plasmids to generate the expression plasmids pJB101, pJB103, pJB104, pJB105, and pJB106 (see Table 3 for a description of the constructions).

Expression of rBHT Fusion Constructions in *E. coli* BLR.

The expression was carried out as described in the pET system manual TB055 8th Edition 02/99 (Novagen). Briefly, the expression plasmids were transformed into *E. coli* BLR and after IPTG induction screened for rBHT activity. In vivo rBHT activity was assessed by incubating IPTG induced BLR cells in 50 mM sodium phosphate buffer at pH 4 and pH 6, and 50 µg·ml$^{-1}$ cell penetrating chromogenic substrate X-GAL (Table 4). Cultures were incubated overnight at 37° C. for visualization of the appearance of color. BL21 cells containing endogenous β-galactosidase activity were used as the positive control.

Production of Anti-rBHT.

Anti-rBHT antiserum was produced using rBHT-6×HIS expressed and purified from *E. coli* BLR cells harboring pJB101. Purification of rBHT-6×HIS present in the cell free extract fraction was performed by using nickel agarose gel chromatography according to the manufacturer's instructions (QIAGEN, Germany) and then further purified by electro-elution from gels according to manufacturer's instructions (Bio-Rad, Richmond, Calif.). The pure protein was used for rabbit immunization (Cocalico Biologics Reamstown, Pa.). Additional antibodies used in the study are listed in Table 4.

Electrophoresis and Immunoblotting.

Sodium dodecyl sulfate polyacrylaminde gel electrophoresis (SDS-PAGE-4-12%) was routinely carried out in the Laemmli system (23). Proteins were visualized by Coomassie blue (Bio-Rad, Richmond, Calif.) or silver staining (Bio-Rad, Richmond, Calif.). SeeBlue plus (Invitrogen, Carlsbad, Calif.) was used as a molecular mass marker. Immunoblot analysis on duplicate PAGE gels was carried out as previously described (7) except detection was performed using alkaline phosphatase conjugated goat anti-rabbit or goat anti-mouse antibodies (Rockland Immunochemicals, Gilbertsville, Pa.) and visualized using NBT (nitro-blue tetrazolium chloride) and BCIP (5-bromo-4-chloro-3'-indolyphosphate p-toluidine salt) premixed solution (Sigma-Aldrich, St. Louis, Mo.).

Construction of *P. pastoris* Recombinant Strain.

The rBht gene was PCR amplified from pJB107 using primers JBB1 and JBB2 to add XhoI and NotI restriction sites in frame with *Saccharomyces cerevisiae* pre-pro-alpha-mating factor signal sequence contained in pPIC9, followed by a 6×HIS tag, and a modified TEV protease cleavage site (Table 2). The PCR product was ligated into pPIC9 XhoI and NotI restriction sites to generate pJB108 (Table 3). Correct in-frame ligation was confirmed by sequencing (Sequatech, Mountain View, Calif.) using primers 5' AOX1 and 3' AOX1 (Table 4).

*P. pastoris* GS115 (Table 1) was electro-transformed with pJB108 linearized with SacI (Invitrogen's *Pichia* expression kit manual, version M) using a Bio-Rad Gene Pulser (Bio-Rad, Richmond, Calif.). Recombinants were selected on histidine deficient Regeneration Dextrose (RDB-agar plates) at 30° C. His' colonies were randomly selected, and the genomic integration of the expression cassette was verified by PCR using primers 5' AOX1, 3' AOX1, and α-Factor (Table 4). The methanol utilization (mu$^+$) phenotype of recombinant GS115/rBht was determined according to the procedure outlined in Invitrogen's *Pichia* expression kit manual, version M.

rBHT Production in *P. pastoris*.

To select a high-level producer of the recombinant rBHT, six His$^+$ isolates were grown in yeast extract peptone dextrose medium (YPD) at 30° C. and 250 rpm for 12 h and then used to inoculate 100 ml buffered glycerol complex medium (BMGY) to an initial $OD_{600}$=0.1. When the culture exceeded an $OD_{600}$=10, methanol was added to a final concentration of 0.5% at 24 h intervals until the culture exceeded an $OD_{600}$=50 after which methanol was added every 12 h. Media samples were analyzed for presence of BHT activity and by Western blot using rabbit anti-rBHT every 24 h to determine the optimal harvest time. The selected GS115/rBht recombinant was routinely grown in 0.5 L BMGY and induced with methanol for 6 days.

Purification of Secreted rBHT.

Culture supernatants (500 ml) were fractionated with ammonium sulfate. Precipitates between 60%-80% ammonium sulfate were resuspended in 50 mM sodium phosphate buffer (pH 6). After desalting and concentrating with an Amicon MWCO 15 membrane (Amicon Inc., Beverly, Mass.) the solution was applied to a 1/30 (5 ml) Mono Q pre-equilibrated column (Quarternary amino ethyl) (Amersham Biosciences). The column was then washed with 50 ml of buffer and eluted with 3 column volumes of a linear gradient of sodium chloride from 0 to 0.2 M in 50 mM sodium phosphate buffer (pH 6.0) at a flow rate of 1 ml·min$^{-1}$. The eluate was collected in 1 ml portions. The active fractions were pooled, concentrated and resuspended in 10 mM sodium phosphate (pH 6.8), then applied to a Bio-Gel HT hydroxyapatite column (Bio-Rad, Richmond, Calif.) (1/10 2 ml) pre-equilibrated with the same buffer, washed with 10 mM sodium phosphate (pH 6.8), and eluted with 50 mM sodium phosphate (pH 6.8). The fractions with the highest specific activity contained pure rBHT with specific activity of 8.2 U·mg$^{-1}$. Enzymatic activity was assayed (described below) on all chromatography fractions and purification steps were carried out at 25° C.

Determination of Molecular Mass.

Culture medium concentrated 20 fold by ultrafiltration (0.5 ml) was applied to a size exclusion column Superdex 200 (Amersham Biosciences) 1/30 (18 ml) pre-equilibrated with 50 mM sodium phosphate buffer, pH 6.0, 0.1 M NaCl. Fractions of 0.5 ml were collected at a flow rate of 0.5 ml·min$^{-1}$ and assayed for rBHT activity using ONP-Glu as the substrate and by zymogram as described below. Elution of rBHT and molecular mass standards were monitored at 280 nm. The column was calibrated using the following molecules: Thyroglobulin, 669 kDa; Ferritin, 440 kDa; Catalase, 232 kDa; Lactate dehydrogenase, 140 kDa; Bovine Serum Albumin; 67 kDa (GE, Healthcare). The molecular mass of rBHT was extrapolated from a calibration plot of log molecular mass (Y axis) versus elution volume (X axis). All chromatographic steps were carried out at 25° C.

Enzymatic Activity Assays.

The initial reaction rate of rBHT was measured by a modification of the Kuby's method (13,22) under the established conditions. Briefly the reactions were performed in a volume of 250 µl containing 1.3 mM ONP-Glu and 50 mM sodium phosphate buffer (pH 5). The assays were carried out for 10 min under the established conditions and stopped by adding 1 volume of 0.25 M $Na_2CO_3$. The reaction mixture containing boiled rBHT and substrate served as negative control. Assays were always performed in duplicate with a reliability of ±5%. Samples of cell-free broth, and protein concentrates were obtained as described above. Resting cells (harboring membrane-bound rBHT) prewashed with 50 mM sodium phosphate buffer (pH 5.0) were assayed, under established conditions. When X-GAL was the substrate of the reaction the concentration was 50 µg·ml$^{-1}$ in 50 mM sodium phosphate buffer (pH 4).

One unit (U) of enzyme activity equals 1 µmol of o-nitrophenol released per min under the assay conditions. Specific activity is defined as Units/mg protein. Molar extinction coefficients of o-nitrophenol were: ε=0.033 mM$^{-1}$cm$^{-1}$, pH 4; ε=0.036 mM$^{-1}$cm$^{-1}$, pH 5; ε=0.038 mM$^{-1}$cm$^{-1}$, pH 6. The amount of o-nitrophenol released was extrapolated from a calibration plot of the o-nitrophenol absorbance at 405 nm (Y axis) versus o-nitrophenol concentration (X axis).

Enzymatic activities were also visualized by zymograms. Native PAGE were performed using a modification of the protocol described by Gallagher (8). Proteins from *E. coli* lysates or *P. pastoris* supernatants were solubilized in 5% (w/v) sucrose/10 μg·ml$^{-1}$ Bromophenol blue and separated in 6% native polyacrylamide gels, utilizing as running buffer 50 mM sodium phosphate buffer (pH 6). The gel was kept cool in a Mighty Small Hoefer electrophoresis apparatus where cold water was re-circulated during electrophoresis at 60 mA for 5 h. After electrophoresis, the gel was rinsed twice in wash buffer (50 mM sodium phosphate buffer, pH 4.0) for 10 min. The zymograms were developed for 24 h by laying filter paper soaked in wash buffer containing 50 μg·ml$^{-1}$ X-GAL at 20° C. A blue precipitate defined the location of the enzyme.

Enzyme Kinetics.

Series of enzyme dilutions ranging from 0 to 1.2 U·ml$^{-1}$ were assayed in 50 mM sodium phosphate (pH 5) at 42° C. The enzymatic activity assay was initiated by adding 1.3 mM ONP-Glu and the absorbance monitored at 405 nm for 1 min intervals for a total of 20 min. The experimental absorbance values were plotted against time showing linear proportionality up to 0.6 U·ml$^{-1}$ for at least 20 min while at enzyme concentrations above 1.0 U·ml$^{-1}$ the absorbance values plateau prior to 5 min.

The Michaelis-Menten constants ($k_m$ and $V_{max}$) of 0.2 U·ml$^{-1}$ rBHT (at 42° C.) were determined by varying ONP-Glu from 0 to 10.4 mM in 50 mM sodium phosphate (pH 5) and measuring the initial reaction rate at 20° C., 30° C., 40° C., and 50° C. The kinetic constants at each temperature were determined with OriginPro 7.5 using non-linear regression of the Hill equation with a Hill coefficient of 1. The values obtained under the established conditions were as follows (T, $k_m$, $V_{max}$): (20° C., 0.37 mM, 0.09 mM·min$^{-1}$), (30° C., 0.48 mM, 0.12 mM·min$^{-1}$), (40° C., 0.71 mM, 0.23 mM·min$^{-1}$) and (50° C., 1.3 mM, 0.42 mM·min$^{-1}$). The fitting coefficients of regression ($R^2$) were 0.9869, 0.99065, 0.99115 and 0.98996 at 20° C., 30° C., 40° C. and 50° C., respectively.

Characterization of rBHT.

Enzymatic activity assays were performed under the established conditions described above. The influence of pH on enzyme activity was tested in buffer solutions including 50 mM sodium phosphate (pH 5.0 to 11.0), 50 mM citrate (pH 2.0 to 5.0) and 50 mM phosphate-citrate (pH 2 to 11) (FIG. 2A). Competitive inhibition by monosaccharides (glucose and galactose) was examined by varying their concentrations in the reaction mixture (FIG. 2C). Temperature and thermostability were determined by measuring residual activity at 20, 30, 40, 50, 60, 70 or 80° C. (FIGS. 2B and 2D). Similarly, enzymatic activity assays were used to evaluate additives as potential inhibitors/activators. The following additives up to 10 mM were tested: chelating agent (EDTA), reducing agents (dithiothreitol (DTIT), 2-mercaptoethanol (2-ME), and copper ($Cu^{2+}$)), and ions (monovalent cations; $NH_4^+$, $Cs^+$, $K^+$, $Na^+$, $Li^+$, and $Rb^+$; divalent cations; $Ba^{2+}$, $Ca^{2+}$, $Co^{2+}$, $Fe^{2+}$, $Mg^{2+}$, $Mn^{2+}$, $Ni^{2+}$, and $Zn^{2+}$; trivalent cation $Ag^{3+}$). Heavy metals ($Co^{2+}$, $Fe^{2+}$, and $Zn^{2+}$) were tested in 50 mM citrate buffer (pH 5.0) to avoid precipitation. Additionally, surfactants added to the reaction mixture at 1% (v/v) were: TritonX-100, Tween 20, Tween 80, and Sodium Dodecyl Sulfate (SDS). Solvents tested at 10% v/v included: ethanol, methanol, acetone, acetonitrile, PEG400, and glycerol.

GOS Production and Analysis.

The standard transgalactosylation reactions, utilizing either purified rBHT or *P. pastoris* resting cells (harboring membrane-bound enzyme), were initiated by adding standardized amounts of enzyme (0.5 Ug$^{-1}$ lactose) in 5 mM sodium phosphate buffer (pH 5.0) containing lactose (22 gL$^{-1}$ or 200 gL$^{-1}$) at 30° C. or 42° C.

Products and substrates of the reactions were analyzed by high-performance liquid chromatography (HPLC) (Shimadzu Corporation, Kyoto, Japan) under isocratic conditions at 65° C. and at 0.4 ml·min$^{-1}$ flow rate. The mobile phase was 5 mM sulfuric acid ($H_2SO_4$) using an Alltech IOA-1000 organic acids column (300 mm by 7.8 mm) (Alltech, IL) coupled to a refractive-index detector. The column was calibrated using; galactosyl-lactose (Carbosynth (Berkshire, UK)), lactose, glucose, and galactose (Sigma-Aldrich, St. Louis, Mo.). The residual non-quantified GOS species (tetrasaccharide and pentasaccharide) are reported as signal intensity readings from the refractive-index detector.

6.2. Results

Expression of a Recombinant β-Hexosyl-Transferase (rBHT) in *E. coli*.

*E. coli* BL21 is the most widely used host for heterologous protein production. Unfortunately, this host strain contains an active endogenous β-galactosidase that interferes with the evaluation of the β-hexosyl-transferase, designated as rBHT (see materials and methods). After screening different *E. coli* strains appropriate for pET-based expression systems including BL21, BLR, NovaBlue, Origami, and Rosetta (Table 3), *E. coli* BLR was confirmed as lacking of endogenous β-galactosidase activity. *E. coli* CC 118 (ΔlacZ) strain was used as a control (36).

The rBht gene was inserted into pET expression plasmids containing a C-terminal 6×HIS or one of the four solubility-enhancing co-expression partners (glutathione-S-transferase (GST), thioredoxin (Trx), the PelB leader, and DsbA) resulting in pJB101, pJB103, pJB104, pJB105, and pJB106 (Table 3). Transformation into *E. coli* BLR and induction with IPTG resulted in expression of inactive rBHT either in whole cells or in cell free extracts. Immunoblotting analysis of the fusion proteins with rBHT-antiserum detected all rBHT fusion proteins at their predicted molecular masses, with the strongest reactivity observed in the insoluble fractions. To rule out possible host-dependent protein insolubility, rBHT expression was analyzed in *E. coli* CC 118 harboring pJB102 (pJB101 with its T7 promoter replaced with a tetracycline (TET) inducible promoter) but also proved to be unsuccessful (data not shown).

Expression and Purification of rBHT from *P. pastoris*.

*P. pastoris* is able to introduce post-translational modifications and is well known for its ability to produce a number of active recombinant proteins (where *E. coli* fails) (14). Thus, we inserted the codon optimized rBht gene into pPIC9 under the control of the alcohol oxidase promoter (AOX1), in frame with the *S. cerevisiae* α-factor signal (sequence for protein secretion) and an N-terminal 6×HIS followed by a TEV protease cleavage site (pJB108, Table 3). *P. pastoris* GS115 was transformed with pJB108 (GS115/rBht) and the activity of rBHT was evaluated in six GS115/rBht recombinants. The recombinant strain secreting the highest concentration of bioactive protein was studied further. Zymograms confirmed the presence of an active rBHT: only GS115/rBht gave a positive signal, while cell extracts from *E. coli* BLR harboring pJB101 and culture supernatants from untransformed GS115 were negative (FIG. 1C). As expected, protein transmembrane regions in BHT also resulted in GS115/rBht cells displaying cell surface-associated rBHT activity, emulating the location of native BHT in *S. singularis* (15,16).

Purification of rBHT was attempted using nickel affinity chromatography, but the HIS-tag was not present, nor was the protein detected by Western blot analysis using anti-HIS antiserum, indicating possible processing of the N-terminal signal sequence at predicted cleavage sites (16). Subsequently, the rBHT enzyme was purified (specific activity of 8.2 U·mg$^{-1}$ at 20° C.) using Mono Q and hydroxyapatite chromatography (Table 5).

6.3. Characterization of rBHT Expressed in *P. pastoris*.

1. Apparent Molecular Mass of rBHT.

The estimated molecular mass for a non-glycosylated fully processed rBHT that included the 6×HIS and TEV protease site tag was 68 kDa. The enzyme has been previously purified as a dimer as well as a monomer with apparent molecular mass ranging from 53 to 146 kDa data that reflects variations in protein glycosylation (Table 5) (1,16). Here, the enzyme activity eluted as one monomeric peak with an experimental apparent molecular mass of 110 kDa. We surmised that the dimeric form may predominate within the acidic range of the native enzyme's pH optimum (3.7 to 6) (Table 5). However, fractions from the Superdex 200 column at pH 4.0 depicted the same profile, confirming the stable monomeric form of the recombinant enzyme. No higher molecular mass aggregates were detected by enzyme activity assay, zymogram, or Western blot. Purification of the column fractions and immunoblot analysis using anti-rBHT verified that the enzyme migrated as a single band with an apparent molecular mass of 110 kDa (FIGS. 1A and 1B).

2. Substrate Specificity.

ONP-Gal has traditionally been used as substrate for β-galactosidases and ONP-Gal, PNP-Gal and PNP-Glu have all been used in previous studies for detection of native BHT activity (Table 5). The enzyme activities of rBHT (0.2 U·ml$^{-1}$) were compared between the above substrates at the same experimental conditions. The recombinant enzyme was equally active in response to ONP-Glu and PNP-Glu. The substrates with a galactose in the glycon moiety were hydrolyzed at a rate of approximately 41% (ONP-Gal) and 23% (PNP-Gal) of that for ONP-Glu. These results indicate that rBHT has a narrow specificity with respect to the sugar and more flexibility toward configuration of the carbon linkage position at C2 and C4 when glucose sugar derivatives are used as substrates.

3. Optimum pH, Temperature and Thermostability of rBHT.

rBHT was active within a broad pH range (from pH 3.5 to 6) displaying the highest values at pH 4.0 (FIG. 2A). The enzymatic activity profile showed a steep decline to less than 50% maximal enzyme activity at pH values greater than 7 or less than 3.5. These results were consistent with reported pH optimum (1) (see references from Table 5); suggesting that alkaline conditions may have a detrimental effect on enzyme activity and stability.

The initial reaction rate measured at different temperatures ranging from 20° C. to 80° C. indicated that the enzyme was active over a temperature range from 20° C. to 50° C. with the optimum occurring between 40° C. and 50° C. (FIG. 2B). At temperatures below 30° C. a 50% reduction in the initial reaction rate is observed and temperatures above 50° C. quickly and irreversibly inactivated the enzyme. The optimum temperature when maximizing the enzyme reaction rate can also be obtained from the highest value of $V_{max}/K_m$ (33). $V_{max}$ increased at a faster rate than $K_m$ at temperatures between 20° C. to 40° C., consequently the $V_{max}/K_m$ values (0.242 min$^{-1}$, 20° C.; 0.255 min$^{-1}$, 30° C.; 0.324 min$^{-1}$, 40° C.; 0.322 min$^{-1}$, 50° C.) increased over this range and were constant at temperatures between 40° C. and 50° C. Thus the optimum temperature as determined by $V_{max}/K_m$ was within 40° C.-50° C., confirming the optimal values established using the initial reaction rate values at each temperature.

As shown in FIG. 2D, the thermostability of rBHT was evaluated from 20° C. to 50° C. At 20° C. and 30° C. the enzyme retained at least 90% of the original activity for 6 days, confirming previously reported results for the native enzyme (4). Five independent batches of rBHT stored for 6 months at 4° C. retained 95% of the initial activity (data not shown). Although the optimal temperature was found in the 40° C. to 50° C. range, incubation at temperatures above 40° C. was deleterious to rBHT. At 40° C., the enzyme retained 70% of the initial activity by 12 h and this level of activity only persisted for an additional 36 h. In contrast, enzyme activity decreased sharply at 50° C. within the first 12 h incubation period.

4. Effect of Metals, Salts, Surfactants, and Solvents on rBHT Activity.

Enzyme inhibition/activation was tested within a broad range of additives. rBHT did not exhibit a requirement for any of the ions tested (NH$_4^+$, Ba$^{2+}$, Ca$^2$, Cs$^+$, Co$^{2+}$, Cu$^{2+}$, Li$^+$, Rb$^+$, Mg$^{2+}$, Ni$^{2+}$, Na$^+$ and Zn$^{2+}$) even though magnesium dramatically increases the enzyme activity of some β-galactosidases (26). Moreover, the recombinant enzyme was fully active in the presence of 1 and 5 mM of the ion-chelating agent EDTA, confirming the above findings and a previous report (1). Additionally, compounds proven to disrupt disulfide bridges, such as Cu$^{2+}$ and the reducing agents dithiothreitol (DTT) and 2-mercaptoethanol (2ME) (1,18,19), had no negative consequences on the activity. The solvents methanol, ethanol, acetone and acetonitrile only partially inhibit the enzyme (retaining 66%-81% relative activity). In contrast, the addition of 10% glycerol or 1% of SDS (a non-ionic surfactant) almost completely inhibited the enzyme.

GOS Synthesis Using Purified rBHT.

Once the enzyme was characterized, the secreted rBHT was tested for biotransformation of 2% lactose into GOS. The conditions of the reaction were 0.5 U rBHT.g$^{-1}$ of lactose at 42° C. in 5 mM sodium phosphate buffer (pH 5.0). FIG. 3 shows lactose consumption and GOS accumulation over time. The highest rate of production was observed during the first 12 h and galactosyl-lactose and glucose were the main products. Galactose was not detected, indicating that it was being completely incorporated in the transgalactosylation reaction to form GOS. After 30 h, 4.2 g·L$^{-1}$ of glucose had accumulated and lactose utilization (54%) was at its maximum. Furthermore at this time point, 7.8 g·L$^{-1}$ of the trisaccharide had accumulated reaching an average of 67% conversion of the utilized lactose. As the reaction proceeded, galactose began to escape the enzymatic reaction and accumulate at trace concentrations. Since competitive enzyme inhibition could reduce the efficiency of lactose biotransformation, we examined the effect of varying concentrations of glucose or galactose on enzyme activity in the reaction mixture. The presence of 5 g·L$^{-1}$ glucose reduced rBHT activity up to 90% whereas enzymatic activity was unaffected by up to 70 g·L$^{-1}$ galactose, under the established conditions (FIG. 2C).

GOS Synthesis by *P. pastoris* Resting Cells (Harboring Membrane-Bound rBHT).

To avoid competitive inhibition and confirm that conversion of lactose into GOS could be improved upon if glucose is simultaneously eliminated from the reaction mixture, we evaluated the biotransformation of 20% lactose by resting cells of *P. pastoris* GS115/rBht. *P. pastoris* GS115/rBht harboring membrane-bound rBHT were normalized to a cell density containing 0.5 U rBHT.g$^{-1}$ of lactose in 5 mM sodium phosphate buffer (pH 5). Reactions were conducted for 10 days at 30° C., the optimal temperature for growth of *P. pastoris*, and at 42° C., the temperature for which the initial reaction rate is at its maximum for the secreted rBHT. As expected, 90% of the initial lactose was converted into GOS with no secondary products at 30° C., as compared to 51% lactose utilization at 42° C. The results indicated that resting cells were physiologically active and able to consume the glucose byproduct of the reaction, thereby avoiding competitive inhibition. However, the initial reaction rate of GOS formation at 42° C. was double the rate at 30° C. during the first 48 h. A final concentration of 80 g·L$^{-1}$ galactosyl-lactose was reached, corresponding to a productivity of 1.6 g·L$^{-1}$·h$^{-1}$ at 42° C. (FIG. 4A). At 30° C. when the lactose utilization was at 63% the concentration of galactosyl-lactose was 100 g·L$^{-1}$ and a productivity of 0.8 g·L$^{-1}$·h$^{-1}$ was reached after 5 days (FIG. 4B).

6.4. Discussion

In this study we optimized the DNA sequence of the β-hexosyl-transferase gene from *S. singularis* (acc. number AB 126324) for expression in *E. coli* and *P. pastoris*. The resulting rBht gene was synthetically generated (acc. number JF29828) and expressed in *E. coli*. However, this bacterial host lacked the ability to incorporate post-translational modifications essential for producing a soluble and active rBHT as previously observed (16). Subsequently, the rBht gene under the control of the AOX1 promoter was successfully integrated into the *P. pastoris* chromosome, resulting in the expression of a fully active enzyme that was detected in the culture broth as well as associated with the cell surface. Secretion of rBHT by *P. pastoris* GS115 allowed us to avoid the complex purification processes that are required to obtain pure BHT from *S. singularis*. Furthermore, since *P. pastoris* naturally secretes only very low levels of native proteins, recovery of the extracellular rBHT was as simple as removal of whole cells from the medium by centrifugation or filtration (5).

The molecular mass of the recombinant enzyme corresponded to a single 110 kDa catalytically active polypeptide and no smaller polypeptides or rBHT aggregates were detected. Posttranslational modifications play a critical role in protein folding, structural stability, oligomer formation and substrate recognition (17,24), so it was not surprising that the molecular mass was higher than the 68 kDa protein expressed in *E. coli* and predicted by the amino acid sequence. Posttranslational glycosylation of the native BHT by *S. singularis* has been previously reported, and a shift in the molecular mass of the purified protein from 73.9 to 66.3 kDa was observed after treatment with chitinase and EndoHf (16). Future mutagenesis of the predicted glycosylation sites should aid in determining whether glycosylation is also the cause for the shift in rBHT molecular mass.

The data reported here are part of a larger study that compared the utilization of rBHT to documented data for the native *S. singularis* BHT (Table 5). Our study confirmed that the recombinant enzyme does not require cofactors or reducing agents often essential for β-galactosides. The enzyme showed better thermostability at lower temperatures (below 40° C.) and optimal activities at temperatures from 40° C. to 50° C. and pH 3.5 to 6. Additionally, the enzyme was controlled by glucose inhibition though rBHT was not sensitive to galactose or Ag$^{3+}$ as previously reported for native BHT (4,16,25,35).

Lactose utilization and initial lactose concentration are two key factors that contribute to maximizing the final GOS accumulation. Here, we demonstrated a process with improved lactose utilization (90%) employing physiologically active resting cells of *P. pastoris* GS115/rBht. Under these conditions, the cells consume residual glucose at 30° C., circumventing glucose inhibition and ensuring a significant process improvement and a higher degree of final prebiotic purity (FIG. 4B). In contrast, temperatures higher than 25° C. were reported as preventing *S. singularis* resting cells containing membrane-bound native BHT from consuming residual glucose, which in turn limits final GOS concentration and purity (reviewed by Gosling et al. (11)).

GS115/rBht resting cells incubated at 42° C. only converted 51% of the initial lactose into galactosyl-lactose and residual glucose (FIG. 4A). These data closely resembled galactosyl-lactose formation by secreted rBHT under the same conditions (FIG. 3). Furthermore, conversion and utilization values were comparable to previously reported processes by *S. singularis* (Table 5). Typical lactose utilization values have been reported between 30% to 40% of initial lactose (11), with one study reporting 50% lactose utilization using 10.8 times more enzyme per gram of lactose compared to secreted rBHT (Table 5)(4).

The discovery of GOS synthesis by *S. singularis* in the mid-20 century has encouraged the exploration for superior β-galactosidases that more efficiently produce GOS (9,10, 37). However, the enzymes studied showed lower lactose utilization values and higher final concentrations of undesirable byproducts when compared to the BHT from *S. singularis* (1,4,12,16,27,34,35). Nevertheless, advances in the industrial utilization of *S. singularis* BHT have been slower than desired due to the challenging multistep purification processes required to obtain pure native BHT (1,4, 16). The bioactive rBHT either secreted or membrane bound enzyme from *P. pastoris* signifies a clear process advantage for producing GOS. Future studies will explore protein modification strategies to improve protein expression yield, protein stability, and enzyme activity.

Table 6 below summarizes the constructs that were prepared in connection with this invention. All the constructs were prepared in pPIC9 but Exist as chromosomal integrants in *P. pastoris*.

6.5. Galacto-Oligosaccharides from Lactose-Rich Whey

The global dairy market was $299.7B in 2009, and is expected to grow to $370.9B by 2014, an increase of 23.8%. Global. Dairy Industry Profile: Global. *Dairy Industry Profile: Global* [serial online]. October 2010:1. Available from: Business Source Complete, Ipswich, Mass. Accessed Feb. 24, 2012. *Global* (2012). Milk and cheese accounted for 35.2% and 28.3% of the market, respectively. Global cheese consumption is expected to reach 21 million tons in 2015. Lenoir-Wijnkoop I. & van Aalderen W M, B.G.K.D.S.A.N.MJ. Cost-effectiveness model for a specific mixture of prebiotics in The Netherlands. *Eur J Health Econ* (2010). The growth of the dairy market creates significant industrial waste treatment issues given the high lactose content of milk and byproducts produced during dairy processing. High lactose content waste fluids have an exceptionally high biological oxygen demand (BOD), which means that the amount of oxygen required to break down the lactose is high enough to rob other organisms of oxygen needed for survival. Therefore, many countries have enacted environmental protection laws that restrict the disposal of lactose containing fluids directly into bodies of water. Ganzle, M. G., Haase, G. & Jelen, P. Lactose: Crystallization, hydrolysis and value-added derivatives. *International Dairy Journal* 18, 685-694 (2008). The added burden to municipal water treatment processes can be especially costly and problematic for countries and states dependent on a dairy economy (4-6). Affertsholt-Allen T. Market developments and industry challenges for lactose and lactose derivatives. IDF Symposium "Lactose and its Derivatives." Moscow. (lactose.ru/present/1Tage_Affertsholt-Allen DOT pdf. Accessed Sep. 30, 2009) (2007); Markets and Markets. U.S. Digestive Health Ingredients Market Worth $495.3 million in 2015. (www.marketsandmarkets.com/PressReleases/us-digestive-health-ingredients-market DOT asp) (2010); UBIC consulting. THE WORLD GALACTO-OLIGOSACCHARIDE MARKET. (www.ubic-consulting.com/template/fs/documents/Dairy-Ingredients/Galacto-Oligosaccharide-Ingredient-Market DOT pdf) (2010). For example, cheese manufacturing generates two products: cheese and whey. For every pound of cheese made, nine pounds of whey are generated, creating a growing surplus of whey (186 million tons in 2008), which contains ~5% lactose. This lactose fraction has a BOD that is approximately 175-fold greater than typical sewage effluent, therefore the untreated waste cannot be directly disposed into bodies of water. Smithers, G. W. Whey and whey proteins. "From Glitter to Gold". *International Dairy Journal* 18, 695-704 (2008). The traditional solution to this problem has been to bioremediate lactose-rich effluents by applying expensive processes to extract the lactose, which can then be sold as a commodity product at a ceiling value of $1.50/kg. Only 50% of the cheese whey produced annually is recycled into useful products such as food ingredients and animal feed. The rest is considered waste either because critical volumes to allow for economical recycling are not reached or due to the high degree of technical difficulty involved in biotransformation. Therefore, there is a strategic need to convert lactose into commercially viable, high value products to reduce the overall process cost and improve the US dairy industry economy.

Here, we propose the simultaneous biotransformation/bioremediation of the commodity chemical lactose by applying a new food product development process as the ideal solution to this industrial problem. We have improved a method by which lactose can be converted into galactosyl-lactose derivatives called galacto-oligosaccharides (GOS) through an enzymatic reaction. GOS are classified as prebiotics, which stimulate the growth and activity of beneficial bacteria in the digestive system, and are widely used in food products such as infant formulas, nutritional supplements, yogurts, baked goods, and animal feed. Unlike the commodity product lactose, GOS are highly valued food ingredients, and the economic value of this transformation is easily demonstrated by comparing the current market price of lactose at $1.50/kg to the $5.20-8.50/kg market price of GOS. GOS are a part of a trend in digestive health food ingredients valued at $265.9 million in 2010 with an annual growth rate of 18.3% and expected to grow at a compound annual growth rate of 13.2% from 2010 to 2015.

Our lactose to GOS conversion method is vastly superior to existing processes because we can reduce the overall volume of reaction by 50 fold by utilizing an efficient host to produce the enzyme, increase the volume and purity of GOS produced, and potentially generate lactose-free products. Euromonitor. Lactose-free Foods Maintain Their Global Appeal, Mar. 1, 2011. *Euromonitor* (2011). The lactose free product global market was $3.4B in 2009, and is expected to grow as consumers continue to focus on health and wellness functional foods. While other dairy products are extremely price sensitive, functional foods such as lactose-free products can be sold at a premium.

By using the improved process described herein, US and global dairy industry and food supplement manufacturers can clearly benefit in three ways: 1) creation of large volumes of quality GOS, a health promoting food ingredient/dietary supplement with high market value, 2) simultaneous potential generation of valuable lactose free milk or whey products, and 3) cost effective reduction of environmental impact through the recycling of whey and milk byproducts.

TABLE 3

Strains and plasmids used in this study

| Strains/Plasmids | Description or genotype | Source or Reference |
|---|---|---|
| Strains | | |
| *E. coli* | | |
| BL21 | F$^-$ ompT hsdS$_B$(r$_B^-$ m$_B^-$) gal dcm (DE3) | Novagen |
| BLR | F$^-$ ompT hsdS$_B$(r$_B^-$ m$_B^-$) gal dcmΔ(srl-recA)306::Tn10(Tet$^R$)(DE3) | Novagen |
| CC118 | F2 D(ara-leu)7697 araD139 Δ(lac)X74 phoAD20 galE galK thi rpsE rpoB argE(Am) recA1 | (36) |
| NovaBlue | endA1 hsdR17(r$_{K12}^-$ m$_{K12}^+$) supE44 thi-1 recA1 gyrA96 relA1 lacF'[proA$^+$B$^+$ lacI$^q$ ZΔM75::Tn10] (Tet$^R$) (DE3) | Novagen |
| Origami | Δ(ara-leu)7697 ΔlacX74 ΔphoA PvuII phoR araD139 ahpC galE galK rpsLF'[lac$^+$ lacI$^q$ pro] gor522::Tn10 trxB (Kan$^R$, Str$^R$, Tet$^R$) (DE3) | Novagen |
| Rosetta | F$^-$ ompT hsdS$_B$(r$_B^-$ m$_B^-$) gal dcm pRARE2 (Cam$^R$)(DE3) | Novagen |
| XL1-Blue | recA1 endA1 gyrA96 thi-1 hsdR17 supE44 relA1 lac [F′ proAB lacI$^q$ZΔM15 Tn10 (Tet$^R$)] | Stratagene |
| *P. pastoris* | | |
| GS115 | his4 (his$^-$ mut$^+$) | Invitrogen |
| GS115/LacZ | GS115 his4::LacZ (*E. coli* β-galactosidase (117 kDa) intracellularly (his$^+$mut$^+$)) | Invitrogen |
| KM71 | GS115 arg4 his4 aox1::ARG4 (his$^-$ mut$^s$) | Invitrogen |
| JB208 (GS115/rBht) | GS115 integrated with plasmid pJB108 (his$^+$mut$^+$) | This study |
| Plasmids | | |
| *E. coli* | | |
| pJB100 | pGS21a-rBHT | This study |
| pET24d | Optional C-terminal 6XHIS tag, T7lac promoter, Kan$^R$ | Novagen |
| pJB101 | pET24d-rBHT-6XHIS | This study |
| pJB102 | pET24d-TET promoter-rBHT-6XHIS | This study |
| pET41a | GST tag, T7lac promoter, Kan$^R$ | Novagen |
| pJB103 | pET41a-GST-rBHT | This study |
| pET32a | Trx tag, T7lac promoter, Amp$^R$ | Novagen |
| pJB104 | pET32a-Trx-rBHT | This study |
| pET22b | PelB coding sequence, T7lac promoter, Amp$^R$ | Novagen |
| pJB105 | pET22b-pelB-rBHT | This study |
| pET39b | DsbA•tag ™ coding sequence, T7lac promoter, Kan$^R$ | Novagen |
| pJB106 | pET39b-DsbA-rBht | This study |
| pJB107 | pUC57-rBHT | This study |
| *P. pastoris* | | |
| pPIC9 | *P. pastoris* expression plasmid carrying AOX1 promoter and transcription terminator, HIS4, Amp$^r$ in *E. coli*, PBR322 ori, α-factor secretion signal from *S. cerevisiae* | Invitrogen |
| pJB108 | pPIC9-αMF-6XHIS-TEV-rBHT | This study |

αMF, *S. cerevisiae* α-mating factor secretion signal.

TABLE 4

Primers, antibodies and substrates used in this study

| | | <sup>a</sup>Sequence | Source |
|---|---|---|---|
| Primers | Open Reading Frame | | |
| JBB1 | 6XHIS-TEV-rBHT forward primer | 5'-ccg<u>CTCGAG</u>AAAAGAGAGGCTGAAGCTCACCACCACCACCACCACGAAAACCTGTATTTTCAGATGATGCTGCATGCTGCAC-3' | This study (SEQ ID NO: 21) |
| JBB2 | rBHT reverse primer | 5'-aaggaaaaaa<u>GCGGCCGC</u>TTACAGATGATTACGCCCAAATTG-3' | This study (SEQ ID NO: 22) |
| JBB3 | rBHT forward internal sequencing primer | 5'-ATCACTATGCCAGCACGCAGTGTA-3' | This study (SEQ ID NO: 23) |
| JBB4 | rBHT reverse internal sequencing primer | 5'-TTTAAAGCCGATTTCACCTGCCGC-3' | This study (SEQ ID NO: 24) |
| 5' AOX1 sequencing Primer | AOX1 | 5'-GACTGGTTCCAATTGACAAGC-3' | Invitrogen (SEQ ID NO: 25) |
| 3' AOX1 sequencing primer | AOX1 | 5'-GCAAATGGCATTCTGACATCC-3' | Invitrogen (SEQ ID NO: 26) |
| α-Factor sequencing primer | α-factor | 5'-TACTATTGCCAGCATTGCTGC-3' | Invitrogen (SEQ ID NO: 26) |
| Antibodies | Antigen | | |
| Mouse anti-HIS | 6XHIS | | Qiagen |
| Rabbit anti-Bgal | *E coli* β-galactosidase | | Sigma |
| Rabbit anti-rBHT | β-hexosyl-transferase | | This study |
| Substrate | Abbreviation | | |
| oNP-β-D-glucopyranoside | ONP-Glu | | Sigma |
| oNP-β-D-galactopyranoside | ONP-Gal | | Sigma |
| pNP-β-D-glucopyranoside | PNP-Glu | | Sigma |
| pNP-β-D-galactopyranoside | PNP-Gal | | Sigma |
| 5-bromo-4-chloro-3-indolyl-β-D-galactopyranoside | X-GAL | | Sigma |

<sup>a</sup>Coding regions are capitalized, restriction sites have been underlined.

TABLE 5

Reports evaluating BHT from *Sporobolomyces singularis* for the production of galactooligosaccharides (GOS)

| Enzyme Named | MM | SA | T | pH | U.g$^{-1}$·lac | L$_{int}$ | L$_{util}$ | C$_{max}$ (Y) | Conditions Used | Ref |
|---|---|---|---|---|---|---|---|---|---|---|
| β-transglycosyl | — | — | 22 | 3.75-4.0 | — | 10 | — | 50 | STR. Growing cells | (9) |
| β-hexosyl-transferase | — | — | 20 | 6.5 | — | 6 | 68 | 25(36) | Cell extract | (10) |
| β-hexosidase | 140-145 | 41.2$^a$ | 45-50 | 6.5 | — | 5 | — | — | Purified enzyme | (1) |
| β-galactosidase | — | — | 45 | 3.7 | — | 30 | 73 | 54$^e$(51) | Batch IE, partially purified enzyme | (34) |
| β-galactosidase | — | — | 45 | 4.8 | — | 10 | 70 | 55$^e$(53) | Cont. IE, PBR, partially purified enzyme | (34) |
| β-galactosidase | — | — | 45 | 3.7 | 0.13 | 30 | 70 | 40(57) | Partially purified enzyme | (35) |
| β-galactosidase | 53 | 56$^b$ | 50 | 5.0 | 5.4 | 18 | 71 | 50(70) | Purified enzyme | (4) |
| β-galactosidase like | 146 | 8.69$^c$ | 40 | 6.0 | 0.8 | 20 | — | — | Purified enzyme | (16) |
| β-galactosidase | — | — | 55 | 5.0& 6.0 | — | 60 | 60 | 41.1(68) | Batch, resting cells | (31) |
| β-galactosidase | — | — | 55 | 5.0& 6.0 | — | 60 | 60 | 40.4(67) | RB IE Alginate, resting cells | (31) |
| β-hexosyl-transferase | 110 | 8.2$^d$ | 42 | 6.0 | 0.5 | 2 | 52 | 37$^f$(71)$^f$ | Purified enzyme | This study |
| β-hexosyl-transferase | 110 | — | 42 | 6.0 | 0.5 | 20 | 52 | 36$^f$(70)$^f$ | Batch, recombinant resting cells | This study |
| β-hexosyl-transferase | 110 | — | 30 | 6.0 | 0.5 | 20 | 69 | 51$^f$(74)$^f$ | Batch, recombinant resting cells | This study |

MM molecular mass (kDa);
SA specific activity (U.mg$^{-1}$ enzyme);
T temperature (° C.);
U.g$^{-1}$lac units per gram initial lactose;
L$_{int}$ initial lactose concentration (%);
L$_{util}$ lactose utilized (%);
C$_{max}$ maximum conversion of GOS (%) from initial lactose;
(Y) conversion % (total GOS formed from utilized lactose);
STR stirred tank reactor;
IE immobilized enzyme;
PBR packed bed reactor;
Cont. IE immobilized enzyme (continuous);
RB IE immobilized enzyme (repeated batch). Substrates of the enzyme reaction
$^a$ONP-Gal;
$^b$PNP-Gal;
$^c$PNP-Glu;
$^d$ONP-Glu.
$^e$GOS include disaccharides;
$^f$GOS values reported were performed at the value of maximum accumulation of trisaccharide (galactosyl-lactose)

TABLE 6

*Pichia pastoris* rBHT Proteins

| | Protein construct | | | Protein Construct without aMF | | | |
|---|---|---|---|---|---|---|---|
| FP # | Name | Amino Acid # | Mol. Weight | Amino acid # w/o aMF | Mol. weight w/o aMF | Signal sequence | Plasmid |
| 1 | aMF-6XHIS-TEV(Q/M)-rBHT | 695 | 76599.3 | 606 | 67279.3 | aMF and BHTss | pPIC9 |
| 2 | aMF-6XHIS-TEV(Q/M)-aMF-rBHT-6XHIS | 701 | 77422.2 | 612 | 68102.1 | aMF and BHTss | pPIC9 |
| 3 | aMF-rBHT-6XHIS | 689 | 75805.8 | 600 | 66484.4 | aMF and BHTss | pPIC9 |
| 4 | aMF-rBHT | 683 | 74981.6 | 594 | 65661.6 | aMF and BHTss | pPIC9 |
| 5 | aMF-rBHT(Δ1-22)-6XHIS | 667 | 73604.7 | 578 | 64284.6 | aMF | pPIC9 |

TABLE 6-continued

Pichia pastoris rBHT Proteins

| | Protein construct | | | Protein Construct without aMF | | |
|---|---|---|---|---|---|---|
| FP # | Name | Amino Acid # | Mol. Weight | Amino acid # w/o aMF | Mol. weight w/o aMF | Signal sequence | Plasmid |
| 6 | aMF-rBHT(Δ1-22) | 661 | 72781.8 | 572 | 63461.7 | aMF | pPIC9 |
| 7 | rBHT-6XHIS | 600 | 66483.3 | 600 | 66484.4 | BHTss | pPIC9 |
| 8 | rBHT(Δ1-22)-6XHIS | 579 | 64414.7 | 579 | 64415.8 | | pPIC9 |
| 9 | aMF-rBHT(Δ1-110)-6XHIS | 584 | 65005.4 | 491 | 55146.5 | aMF | pPIC9 |

αMF = Saccharomyces cerevisiae alpha mating factor found in pPIC9 vector
BHTss = BHT signal sequence found in amino acids 1-22

6.6. Secretion of β-Hexosytransferase is Enhanced by Replacing Signal Domain

6.6.1. Abstract

The β-hexosyltransferase (BHT) from *Sporobolomyces singularis* is known for its ability to catalyze transgalactosylation reactions and synthesize galacto-oligosaccharides (GOS). We previously reported the heterologous expression of a bioactive full-length polypeptide (rBHT) by a recombinant strain of *Pichia pastoris* (GS115::αMF-HIS-TEV-rBht). This recombinant strain carries the full length Bht gene preceded by the *Saccharomyces cerevisiae* a mating factor pre pro signal (αMF), a histidine tag, and a TEV cleavage site. After methanol induction the rBHT generated by GS115::αMF-HIS-TEV-rBht was only partially secreted and most of the protein remained associated to the cell membrane. To increase the amount of secreted rBHT, this work examines the uncharacterized BHT amino-terminus region (amino acids 1-110) containing two putative endogenous structural domains. The amino terminus includes a domain (amino acids 1-22) which may serve as a classical secretion leader signal while the remaining 23-110 amino acids contain a putative non-classical secretion signal. Thus, we functionally evaluated these domains by generating recombinant *P. pastoris* GS115 strains expressing rBHT-HIS. The results show signal interference affecting protein secretion when αMF was followed by the rBht$_{(1-22)}$ classical leader signal (amino acids 1-22), while the substitution of the leader signal (amino acids 1-22) with the αMF (αMF-rBht$_{(23-594)}$) enhanced *P. pastoris* production of both secreted and membrane bound enzyme by as much as 50 and 14 fold, respectively. To validate the BHT amino-terminus domains role promoting protein secretion, we tested the domains with a non-secreted alternative protein, the anti-3-galactosidase single chain variable antibody fragment scFv13R4. Recombinant *P. pastoris* strains expressing combinations of the αMF and amino-terminus domains of rBHT, followed by the antibody scFv13R4 were able to generate results that correlate with the strength of secretion obtained by the recombinants expressing rBHT-HIS. Finally, active rBHT-HIS and rBHT proteins obtained from the more efficient recombinants (GS115::αMF-rBht$_{(23-594)}$-HIS and GS115::αMF-rBht$_{(23-594)}$) were purified to homogeneity and evaluated for possible alterations in enzyme activity. The enzymatic activity of the 6×HIS tagged and the non-tagged secreted enzymes were comparable as shown by the rates of GOS generation.

6.6.2. Introduction

There is an increasing interest in the use of enzymes for the production of functional foods, especially in the field of prebiotic production from lactose to obtain lactose derivatives. *Sporobolomyces singularis* can assimilate lactose and glucose but not galactose indicating that they are only capable of metabolizing the glucose portion of lactose. Moreover, the unutilized galactose monomer can be only found in the broth as a constituent of the galacto-oligosaccharides (GOS). This physiological feature led to the discovery of the β-hexosyltransferase (BHT) (Blakely and Mackenzi 1021-25; Phaff and Carmo-Sousa 193-207; Spencer, de Spencer, and Laluce 147-56; Gorin, Phaff, and Spencer 1341-44; Gorin, Spencer, and Phaff 2307-17). Prebiotics such as GOS synthesized by the BHT from *S. singularis* are recognized as GRAS and widely used as a functional food additive (Tzortzis and Vulevic 207-44).

In addition to the synthesis of GOS from lactose, BHT also catalyzes the hydrolysis of β-glycosidic linkages such as ONP-Glu and PNP-Glu (Blakely and Mackenzi 1021-25). BHT enzymatic capabilities are particularly appealing with respect to competing technologies, since it is one of few enzymes capable of catalyzing the production of GOS with industrial advantages including; catalysis occurring in the absence of additional ions and cofactors as well as its ability to perform transgalactosylation reactions independently of the initial lactose concentration (Gosling et al. 307-18; Blakely and Mackenzi 1021-25).

In *S. singularis*, Bht is an inducible gene that is repressed by glucose and when in the presence of an inductor such as lactose the generated enzyme (BHT) is mostly found associated to the cell membrane. Due to the cellular location, the purification of BHT requires multiple chromatography steps and has been recovered from *S. singularis* at very low yields ranging from 14% to 16% (Blakely and Mackenzi 1021-25; Cho, Shin, and Bucke 2107-11; Ishikawa et al. 331-39). Since, conventional protein purification protocols limit enzyme recovery and thereof its technological application, alternative strategies have been evaluated. The first approach consisted of exposing *S. singularis* to selection through mutagenesis. Applying this methodology a new strain was selected lacking glucose repression and able to generate a 10-fold increase in membrane bound BHT; however, there was no reported increase in the production of secreted enzyme (Ishikawa et al. 331-39). Alternatively, we recently described that *P. pastoris* GS115 is capable of secreting a biologically active recombinant rBHT polypeptide when preceded by the αMF prepro secretion signal consisting of a 19 amino acid signal sequence (presequence) followed by a 66 amino acid prosequence and a dibasic Kex2 endopeptidase processing site (Kurjan and Herskowitz 933-43). In this study the analysis of the cell free extract and membrane-bound associated activity showed that the majority of the enzyme remained associated to the cell membrane.

Hence showing that *P. pastoris* GS115 is an adequate host for production and secretion of the bioactive rBHT that will facilitate downstream processing and demonstrating the feasibility of production of both secreted and membrane-associated bioactive rBHT (Dagher et al., 2013).

A further look into the native BHT protein sequence showed that it contains endogenous structural features at the amino-terminus, including amino terminal domains that may serve as suitable classical and non-classical secretion signals. Supporting these roles as leader signals, it has been shown that following treatment of *S. singularis* with cell wall lytic enzymes most of the released BHT was devoid of the amino terminal classical leader signal (Ishikawa et al. 331-39). Since the efficiency of gene expression and protein secretion may be affected by those protein structural elements participating in cell association and secretion, the same functions may also be extended to the protein cellular localization when expressed by *P. pastoris* GS115.

In this study, we tested the physiological role of the BHT amino-terminal domains and their relationship with protein secretion by *P. pastoris* GS115. Furthermore, the secretory roles of rBHT amino-terminal domains were validated using recombinant chimeras containing as carboxyl terminal the single chain anti-β-galactosidase antibody scFv13R4. The antibody scFv13R4 is an example of a non-secreted hyperstable single chain protein that is independent of disulfide bridge formation for binding activity (Martineau, Jones, and Winter 117-27). As such, scFv13R4 has been heterologously expressed in *Escherichia coli, Saccharomyces cerevisiae,* and Chinese hamster ovary cells (CHO) (Visintin et al. 11723-28; Grage and Rehm 254-62; Bach et al. 79-93).

6.6.3. Results

In silico protein sequence analysis of the β-hexosyl transferase (BHT). The carboxyl terminal portion (amino acids 111 to 594) of the BHT polypeptide (594 amino acids) has noticeably homology to β-glucosidases. This glycohydrolase I (GHI) domain contains the putative catalytic acid/base, catalytic nucleophile, and three asparagine residues potentially required for protein N-glycosylation (FIG. 7A). Remarkably, the BHT amino terminus revealed a unique region that spans the first 110 amino acids. This region comprises an amino terminal classical leader signal domain (amino acids 1 to 22) followed by a predicted (www.cbs.dtu.dk/services/SecretomeP) non-classical secretion signal (NC) of low complexity (amino acids 72 to 83) (mendel.imp.ac.at/METHODS/seg.server DOT html). The amino terminal leader signal (amino acids 1 to 22) can be further broken down into the N-region (amino terminal; amino acids 1 to 5), H-region (hydrophobic; amino acids 6 to 17) and C-region (carboxyl terminal; amino acids 18 to 22) (FIG. 7B). Alternative algorithms such as the Phobius web-based program (phobius.sbc.su.se/) and the SignalP algorithm (www.cbs.dtu.dk/services/SignalP/) also predicted the putative classical leader signal and potential cleavage sites between residues 17 and 18 and between 22 and 23. Furthermore, the classical leader signal was predicted to contain five amino acids that contact the membrane within the H-region (RHYTHM, proteinformatics.charite.de/rhythm/) and a charge distribution that could facilitate localizing and secretion of membrane proteins (Boyd and Beckwith 1031-33). The trans-membrane region prediction algorithm (www.ch.embnet.org/software/TMPRED_form DOT html) also forecasted a stretch of hydrophobic residues from 1-17 and 177-199 in BHT typical for integral membrane spanning proteins and non-cytoplasmic region (amino acids 23-594) as depicted in the Kyte and Doolittle hydropathy plot (FIG. 7C). These structural features may also indicate that the amino terminal classical leader signal may act as a membrane anchor during passage through the yeast secretory pathway.

Amino terminal domains participate in protein secretion. To investigate the probable physiological roles of the two amino terminal secretion domains (classical and non-classical secretion signals), expression of the carboxyl terminal BHT domain (amino acids 111 to 594) and the single chain anti-β-galactosidase antibody (scFv13R4) were tested. Stable recombinant *P. pastoris* GS115 strains were obtained by chromosomal integration of the appropriate modified gene combinations preceded by the rBht amino terminal domains and/or the strong 9.3 kDa αMF prepro sequence. The rBht and scFv13R4 gene combinations were inserted downstream of the AOX1 promoter and followed by carboxyl-terminal 6×HIS tag to assist detection and purification FIGS. 8A and 8D (see Materials and Methods).

Replacement of the leader signal (amino acids 1 to 22) with the strong αMF prepro secretion signal (GS115::αMF-rBht$_{(23-594)}$-HIS) increased protein secretion to more than 19 fold (9.80 µg·ml$^{-1}$) compared to expression of the full-length rBHT-HIS preceded by αMF secretion signal (GS115::αMF-rBht-HIS) (0.49 µg·ml$^{-1}$) (FIG. 8B). Similarly, in the absence of the αMF, the leader signal was able to direct the heterologous protein for secretion (GS115::rBht-HIS) (6.35 µg·ml$^{-1}$). Additionally, protein secretion was detected in the absence of both αMF and leader signals (GS115::rBht$_{(23-594)}$-HIS) (4.65 µg·ml$^{-1}$), suggesting that both the classical leader and the non-classical secretion signals contain information targeting the protein for secretion.

To validate that the amino-terminal domains, as described above, target proteins to the secretory pathway, we choose the antibody scFv13R4, an intracellular protein depleted of signal sequences. Diagrams of the antibody scFv13R4 chimeras are shown in FIG. (8C). The scFv13R4-HIS when expressed by GS115::scFv13R4-HIS (lacking leader secretion signals) could not be detected in the culture broth by SDS-PAGE silver staining or Western blot analysis (data not shown). Secretion of scFv13R4-HIS by GS115::rBht$_{(1-110)}$-scFv13R4-HIS or GS115::rBht$_{(23-110)}$-scFv13R4-HIS manifested when either scFv13R4 was fused to the Bht classical leader secretion signal (25.17 µg·ml$^{-1}$), or when fused to the Bht non-classical signal (7.03 µg·ml$^{-1}$). Likewise, as seen with BHT-HIS, secretion driven by αMF, (GS115::αMF-scFv13R4-HIS) provided the highest level of secreted protein (91.02 µg·ml$^{-1}$).

Enzyme activity and Western blot analysis of rBHT-HIS expressed by *P. pastoris* GS115. To confirm that protein expression correlated with enzymatic activity, the secreted and the membrane bound rBHT-HIS activities were measured using ONP-Glu as the substrate (see Materials and Methods). All recombinant strains secreted rBHT-HIS in detectable amounts and the values of activity reflected increases in secreted protein. The protein secreted by GS115::αMF-rBht$_{(23-594)}$-HIS displayed an enzymatic activity of 3.7 mU·OD$^{-1}$ that was 6-fold higher than the measured activity when secretion was driven by the complete amino terminal region (amino acids 1-110) (GS115::rBht-HIS (0.63 mU·OD$^{-1}$)). Similarly, the measured enzymatic activity of the protein secreted by GS115::αMF-rBht$_{(23-594)}$-HIS was 53-fold higher than obtained from the recombinant containing both the αMF and the leader signals (GS115::αMF-rBht-HIS (0.07 mU·OD$^{-1}$)). The recombinant GS115::rBht$_{(23-594)}$-HIS (0.26 mU·OD$^{-1}$) show a reduced amount of active secreted enzyme Table 8.

The activity of the membrane-bound enzyme displayed by resting cells of each recombinant was also tested. We found values of activity that correlate with total secreted protein showing an increase in membrane bound activity of 15-fold for the strain GS115::αMF-rBht$_{(23-594)}$-HIS (21.52 mU·OD$^{-1}$) and 1.3-fold increase for the strain GS115::rBht-HIS (1.94 mU·OD$^{-1}$) compared to GS115::αMF-rBht-HIS (1.48 mU·OD$^{-1}$). The recombinant GS115::rBht$_{(23-594)}$-HIS (0.15 mU·OD$^{-1}$) show a reduced amount of membrane bound enzyme, confirming that this recombinant redirects the protein through the putative non-classical secretion pathway. Overall these results show that neither αMF nor the BHT leader secretion signal could fully complete the secretion of rBHT-HIS which may be related to the presence of a transmembrane region predicted between amino acids 177 to 199.

Western blot analysis of the cell-free extracts using anti-HIS antibody confirmed the secreted protein values by GS115::αMF-rBht$_{(23-594)}$-HIS, GS115::rBht-HIS, and GS115::rBht$_{(23-594)}$-HIS (FIG. 9A). In each case the prominent rBHT-HIS band corresponding to a molecular mass of approximately 110 kDa was present. These results are in agreement with previously reported SDS-PAGE and size exclusion chromatography migration patterns (Dagher, Azcarate-Peril, and Bruno-Bárcena). Western blot analysis of cell extracts obtained from GS115::αMF-rBht$_{(23-594)}$-HIS, GS115::rBht-HIS, and GS115::αMF-rBht-HIS also exhibited a molecular mass of approximately 110 kDa, while GS115::rBht$_{(23-594)}$-HIS showed prominent bands between 98 and 64 kDa that may indicate intracellular degradation or alternative glycosylation patterns (FIG. 9B).

rBHT hydrolytic activity. Additionally, we tested the secreted enzymes for both HIS-tagged and non-HIS tagged protein from GS115::αMF-rBht$_{(23-594)}$-HIS and GS115::αMF-rBht$_{(23-594)}$, respectively. The enzymes delivered comparable results and were active in a wide range of temperatures (10 to 50° C.) and at pH values (2.8 to 6). Maximum activity was observed from pH 3.6 to 5 (91 to 100% of maximum activity) followed by a steady decrease down to pH 2.6 (43% of maximum) and up to pH 6.8 (29% of maximum). Likewise, the optimum temperature was found in the range of 40 and 45° C. (97 to 100% maximum activity) but rapidly decreased at temperatures above 50° C. and below 20° C. (less than 25% of maximum) (data not shown). The enzyme was stable in 50 mM sodium phosphate buffer pH 5 at 4° C. for at least 6 months and the activity was unaffected by storage at −80° C. The values for the kinetic constants for the enzyme secreted by GS115::αMF-rBht$_{(23-594)}$-HIS were obtained from the Hill equation (Km 0.79 mM and Vmax 3.97 mmol·min$^{-1}$ per mg$^{-1}$ of enzyme at 42° C. pH 4). Those findings were in agreement with previous reports by us and others (Blakely and Mackenzi 1021-25; Cho, Shin, and Bucke 2107-11; Gorin, Phaff, and Spencer 1341-44; Gorin, Spencer, and Phaff 2307-17; Ishikawa et al. 331-39; Sakai et al. 285-93; Shin, Park, and Yang 787-92; Shin and Yang 484-89; Dagher, Azcarate-Peril, and Bruno-Bárcena).

rBHT stability. To examine the long-term stability of the enzyme, all the freshly induced recombinant strains were incubated in buffer containing 2% glucose and the hydrolytic activity of membrane bound and secreted rBHT was measured over time. Secreted rBHT-HIS obtained from all recombinants through classical or non-classical secretion pathway remained stable over the one-week testing period and retained more than 95% of initial activity. The same stability was observed when resting cells containing membrane-associated enzyme was expressed by GS115::αMF-rBht-HIS, GS115::rBht-HIS, and GS115::αMF-rBht$_{(23-594)}$-HIS. However, when testing resting cells containing membrane-associated enzyme expressed by GS115::rBht$_{(23-594)}$-HIS, the activity began to decrease within 24 h pointing to the alternative non-classical secretion pathway.

Purification and characterization of rBHT-HIS generated by GS115::αMF-rBht(23-594)-HIS. The rBHT protein expressed by GS115::αMF-rBht(23-594)-HIS was purified using nickel affinity chromatography. The placement of the 6×HIS tag on the carboxyl-terminus successfully allowed the single step recovery of more than 73% of the original enzymatic activity and after SDS-PAGE a single polypeptide band of approximately 110 kDa was seen (FIG. 9C). The 6.54 fold protein purification from the culture supernatant recovered 7.24 mg of enzyme rendering a specific activity of 18.45 mU·mg-1 at 42° C. and pH 4 (Table 9). Moreover, following the same methodology we purified the rBHT-HIS secreted by the different recombinants and found comparable specific activities ranging from 18.45 to 18.65 mU·mg-1. A determination of the amino-terminal sequences of the secreted polypeptide by GS115::αMF-rBht(23-594)-HIS showed that the entire rBHT(23-594)-HIS protein was present in the broth (V-X-Y-P-G residues)(residues 90-94 of SEQ ID NO:12) in addition to a product containing two additional amino-terminal amino acids (E-A-V-X-Y residues) (residues 88-92 of SEQ ID NO:12). Variability in the cleavage of amino acids A-E during secretion can be affected by the surrounding amino acid sequence and the tertiary structure (Cereghino and Cregg 45-66). The remaining non-classical sequence did not introduce a new cleavage site.

HIS tag impact on rBHT transferase activity. Recombinants GS115::αMF-rBht$_{(23-594)}$-HIS and GS115::αMF-rBht$_{(23-594)}$ were further employed to comparatively evaluate whether the presence of the HIS tag may impact GOS synthesis from lactose. GOS accumulation was analyzed quantitatively by HPLC from reaction mixtures containing 220 gL$^{-1}$ initial lactose, 0.5 U rBHT g$^{-1}$ lactose and incubated at 30° C.

FIG. 10A shows comparative GOS accumulation and lactose consumption over time when the reaction was catalyzed by either the 6×HIS tagged or non-tagged secreted enzymes. In both cases the maximum rate of production was observed during the first 25 h with galactosyl-lactose as the main product. Confirming previously described enzymatic competitive glucose inhibition after 125 h, galactosyl-lactose (75 gL$^{-1}$) accumulation was stationary reaching an average of 67% conversion from the 60% initial lactose utilized (Dagher, Azcarate-Peril, and Bruno-Bárcena).

When using resting cells expressing membrane-associated HIS and non-HIS tagged rBHT, comparative GOS accumulation and lactose consumption over time was also confirmed. (FIG. 10B) shows that the presence of carboxyl-terminal HIS had no impact on the initial reaction rate of galactosyl-lactose formation (1.87 and 1.7 g·L$^{-1}$·h$^{-1}$). As previously reported, the glucose was consumed by resting cells of *P. pastoris* while the galactose was used to synthesize GOS (68% yield (g/g)) approaching the theoretical yield of 75% (Dagher, Azcarate-Peril, and Bruno-Bárcena).

6.6.4. Discussion

Prebiotics are carbohydrate derivatives marketed as functional foods and actively promoted to improve consumer health that is intended to specifically stimulate the growth of beneficial bacteria in the gut. The fundamental force that drives development of prebiotics is the promise of more efficient production processes at lower operating costs. However, production or synthesis of specific carbohydrate derivatives by chemical methods is complex and requires protection and deprotection steps due to the presence of several hydroxyl groups of similar reactivity (Sears and Wong 2344-50). Therefore, the development of enzymatic approaches is of practical interest and genetic modification has been extensively used to modify enzymatic activity, to obtain a deeper knowledge of catalytic mechanisms, and to increase protein secretion. Proteins destined for secretion are usually preceded by amino-terminal leader signals of 20-30 amino acids and eventually processed by membrane bound signal peptidases (Von Heijne 17-21). Protein secretion by *P. pastoris* is influenced by the nature of the initial nucleotide sequences and occasionally requires codon optimization, as well as consideraton of glycosylation patterns, final 3-dimensional structure, culture conditions, and medium composition (Damasceno, Huang, and Batt 31-39). Additionally, the distribution of charged amino acids within leader domains plays an important role in facilitating the localization of membrane and secreted proteins (Boyd and Beckwith 1031-33).

As reported previously, *P. pastoris* offers advantages over *E. coli* for the expression of rBHT thanks to its ability to efficiently incorporate post-translational modifications that allowed for the heterologous production of small amounts of bioactive rBHT. In silico analyses of BHT suggested that this enzyme contains trans-membrane domains that needed to be studied to increase secretion of the enzyme by *P. pastoris*. The BHT unique protein region (1-110 amino acids) contains two domains predicted to function as classical leader signal ($BHT_{(1-22)}$) and non-classical secretion signal domains ($BHT_{(23-110)}$). The classical leader signal also targets the protein to perform its function at the cellular membrane (as predicted by the RHYTHM method and hydropathy plots, FIG. 1). In particular, the presence of basic amino acids such as arginine at position 17 could be implicated in secretion efficiency and protein orientation in the membrane (FIG. 1).

The data presented here shows protein secretion interference by GS115::αMF-rBht-HIS due to the simultaneous presence of αMF and leader signal ($BHT_{(1-22)}$). The levels of protein secretion were comparable to the previously reported values by GS115::αMF-HIS-TEV-rBht (Dagher, Azcarate-Peril, and Bruno-Bárcena). On the other hand, higher accumulation of secreted protein was obtained by the recombinants GS115::rBht-HIS and GS115::αMF-rBht$_{(23-594)}$-HIS lacking either αMF or $BHT_{(1-22)}$, respectively. Therefore, demonstrating that the leader signal domain ($BHT_{(1-22)}$) is involved in the signal peptide-mediated mechanism (classical secretory pathway) comparable to αMF. Both leader signals were individually able to increase protein expression of membrane-associated and secreted rBHT compared to GS115::αMF-rBht-HIS, containing both leader sequences. The best values for secreted (50-fold increase) and membrane-bound (14-fold increase) bioactive rBHT protein were obtained by the recombinant GS115::αMF-rBht$_{(23-594)}$-HIS (Table 3). The subsequent purification of the bioactive protein expressed from GS115::αMF-rBht$_{(23-594)}$-HIS resulted in very pure protein by SDS-PAGE with a specific activity of 18.45 U·mg$^{-1}$ (Table 4). The molecular mass of rBHT (110 kDa) did not deviate between cell membrane-associated and secreted rBHT and displayed similar enzyme activity, thermostability, reusability and storage stability compared with rBHT from our previous study (Dagher et al., 2013).

We expected that removal of both the leader domains ($BHT_{(1-22)}$) and αMF would hinder enzyme secretion. However, elimination of both αMF and $BHT_{(1-22)}$ still showed low amounts of secreted protein. Also confirming that the 110 amino acid unique region contains a dual function by which the leader domain $BHT_{(1-22)}$ acts as an efficient secretion signal (classical secretion pathway) and the predicted $BHT_{(23-110)}$ domain may operate as alternative secretion signal (non-classical secretion pathway). Western blot analyses show proteolysis indicating increased protein sensitivity in the cell. The majority of the measured hydrolytic activity was detected as multiple bands below the maximal mass of 110 kDa, likely affecting the amount of secreted enzyme (FIG. 9A-9C). We speculate that the signal sequences may act to protect the protein during secretion by maintaining the protein away from proteases within the secretory pathway.

Although greater amounts of protein were secreted by GS115::αMF-rBht$_{(23-594)}$-HIS, significant quantities remained stably bound to the membrane, possibly due to the predicted limited mobility in the membrane by the presence of the trans-membrane domain within the protein carboxy-terminus domain (amino acids 177-199). Therefore, to confirm the physiological function of these domains as secretory signals we generated new protein chimeras by replacing the rBHT$_{(23-594)}$ domain with the antibody scFv13R4 protein. The $BHT_{(1-110)}$ classical leader followed by putative non-classical leader, the $BHT_{(23-110)}$ putative non-classical leader, and the αMF domain were placed in frame at the amino terminal position with scFv13R4. Analyses of these new recombinants were able to corroborate the leader secretory function by directing the antibody to secretion. Our results confirm that the choice of signal sequences has a strong impact on both production and secretion levels of proteins including the recombinant BHT and scFv13R4. Noteworthy is the fact that the new smaller leader signal (22 amino acids) has a size advantage compared to αMF (66 amino acids) and has been demonstrated here to be a new unique sequence able to direct secretion of heterologous proteins. This leader signal domain adds a new feature that can be built into intracellular enzymes that otherwise need to be extracted by disruption using mechanical means or permeabilization with chemical treatments (Panesar et al. 530-43).

Continued molecular development of BHT will help address food industries problems for enzymes with novel properties such as thermo-activity, cold stability and synthesis of specific oligosaccharides. The present findings motivate further structural analysis to elucidate features that contribute to transglycosylation activity and substrate specificity. Mutagenesis of catalytic sites and rational mutagenesis based on the 3D structure will pave the way for alterations in substrate specificity for production of novel GOS as prebiotic candidates.

TABLE 7

Strains and plasmids used in this study

| Strains/Plasmids | $^a$Description or genotype | Source or Reference |
|---|---|---|
| Strains | | |
| *E. coli* | | |
| XL1-Blue | recA1 endA1 gyrA96 thi-1 hsdR17 supE44 relA1 lac [F′ proAB lacI$^q$ZΔM15 Tn10 (Tet$^R$)] | Stratagene |
| *P. pastoris* | | |
| GS115 | his4 (his$^-$ mut$^+$) | Invitrogen |
| JB210 | GS115::αMF-rBht-HIS (his$^+$ mut$^+$) | This study |
| JB212 | GS115::αMF-rBht$_{(23-594)}$-HIS (his$^+$ mut$^+$) | This study |

TABLE 7-continued

Strains and plasmids used in this study

| Strains/Plasmids | [a]Description or genotype | Source or Reference |
|---|---|---|
| JB213 | GS115::αMF-rBht$_{(23-594)}$ (his[+] mut[+]) | This study |
| JB214 | GS115::rBht-HIS (his[+] mut[+]) | This study |
| JB215 | GS115::rBht$_{(23-594)}$-HIS (his[+] mut[+]) | This study |
| JB217 | GS115::αMF-scFv13R4-HIS (his[+] mut[+]) | This study |
| JB220 | GS115::rBht$_{(1-110)}$-scFv13R4-HIS (his[+] mut[+]) | This study |
| JB221 | GS115::rBht$_{(23-110)}$-scFv13R4-HIS (his[+] mut[+]) | This study |
| JB222 | GS115::scFv13R4-HIS (his[+] mut[+]) | This study |
| Plasmids | | |

TABLE 8

Secreted and membrane bound rBHT-HIS enzyme activity by different recombinants of P. pastoris Mean activity (mU · OD$^{-1}$) ± SD [a]

| Enzyme Source | Secreted | Membrane bound | Ratio Secreted/Membrane Bound |
|---|---|---|---|
| GS115::αMF-rBht$_{(23-594)}$-HIS | 3.70 ± 0.063 | 21.52 ± 1.38 | 0.172 |
| GS115::rBht-HIS | 0.63 ± 0.018 | 1.94 ± 0.02 | 0.325 |
| GS115::rBht$_{(23-594)}$-HIS | 0.26 ± 0.003 | 0.15 ± 0.02 | 1.606 |
| GS115::αMF-rBht-HIS | 0.07 ± 0.003 | 1.48 ± 0.02 | 0.046 |

TABLE 9

PURIFICATION OF RBHT-HIS SECRETED BY P. PASTORIS GS115::AMF-RBHT$_{(23-594)}$-HIS

| Enzyme Source | Total activity in media (UL$^{-1}$)[a] | Total protein in media (mg)[b] | Specific activity media (U.mg$^{-1}$)[c] | Ni column (U)[d] | Ni column (mg)[e] | Specific activity Ni column (U.mg$^{-1}$)[f] | Purification (fold)[g] | Recovery (%)[h] |
|---|---|---|---|---|---|---|---|---|
| GS115::αMF-rBht$_{(23-594)}$-HIS | 180.67 | 64.00 | 2.82 | 133.54 | 7.24 | 18.45 | 6.54 | 73.91 |

[a]1 Liter of culture was grown in BMGY broth at 28° C.
[b]Protein concentration determined by Bradford assay.
[c]Specific activity is expressed as the total activity (U) divided by the total protein (mg).
[d]Total units following nickel chromatography purification.
[e]Total protein (mg) following nickel chromatography purification.
[f]Specific activity expressed as total activity (U) divided by total yield (mg) following nickel chromatography purification.
[g]Increase in specific activity.
[h]Yield expressed as total activity following nickel column chromatography divided by total activity in the broth.

TABLE 7-continued

Strains and plasmids used in this study

| Strains/Plasmids | [a]Description or genotype | Source or Reference |
|---|---|---|
| E. coli | | |
| pJB100 | pGS21a-rBht | Dagher, 2013 |
| pPM163R4 | pPM160 containing the anti-β-galactosidase antibody gene scFv13R4 | Martineau, 1998 |
| P. pastoris | | |
| pPIC9 | P. pastoris integrative vector carrying AOX1 promoter and transcription terminator, HIS4, Amp[r] in E. coli, pBR322 ori, α-mating factor secretion signal from S. cerevisiae (αMF) | Invitrogen |
| pJB110 | pPIC9-αMF-rBht-HIS | This study |
| pJB112 | pPIC9-αMF-rBht$_{(23-594)}$-HIS | This study |
| pJB113 | pPIC9-αMF-rBht$_{(23-594)}$ | This study |
| pJB114 | pPIC9-rBht-HIS | This study |
| pJB115 | pPIC9-rBht$_{(23-594)}$-HIS | This study |
| pJB117 | pPIC9-αMF-scFv13R4-HIS | This study |
| pJB120 | pPIC9-rBht$_{(1-110)}$-scFv13R4-HIS | This study |
| pJB121 | pPIC9-rBht$_{(23-110)}$-scFv13R4-HIS | This study |
| pJB122 | pPIC9-scFv13R4-HIS | This study |

[a]αMF, S. cerevisiae α-mating factor secretion signal found in pPIC9 vector.

6.7. References for Section 6.6

Bach, Horacio, et al. "Escherichia coli maltose-binding protein as a molecular chaperone for recombinant intracellular cytoplasmic single-chain antibodies." Journal of Molecular Biology 312.1 (2001): 79-93.

Boyd, Dana and Jon Beckwith. "The role of charged amino acids in the localization of secreted and membrane proteins." Cell 62.6 (1990): 1031-33.

Cereghino, J. L. and J. M. Cregg. "Heterologous protein expression in the methylotrophic yeast Pichia pastoris." FEMS Microbiol. Rev. 24.1 (2000): 45-66.

Damasceno, Leonardo, Chung Jr Huang, and Carl Batt. "Protein secretion in Pichia pastoris and advances in protein production." Applied Microbiology and Biotechnology 93.1 (2012): 31-39.

Grage, Katrin and Bernd H. A. Rehm. "In Vivo Production of scFv-Displaying Biopolymer Beads Using a Self-Assembly-Promoting Fusion Partner." Bioconjugate Chemistry 19.1 (2007): 254-62.

Kurjan, Janet and Ira Herskowitz. "Structure of a yeast pheromone gene (MFa): A putative a-factor precursor contains four tandem copies of mature a-factor." Cell 30.3 (1982): 933-43.

Martineau, Pierre, Peter Jones, and Greg Winter. "Expression of an antibody fragment at high levels in the bacterial cytoplasm." Journal of Molecular Biology 280.1 (1998): 117-27.

Panesar, Parmjit S., et al. "Microbial production, immobilization and applications of B-D-galactosidase." Journal of Chemical Technology & Biotechnology 81.4 (2006): 530-43.

Sears, P. and C. H. Wong. "Toward automated synthesis of oligosaccharides and glycoproteins." *Science* 291.5512 (2001): 2344-50.

Spencer, J. F. T., A. L. R. de Spencer, and C. Laluce. "Non-conventional yeasts." *Appl. Microbiol. Biotechnol.* 58.2 (2002): 147-56.

Tzortzis, George and Jelena Vulevic. "Galacto-Oligosaccharide Prebiotics." *Prebiotics and Probiotics Science and Technology*. Ed. Dimitris Charalampopoulos and RobertA Rastall. Springer New York, 2009. 207-44.

Visintin, Michela, et al. "Selection of antibodies for intracellular function using a two-hybrid in vivo system." *Proceedings of the National Academy of Sciences* 96.21 (1999): 11723-28.

Von Heijne, Gunnar. "Patterns of Amino Acids near Signal-Sequence Cleavage Sites." *European Journal of Biochemistry* 133.1 (1983): 17-21.

7. REFERENCES

1. Blakely, J. A. and S. L. Mackenzi. 1969. Purification and properties of a b-hexosidase from *Sporobolomyces singularis*. Can. J. Biochem. 47:1021-1025.
2. Boehm, G., J. Jelinek, B. Stahl, K. van Laere, J. Knol, S. Fanaro, G. Moro, and V. Vigi. 2004. Prebiotics in infant formulas. J. Clin. Gastroenterol. 38:S76-S79.
3. Boehm, G. and B. Stahl. 2007. Oligosaccharides from milk. J. Nutr. 137:847S-849S.
4. Cho, Y. J., H. J. Shin, and C. Bucke. 2003. Purification and biochemical properties of a galactooligosaccharide producing b-galactosidase from *Bullera singularis*. Biotechnol. Lett. 25:2107-2111.
5. Cregg, J. M., T. S. Vedvick, and W. C. Raschke. 1993. Recent advances in the expression of foreign genes in *Pichia pastoris*. BioTechnol. 11:905-910.
6. Cuppa, G. V. and O. Gabrelll. 2008. Human milk oligosaccharides as prebiotics, p. 131-146. In J. Versalovic and M. Byand Wilson (eds.), Therapeutic microbology. Probiotics and related strategies. ASM Press Washington D.C. Chapter.
7. Dagher, S. F., J. L. Wang, and R. J. Patterson. 1995. Identification of Galectin-3 as a factor in pre-mRNA splicing. Proc. Natl. Acad. Sci. U.S.A. 92:1213-1217.
8. Gallagher, S. R. 1995. Current protocols in protein science, p. 10.3.1-10.3.11.
9. Gorin, P. A. J., H. J. Phaff, and J. F. T. Spencer. 1964. Structures of Galactosyl-lactose and Galactobiosyl-lactose produced from lactose by *Sporobolomyces singularis*. Can. J. Chem. 42:1341-1344.
10. Gorin, P. A. J., J. F. T. Spencer, and H. J. Phaff. 1964. Synthesis of b-galacto-b-gluco-pyranosyl disaccharides by *Sporobolomyces singularis*. Can. J. Chem. 42:2307-2317.
11. Gosling, A., G. W. Stevens, A. R. Barber, S. E. Kentish, and S. L. Gras. 2010. Recent advances refining galactooligosaccharide production from lactose. Food Chem. 121:307-318.
12. Grosova', M. Rosenberg, and Rebroš. 2008. Perspectives and applications of immobilised b-galactosidase in food industry—a review. Czech J. Food Sci. 26:1-14.
13. Hestrin, S., D. S. Feingold, and M. Schramm. 1955. Hexoside hydrolases. Meth. Enzymol. 1:231-257.
14. Higgins, D. R. 1998. Introduction to *Pichia pastoris*. Methods Mol. Biol. 103:1-15.
15. Hofmann. 1993. TMbase—A database of membrane spanning proteins segments. Biol. Chem. Hoppe-Seyler 374.
16. Ishikawa, E., T. Sakai, H. Ikemura, K. Matsumoto, and H. Abe. 2005. Identification, cloning, and characterization of a *Sporobolomyces singularis* b-galactosidase-like enzyme involved in galacto-oligosaccharide production. J. Biosci. Bioeng. 99:331-339.
17. Jenkins, N., R. B. Parekh, and D. C. James. 1996. Getting the glycosylation right: Implications for the biotechnology industry. Nat. Biotechnol. 14:975-981.
18. Katayama, K. 1984. Inhibition by copper ion of the activities of b-galactosidase and dehydrogenases of activated sludge. Japan J. Wat. Pollut. Res. 7:100-107.
19. Katayama, K. 1986. Inhibition of the activities of b-galactosidase and dehydrogenases of activated sludge by heavy metals. Water Res. 20:591-594.
20. Kim, C. S., E. S. Ji, and D. K. Oh. 2004. A new kinetic model of recombinant b-galactosidase from *Kluyveromyces lactis* for both hydrolysis and transgalactosylation reactions. Biochem. Biophys. Res. Comm. 316:738-743.
21. Knol, J., P. Scholtens, C. Kafka, J. Steenbakkers, S. Groβ, K. Helm, M. Klarczyk, H. Schopfer, H. M. Bockler, and J. Wells. 2005. Colon microflora in infants fed formula with galacto- and fructo-oligosaccharides: More like breast-fed infants. J. Pediatr. Gastroenterol. Nutr. 40:36-42.
22. Kuby, S. A. and H. A. Lardy. 1953. Purification and kinetics of b-D-galactosidase from *Escherichia coli* strain-K-12. J. Am. Chem. Soc. 75:890-896.
23. Laemmll, U. K. 1970. Cleavage of structural proteins during assembly of head of bacteriophage-T4. Nat. 227:680-685.
24. Li, P. Z., A. Anumanthan, X. G. Gao, K. Ilangovan, V. V. Suzara, N. Duzgunes, and V. Renugopalakrishnan. 2007. Expression of recombinant proteins in *Pichia pastoris*. Appl. Biochem. Biotechnol. 142:105-124.
25. Neri, D. F. M., V. M. Balcão, R. S. Costa, I. C. A. P. Rocha, E. M. F. C. Ferrera, D. P. M. Torres, L. R. M. Rodrigues, L. B. Carvalho, and J. A. Teixeira. 2009. Galacto-oligosaccharides production during lactose hydrolysis by free *Aspergillus oryzae* b-galactosidase and immobilized on magnetic polysiloxane-polyvinyl alcohol. Food Chem. 115:92-99.
26. Otieno, D. O. 2010. Synthesis of b-galactooligosaccharides from lactose using microbial b-galactosidases. Compr. Rev. Food Sci. Food Saf. 9:471-482.
27. Park, A. R. and D. K. Oh. 2010. Galacto-oligosaccharide production using microbial b-galactosidase: current state and perspectives. Appl. Microbiol. Biotechnol. 85:1279-1286.
28. Phaff, H. J. and L. D. Carmo-Sousa. 1962. Four new species of yeast isolated from insect frass in bark of *Tsuga heterophylla* (Raf.) Sargent. Antonie Van Leeuwenhoek. 28:193-207.
29. Rastall, R. A. and V. Matin. 2002. Prebiotics and synbiotics: towards the next generation. Curr. Opin. Biotechnol. 13:490-496.
30. Roberfrold, M., G. R. Gibson, L. Hoyles, A. L. McCartney, R. Rastall, I. Rowland, D. Wolvers, B. Watzl, H. Szajewska, B. Stahl, F. Guarner, F. Respondek, K. Whelan, V. Coxam, M. J. Davicco, L. Leotoing, Y. Wittrant, N. M. Delzenne, P. D. Cani, A. M. Neyrinck, and A. Meheust. 2010. Prebiotic effects: metabolic and health benefits. Br. J. Nutr. 104:S1-S63.
31. Sakai, T., H. Tsuji, S. Shibata, K. Hayakawa, and K. Matsumoto. 2008. Repeated-batch production of galactooligosaccharides from lactose at high concentration by using alginate-immobilized cells of *Sporobolomyces singularis* YIT 10047. J. Gen. Appl. Microbiol. 54:285-293.
32. Sambrook J. 2001. Molecular cloning: a laboratory manual. 3rd ed. Cold Spring Harbor Laboratory Press, Cold Spring Harbor N.Y.
33. Scopes, R. 1995. The effect of temperature on enzymes used in diagnostics. Clin. Chim. Acta 237:17-23.
34. Shin, H. J., J. M. Park, and J. W. Yang. 1998. Continuous production of galacto-oligosaccharides from lactose by *Bullera singularis* b-galactosidase immobilized in chitosan beads. Process Biochem. 33:787-792.
35. Shin, H. J. and J. W. Yang. 1998. Enzymatic production of galactooligosaccharide by *Bullera singularis* b-galactosidase. J. Microbiol. Biotechnol. 8:484-489.
36. Temple, L. M., A. A. Weiss, K. E. Walker, H. J. Barnes, V. L. Christensen, D. M. Mlyamoto, C. B. Shelton, and P. E. Orndorff. 1998. *Bordetella avium* virulence measured in vivo and in vitro. Infect. Immun. 66:5244-5251.
37. Torres, D. P. M., M. D. F. Gonqalves, J. A. Teixeira, and L. R. Rodrigues. 2010. Galacto-oligosaccharides: Production, properties, applications, and significance as prebiotics. Compr. Rev. Food Sci. Food Saf. 9:438-454.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application were specifically and individually indicated to be incorporated by reference.

8. SEQUENCE LISTING

>gi|345649663|gb|JF298281.1| Synthetic construct beta-hexosyl transferase (bglA) gene, partial cds

SEQ ID NO. 1

```
ATGATGCTGCATGCTGCACTGCTAGTAGCGCTGCCATGTGTTGTTTTGGCGCGCCCGGCCGGAGCGGTTA

CTTATCCGGGAGCCATTCCTCTGTCCCTGACGAGCAATTACGAAACCCCAAGTCCGACAGCAATCCCGCT

GGAGCCAACACCGACGGCTACCGGTACAGCAGAATTAGATGCGCTGTGGAACTTAGTCGAAGCTCAGTAC

CCAGTTCAAACTGCTGCAGTGACAACTTTGGTGACAGTGCCCGATGATTATAAGTTTGAGGCAGATCCAC

CGAGTTATGCATTAGCAGGGTATGAAACAAGCGAGATTGCCGGACTGAAGTTTCCAAAGGGGTTTAAGTT

TGGTGTTGCGGGGGCAGCCATTCAAGTTGAAGGTGCAGCAAAAGCCGAAGGGCGGGGCCCAAGTACCTGG

GATTATCTGTGTCATCACTATGCCAGCACGCAGTGTAACAATTATGATCCCGATATTACAACCAACCATT

ACTACCTGTACCCATTGGACTTTGCGCGCCTGCAACACCTAGGCATTAACACTTACTCGTTTTCAATTTC

ATGGACGCGTATTTATCCATTGGGCGCAGGCTATGTTAATGAAGCAGGGTTAGCCCACTATGATGCCGTA

ATCCATAGTGCCAAGAAGTATGGTCTGGAACCAGTGGGCACCGTTTTTCACTGGGATACGCCACTGTCTC

TGATGCTGAAATACGGTGCCTGGCAAGATACTGGTGACCAAATTGTTAAGGACTTTGTTACCTATGCCAC

AACTGTGTTTAAGCGTTATGGTAATGAAGTCAAGACGTGGTTTACTTTCAATGAACCACGGGTTTTCTGT

TCACAAAATAGTGGTCTGCCATACAATCTGACGTATCCAGAAGGTATTAACAGCACCTCCGCTGTATTTC

GTTGCACCTACAATGTTCTGAAAGCTCATGGTCATGCTGTTAAAGTGTATCGGGATCTAGTTGCCTCCGG

GACCATTGCGGCAGGTGAAATCGGCTTTAAATCCGATGATAACTACCCAATCCCGGCCCGTCCAGGGAAC

GCCGATGACGAGGAATCAGCCAAGCGTCACGAGGCTTTTCGCATTGGGATTTTTGCGCAACCGGTTTATG

GTAATGGCGATTATCCAGATGTTGTTAAAGAAACTGTTGGAGATATGCTGCCGGCCCTGACGGATGAAGA

TAAAGGATACATTAAAGGTAGCGGAGATATTTTTGCGATTGACGGGTATCGTACCGATATTTCCCATGCG

GCTCTGAACGGGATCGCGAATTGTATTCGCAACCAAAGTGACCCGAATTGGCCAGTGTGTGAAGAAGGGT

CAGATCCTTTTGCTCATGTTTACCCATCCGGGTTTGCTATTGGTCAATCAGCCGATCCACTGTCTTCATG

GTTAGTCAACTCAGCCCCGTTTATCCGCGATCAACTGAAGTTTCTGACACAAACCTACCCTGCTAAGGGT

GGTATTTATTTCTCGGAATTTGGTTGGGCTGAAGACGCCGAATATGATCGTCAACTGCTGTATCAAATTA

CCTGGGATGGTCTGCGTACGCAATACCTGACGGACTATCTGAGCCAGCTGCTGTTGGCTGTGCACAAAGA

CGGGATTAATCTGCGAGGCGCGCTGACGTGGAGTTTTGTCGATAATTGGGAGTGGGGTTTAGGGATGCAA

CAGAAATTCGGATTTCAGTTTGTTAATCAATCAGATCCCGATCTGACACGCACGTTTAAACTGAGCGCTC

ACGCTTACGCCCAATTTGGGCGTAATCATCTG
```

8. SEQUENCE LISTING

>gi|345649664|gb|AEO14215.1| beta-hexosyl transferase [synthetic construct]

SEQ ID NO. 2

MMLHAALLVALPCVVLARPAGAVTYPGAIPLSLTSNYETPSPTAIPLEPTPTATGTAELDALWNLVEAQY
PVQTAAVTTLVTVPDDYKFEADPPSYALAGYETSEIAGLKFPKGFKFGVAGAAIQVEGAAKAEGRGPSTW
DYLCHHYASTQCNNYDPDITTNHYYLYPLDFARLQHLGINTYSFSISWTRIYPLGAGYVNEAGLAHYDAV
IHSAKKYGLEPVGTVFHWDTPLSLMLKYGAWQDTGDQIVKDFVTYATTVFKRYGNEVKTWFTFNEPRVFC
SQNSGLPYNLTYPEGINSTSAVFRCTYNVLKAHGHAVKVYRDLVASGTIAAGEIGFKSDDNYPIPARPGN
ADDEESAKRHEAFRIGIFAQPVYGNGDYPDVVKETVGDMLPALTDEDKGYIKGSGDIFAIDGYRTDISHA
ALNGIANCIRNQSDPNWPVCEEGSDPFAHVYPSGFAIGQSADPLSSWLVNSAPFIRDQLKFLTQTYPAKG
GIYFSEFGWAEDAEYDRQLLYQITWDGLRTQYLTDYLSQLLLAVHKDGINLRGALTWSFVDNWEWGLGMQ
QKFGFQFVNQSDPDLTRTFKLSAHAYAQFGRNHL

FP#1 aMF-6XHIS-TEV(Q/M)-rBHT (XhoI-NotI)

SEQ ID NO. 3

ATGAGATTTCCTTCAATTTTTACTGCAGTTTTATTCGCAGCATCCTCCGCATTAGCTGCT
CCAGTCAACACTACAACAGAAGATGAAACGGCACAAATTCCGGCTGAAGCTGTCATCGGT
TACTCAGATTTAGAAGGGGATTTCGATGTTGCTGTTTTGCCATTTTCCAACAGCACAAAT
AACGGGTTATTGTTTATAAATACTACTATTGCCAGCATTGCTGCTAAAGAAGAAGGGGTA
TCTCTCGAGAAAAGAGAGGCTGAAGCT CACCACCACCACCACCACGAAAACCTGTATTTT
CAGATGATGCTGCATGCTGCACTGCTAGTAGCGCTGCCATGTGTTGTTTTGGCGCGCCCG
GCCGGAGCGGTTACTTATCCGGGAGCCATTCCTCTGTCCCTGACGAGCAATTACGAAACC
CCAAGTCCGACAGCAATCCCGCTGGAGCCAACACCGACGGCTACCGGTACAGCAGAATTA
GATGCGCTGTGGAACTTAGTCGAAGCTCAGTACCCAGTTCAAACTGCTGCAGTGACAACT
TTGGTGACAGTGCCCGATGATTATAAGTTTGAGGCAGATCCACCGAGTTATGCATTAGCA
GGGTATGAAACAAGCGAGATTGCCGGACTGAAGTTTCCAAAGGGGTTTAAGTTTGGTGTT
GCGGGGGCAGCCATTCAAGTTGAAGGTGCAGCAAAAGCCGAAGGGCGGGGCCCAAGTACC
TGGGATTATCTGTGTCATCACTATGCCAGCACGCAGTGTAACAATTATGATCCCGATATT
ACAACCAACCATTACTACCTGTACCCATTGGACTTTGCGCGCCTGCAACACCTAGGCATT
AACACTTACTCGTTTTCAATTTCATGGACGCGTATTTATCCATTGGGCGCAGGCTATGTT
AATGAAGCAGGGTTAGCCCACTATGATGCCGTAATCCATAGTGCCAAGAAGTATGGTCTG
GAACCAGTGGGCACCGTTTTTCACTGGGATACGCCACTGTCTCTGATGCTGAAATACGGT
GCCTGGCAAGATACTGGTGACCAAATTGTTAAGGACTTTGTTACCTATGCCACAACTGTG
TTTAAGCGTTATGGTAATGAAGTCAAGACGTGGTTTACTTTCAATGAACCACGGGTTTTC
TGTTCACAAAATAGTGGTCTGCCATACAATCTGACGTATCCAGAAGGTATTAACAGCACC
TCCGCTGTATTTCGTTGCACCTACAATGTTCTGAAAGCTCATGGTCATGCTGTTAAAGTG
TATCGGGATCTAGTTGCCTCCGGGACCATTGCGGCAGGTGAAATCGGCTTTAAATCCGAT
GATAACTACCCAATCCCGGCCCGTCCAGGGAACGCCGATGACGAGGAATCAGCCAAGCGT
CACGAGGCTTTTCGCATTGGGATTTTTGCGCAACCGGTTTATGGTAATGGCGATTATCCA
GATGTTGTTAAAGAAACTGTTGGAGATATGCTGCCGGCCCTGACGGATGAAGATAAAGGA
TACATTAAAGGTAGCGGAGATATTTTTGCGATTGACGGGTATCGTACCGATATTTCCCAT
GCGGCTCTGAACGGGATCGCGAATTGTATTCGCAACCAAAGTGACCCGAATTGGCCAGTG

8. SEQUENCE LISTING

TGTGAAGAAGGGTCAGATCCTTTTGCTCATGTTTACCCATCCGGGTTTGCTATTGGTCAA

TCAGCCGATCCACTGTCTTCATGGTTAGTCAACTCAGCCCCGTTTATCCGCGATCAACTG

AAGTTTCTGACACAAACCTACCCTGCTAAGGGTGGTATTTATTTCTCGGAATTTGGTTGG

GCTGAAGACGCCGAATATGATCGTCAACTGCTGTATCAAATTACCTGGGATGGTCTGCGT

ACGCAATACCTGACGGACTATCTGAGCCAGCTGCTGTTGGCTGTGCACAAAGACGGGATT

AATCTGCGAGGCGCGCTGACGTGGAGTTTTGTCGATAATTGGGAGTGGGGTTTAGGGATG

CAACAGAAATTCGGATTTCAGTTTGTTAATCAATCAGATCCCGATCTGACACGCACGTTT

AAACTGAGCGCTCACGCTTACGCCCAATTTGGGCGTAATCATCTGTAA

FP#1 aMF-6XHIS-TEV(Q/M)-rBHT

SEQ ID NO. 4

MRFPSIFTAVLFAASSALAAPVNTTTEDETAQIPAEAVIGYSDLEGDFDVAVLPFSNSTN

NGLLFINTTIASIAAKEEGVSLEKREAEA HHHHHHENLYFQMMLHAALLVALPCVVLARP

AGAVTYPGAIPLSLTSNYETPSPTAIPLEPTPTATGTAELDALWNLVEAQYPVQTAAVTT

LVTVPDDYKFEADPPSYALAGYETSEIAGLKFPKGFKFGVAGAAIQVEGAAKAEGRGPST

WDYLCHHYASTQCNNYDPDITTNHYYLYPLDFARLQHLGINTYSFSISWTRIYPLGAGYV

NEAGLAHYDAVIHSAKKYGLEPVGTVFHWDTPLSLMLKYGAWQDTGDQIVKDFVTYATTV

FKRYGNEVKTWFTFNEPRVFCSQNSGLPYNLTYPEGINSTSAVFRCTYNVLKAHGHAVKV

YRDLVASGTIAAGEIGFKSDDNYPIPARPGNADDEESAKRHEAFRIGIFAQPVYGNGDYP

DVVKETVGDMLPALTDEDKGYIKGSGDIFAIDGYRTDISHAALNGIANCIRNQSDPNWPV

CEEGSDPFAHVYPSGFAIGQSADPLSSWLVNSAPFIRDQLKFLTQTYPAKGGIYFSEFGW

AEDAEYDRQLLYQITWDGLRTQYLTDYLSQLLLAVHKDGINLRGALTWSFVDNWEWGLGM

QQKFGFQFVNQSDPDLTRTFKLSAHAYAQFGRNHL

FP#2 aMF-6XHIS-TEV(Q/M)-aMF-rBHT-6XHIS (XhoI-NotI)

SEQ ID NO. 5

ATGAGATTTCCTTCAATTTTTACTGCAGTTTTATTCGCAGCATCCTCCGCATTAGCTGCT

CCAGTCAACACTACAACAGAAGATGAAACGGCACAAATTCCGGCTGAAGCTGTCATCGGT

TACTCAGATTTAGAAGGGGATTTCGATGTTGCTGTTTTGCCATTTTCCAACAGCACAAAT

AACGGGTTATTGTTTATAAATACTACTATTGCCAGCATTGCTGCTAAAGAAGAAGGGGTA

TCTCTCGAGAAAAGAGAGGCTGAAGCT CACCACCACCACCACCACGAAAACCTGTATTTT

CAGATGATGCTGCATGCTGCACTGCTAGTAGCGCTGCCATGTGTTGTTTTGGCGCGCCCG

GCCGGAGCGGTTACTTATCCGGGAGCCATTCCTCTGTCCCTGACGAGCAATTACGAAACC

CCAAGTCCGACAGCAATCCCGCTGGAGCCAACACCGACGGCTACCGGTACAGCAGAATTA

GATGCGCTGTGGAACTTAGTCGAAGCTCAGTACCCAGTTCAAACTGCTGCAGTGACAACT

TTGGTGACAGTGCCCGATGATTATAAGTTTGAGGCAGATCCACCGAGTTATGCATTAGCA

GGGTATGAAACAAGCGAGATTGCCGGACTGAAGTTTCCAAAGGGGTTTAAGTTTGGTGTT

GCGGGGGCAGCCATTCAAGTTGAAGGTGCAGCAAAAGCCGAAGGGCGGGGCCCAAGTACC

TGGGATTATCTGTGTCATCACTATGCCAGCACGCAGTGTAACAATTATGATCCCGATATT

ACAACCAACCATTACTACCTGTACCCATTGGACTTTGCGCGCCTGCAACACCTAGGCATT

AACACTTACTCGTTTTCAATTTCATGGACGCGTATTTATCCATTGGGCGCAGGCTATGTT

AATGAAGCAGGGTTAGCCCACTATGATGCCGTAATCCATAGTGCCAAGAAGTATGGTCTG

GAACCAGTGGGCACCGTTTTTCACTGGGATACGCCACTGTCTCTGATGCTGAAATACGGT

GCCTGGCAAGATACTGGTGACCAAATTGTTAAGGACTTTGTTACCTATGCCACAACTGTG
TTTAAGCGTTATGGTAATGAAGTCAAGACGTGGTTTACTTTCAATGAACCACGGGTTTTC
TGTTCACAAAATAGTGGTCTGCCATACAATCTGACGTATCCAGAAGGTATTAACAGCACC
TCCGCTGTATTTCGTTGCACCTACAATGTTCTGAAAGCTCATGGTCATGCTGTTAAAGTG
TATCGGGATCTAGTTGCCTCCGGGACCATTGCGGCAGGTGAAATCGGCTTTAAATCCGAT
GATAACTACCCAATCCCGGCCCGTCCAGGGAACGCCGATGACGAGGAATCAGCCAAGCGT
CACGAGGCTTTTCGCATTGGGATTTTTGCGCAACCGGTTTATGGTAATGGCGATTATCCA
GATGTTGTTAAAGAAACTGTTGGAGATATGCTGCCGGCCCTGACGGATGAAGATAAAGGA
TACATTAAAGGTAGCGGAGATATTTTTGCGATTGACGGGTATCGTACCGATATTTCCCAT
GCGGCTCTGAACGGGATCGCGAATTGTATTCGCAACCAAAGTGACCCGAATTGGCCAGTG
TGTGAAGAAGGGTCAGATCCTTTTGCTCATGTTTACCCATCCGGGTTTGCTATTGGTCAA
TCAGCCGATCCACTGTCTTCATGGTTAGTCAACTCAGCCCCGTTTATCCGCGATCAACTG
AAGTTTCTGACACAAACCTACCCTGCTAAGGGTGGTATTTATTTCTCGGAATTTGGTTGG
GCTGAAGACGCCGAATATGATCGTCAACTGCTGTATCAAATTACCTGGGATGGTCTGCGT
ACGCAATACCTGACGGACTATCTGAGCCAGCTGCTGTTGGCTGTGCACAAAGACGGGATT
AATCTGCGAGGCGCGCTGACGTGGAGTTTTGTCGATAATTGGGAGTGGGGTTTAGGGATG
CAACAGAAATTCGGATTTCAGTTTGTTAATCAATCAGATCCCGATCTGACACGCACGTTT
AAACTGAGCGCTCACGCTTACGCCCAATTTGGGCGTAATCATCTGCACCACCACCACCAC
CACTAA

FP#2 aMF-<u>6XHIS-TEV(Q/M)</u>-aMF-<u>rBHT-6XHIS</u>  SEQ ID NO. 6
MRFPSIFTAVLFAASSALAAPVNTTTEDETAQIPAEAVIGYSDLEGDFDVAVLPFSNSTN
NGLLFINTTIASIAAKEEGVSLEKREAEA HHHHHHENLYFQMMLHAALLVALPCVVLARP
AGAVTYPGAIPLSLTSNYETPSPTAIPLEPTPTATGTAELDALWNLVEAQYPVQTAAVTT
LVTVPDDYKFEADPPSYALAGYETSEIAGLKFPKGFKFGVAGAAIQVEGAAKAEGRGPST
WDYLCHHYASTQCNNYDPDITTNHYYLYPLDFARLQHLGINTYSFSISWTRIYPLGAGYV
NEAGLAHYDAVIHSAKKYGLEPVGTVFHWDTPLSLMLKYGAWQDTGDQIVKDFVTYATTV
FKRYGNEVKTWFTFNEPRVFCSQNSGLPYNLTYPEGINSTSAVFRCTYNVLKAHGHAVKV
YRDLVASGTIAAGEIGFKSDDNYPIPARPGNADDEESAKRHEAFRIGIFAQPVYGNGDYP
DVVKETVGDMLPALTDEDKGYIKGSGDIFAIDGYRTDISHAALNGIANCIRNQSDPNWPV
CEEGSDPFAHVYPSGFAIGQSADPLSSWLVNSAPFIRDQLKFLTQTYPAKGGIYFSEFGW
AEDAEYDRQLLYQITWDGLRTQYLTDYLSQLLLAVHKDGINLRGALTWSFVDNWEWGLGM
QQKFGFQFVNQSDPDLTRTFKLSAHAYAQFGRNHLHHHHHH

FP#3 aMF-<u>rBHT-6XHIS (XhoI-NotI)</u>  SEQ ID NO. 7
ATGAGATTTCCTTCAATTTTTACTGCAGTTTTATTCGCAGCATCCTCCGCATTAGCTGCT
CCAGTCAACACTACAACAGAAGATGAAACGGCACAAATTCCGGCTGAAGCTGTCATCGGT
TACTCAGATTTAGAAGGGGATTTCGATGTTGCTGTTTTGCCATTTTCCAACAGCACAAAT
AACGGGTTATTGTTTATAAATACTACTATTGCCAGCATTGCTGCTAAAGAAGAAGGGGTA
TCTCTCGAGAAAAGAGAGGCTGAAGCT ATGATGCTGCATGCTGCACTGCTAGTAGCGCTG

8. SEQUENCE LISTING

CCATGTGTTGTTTTGGCGCGCCCGGCCGGAGCGGTTACTTATCCGGGAGCCATTCCTCTG
TCCCTGACGAGCAATTACGAAACCCCAAGTCCGACAGCAATCCCGCTGGAGCCAACACCG
ACGGCTACCGGTACAGCAGAATTAGATGCGCTGTGGAACTTAGTCGAAGCTCAGTACCCA
GTTCAAACTGCTGCAGTGACAACTTTGGTGACAGTGCCCGATGATTATAAGTTTGAGGCA
GATCCACCGAGTTATGCATTAGCAGGGTATGAAACAAGCGAGATTGCCGGACTGAAGTTT
CCAAAGGGGTTTAAGTTTGGTGTTGCGGGGGCAGCCATTCAAGTTGAAGGTGCAGCAAAA
GCCGAAGGGCGGGGCCCAAGTACCTGGGATTATCTGTGTCATCACTATGCCAGCACGCAG
TGTAACAATTATGATCCCGATATTACAACCAACCATTACTACCTGTACCCATTGGACTTT
GCGCGCCTGCAACACCTAGGCATTAACACTTACTCGTTTTCAATTTCATGGACGCGTATT
TATCCATTGGGCGCAGGCTATGTTAATGAAGCAGGGTTAGCCCACTATGATGCCGTAATC
CATAGTGCCAAGAAGTATGGTCTGGAACCAGTGGGCACCGTTTTTCACTGGGATACGCCA
CTGTCTCTGATGCTGAAATACGGTGCCTGGCAAGATACTGGTGACCAAATTGTTAAGGAC
TTTGTTACCTATGCCACAACTGTGTTTAAGCGTTATGGTAATGAAGTCAAGACGTGGTTT
ACTTTCAATGAACCACGGGTTTTCTGTTCACAAAATAGTGGTCTGCCATACAATCTGACG
TATCCAGAAGGTATTAACAGCACCTCCGCTGTATTTCGTTGCACCTACAATGTTCTGAAA
GCTCATGGTCATGCTGTTAAAGTGTATCGGGATCTAGTTGCCTCCGGGACCATTGCGGCA
GGTGAAATCGGCTTTAAATCCGATGATAACTACCCAATCCCGGCCCGTCCAGGGAACGCC
GATGACGAGGAATCAGCCAAGCGTCACGAGGCTTTTCGCATTGGGATTTTTGCGCAACCG
GTTTATGGTAATGGCGATTATCCAGATGTTGTTAAAGAAACTGTTGGAGATATGCTGCCG
GCCCTGACGGATGAAGATAAAGGATACATTAAAGGTAGCGGAGATATTTTTGCGATTGAC
GGGTATCGTACCGATATTTCCCATGCGGCTCTGAACGGGATCGCGAATTGTATTCGCAAC
CAAAGTGACCCGAATTGGCCAGTGTGTGAAGAAGGGTCAGATCCTTTTGCTCATGTTTAC
CCATCCGGGTTTGCTATTGGTCAATCAGCCGATCCACTGTCTTCATGGTTAGTCAACTCA
GCCCCGTTTATCCGCGATCAACTGAAGTTTCTGACACAAACCTACCCTGCTAAGGGTGGT
ATTTATTTCTCGGAATTTGGTTGGGCTGAAGACGCCGAATATGATCGTCAACTGCTGTAT
CAAATTACCTGGGATGGTCTGCGTACGCAATACCTGACGGACTATCTGAGCCAGCTGCTG
TTGGCTGTGCACAAAGACGGGATTAATCTGCGAGGCGCGCTGACGTGGAGTTTTGTCGAT
AATTGGGAGTGGGGTTTAGGGATGCAACAGAAATTCGGATTTCAGTTTGTTAATCAATCA
GATCCCGATCTGACACGCACGTTTAAACTGAGCGCTCACGCTTACGCCCAATTTGGGCGT
AATCATCTGCACCACCACCACCACCACTAA

FP#3 aMF-<u>rBHT</u>-6XHIS

SEQ ID NO. 8

MRFPSIFTAVLFAASSALAAPVNTTTEDETAQIPAEAVIGYSDLEGDFDVAVLPFSNSTN
NGLLFINTTIASIAAKEEGVSLEKREAEA <u>MMLHAALLVALPCVVLARPAGAVTYPGAIPL</u>
<u>SLTSNYETPSPTAIPLEPTPTATGTAELDALWNLVEAQYPVQTAAVTTLVTVPDDYKFEA</u>
<u>DPPSYALAGYETSEIAGLKFPKGFKFGVAGAAIQVEGAAKAEGRGPSTWDYLCHHYASTQ</u>
<u>CNNYDPDITTNHYYLYPLDFARLQHLGINTYSFSISWTRIYPLGAGYVNEAGLAHYDAVI</u>
<u>HSAKKYGLEPVGTVFHWDTPLSLMLKYGAWQDTGDQIVKDFVTYATTVFKRYGNEVKTWF</u>
<u>TFNEPRVFCSQNSGLPYNLTYPEGINSTSAVFRCTYNVLKAHGHAVKVYRDLVASGTIAA</u>
<u>GEIGFKSDDNYPIPARPGNADDEESAKRHEAFRIGIFAQPVYGNGDYPDVVKETVGDMLP</u>

ALTDEDKGYIKGSGDIFAIDGYRTDISHAALNGIANCIRNQSDPNWPVCEEGSDPFAHVY

PSGFAIGQSADPLSSWLVNSAPFIRDQLKFLTQTYPAKGGIYFSEFGWAEDAEYDRQLLY

QITWDGLRTQYLTDYLSQLLLAVHKDGINLRGALTWSFVDNWEWGLGMQQKFGFQFVNQS

DPDLTRTFKLSAHAYAQFGRNHLHHHHHH

FP#4 aMF-rBHT (XhoI-NotI)

SEQ ID NO. 9

ATGAGATTTCCTTCAATTTTTACTGCAGTTTTATTCGCAGCATCCTCCGCATTAGCTGCT

CCAGTCAACACTACAACAGAAGATGAAACGGCACAAATTCCGGCTGAAGCTGTCATCGGT

TACTCAGATTTAGAAGGGGATTTCGATGTTGCTGTTTTGCCATTTTCCAACAGCACAAAT

AACGGGTTATTGTTTATAAATACTACTATTGCCAGCATTGCTGCTAAAGAAGAAGGGGTA

TCTCTCGAGAAAAGAGAGGCTGAAGCT ATGATGCTGCATGCTGCACTGCTAGTAGCGCTG

CCATGTGTTGTTTTGGCGCGCCCGGCCGGAGCGGTTACTTATCCGGGAGCCATTCCTCTG

TCCCTGACGAGCAATTACGAAACCCCAAGTCCGACAGCAATCCCGCTGGAGCCAACACCG

ACGGCTACCGGTACAGCAGAATTAGATGCGCTGTGGAACTTAGTCGAAGCTCAGTACCCA

GTTCAAACTGCTGCAGTGACAACTTTGGTGACAGTGCCCGATGATTATAAGTTTGAGGCA

GATCCACCGAGTTATGCATTAGCAGGGTATGAAACAAGCGAGATTGCCGGACTGAAGTTT

CCAAAGGGGTTTAAGTTTGGTGTTGCGGGGGCAGCCATTCAAGTTGAAGGTGCAGCAAAA

GCCGAAGGGCGGGGCCCAAGTACCTGGGATTATCTGTGTCATCACTATGCCAGCACGCAG

TGTAACAATTATGATCCGATATTACAACCAACCATTACTACCTGTACCCATTGGACTTT

GCGCGCCTGCAACACCTAGGCATTAACACTTACTCGTTTTCAATTTCATGGACGCGTATT

TATCCATTGGGCGCAGGCTATGTTAATGAAGCAGGGTTAGCCCACTATGATGCCGTAATC

CATAGTGCCAAGAAGTATGGTCTGGAACCAGTGGGCACCGTTTTTCACTGGGATACGCCA

CTGTCTCTGATGCTGAAATACGGTGCCTGGCAAGATACTGGTGACCAAATTGTTAAGGAC

TTTGTTACCTATGCCACAACTGTGTTTAAGCGTTATGGTAATGAAGTCAAGACGTGGTTT

ACTTTCAATGAACCACGGGTTTTCTGTTCACAAAATAGTGGTCTGCCATACAATCTGACG

TATCCAGAAGGTATTAACAGCACCTCCGCTGTATTTCGTTGCACCTACAATGTTCTGAAA

GCTCATGGTCATGCTGTTAAAGTGTATCGGGATCTAGTTGCCTCCGGGACCATTGCGGCA

GGTGAAATCGGCTTTAAATCCGATGATAACTACCCAATCCCGGCCCGTCCAGGGAACGCC

GATGACGAGGAATCAGCCAAGCGTCACGAGGCTTTTCGCATTGGGATTTTTGCGCAACCG

GTTTATGGTAATGGCGATTATCCAGATGTTGTTAAAGAAACTGTTGGAGATATGCTGCCG

GCCCTGACGGATGAAGATAAAGGATACATTAAAGGTAGCGGAGATATTTTTGCGATTGAC

GGGTATCGTACCGATATTTCCCATGCGGCTCTGAACGGGATCGCGAATTGTATTCGCAAC

CAAAGTGACCCGAATTGGCCAGTGTGTGAAGAAGGGTCAGATCCTTTTGCTCATGTTTAC

CCATCCGGGTTTGCTATTGGTCAATCAGCCGATCCACTGTCTTCATGGTTAGTCAACTCA

GCCCCGTTTATCCGCGATCAACTGAAGTTTCTGACACAAACCTACCCTGCTAAGGGTGGT

ATTTATTTCTCGGAATTTGGTTGGGCTGAAGACGCCGAATATGATCGTCAACTGCTGTAT

CAAATTACCTGGGATGGTCTGCGTACGCAATACCTGACGGACTATCTGAGCCAGCTGCTG

TTGGCTGTGCACAAAGACGGGATTAATCTGCGAGGCGCGCTGACGTGGAGTTTTGTCGAT

AATTGGGAGTGGGGTTTAGGGATGCAACAGAAATTCGGATTTCAGTTTGTTAATCAATCA

8. SEQUENCE LISTING

```
GATCCCGATCTGACACGCACGTTTAAACTGAGCGCTCACGCTTACGCCCAATTTGGGCGT
AATCATCTGTAA
```

FP#4 aMF-rBHT                                                    SEQ ID NO. 10

```
MRFPSIFTAVLFAASSALAAPVNTTTEDETAQIPAEAVIGYSDLEGDFDVAVLPFSNSTN
NGLLFINTTIASIAAKEEGVSLEKREAEA MMLHAALLVALPCVVLARPAGAVTYPGAIPL
SLTSNYETPSPTAIPLEPTPTATGTAELDALWNLVEAQYPVQTAAVTTLVTVPDDYKFEA
DPPSYALAGYETSEIAGLKFPKGFKFGVAGAAIQVEGAAKAEGRGPSTWDYLCHHYASTQ
CNNYDPDITTNHYYLYPLDFARLQHLGINTYSFSISWTRIYPLGAGYVNEAGLAHYDAVI
HSAKKYGLEPVGTVFHWDTPLSLMLKYGAWQDTGDQIVKDFVTYATTVFKRYGNEVKTWF
TFNEPRVFCSQNSGLPYNLTYPEGINSTSAVFRCTYNVLKAHGHAVKVYRDLVASGTIAA
GEIGFKSDDNYPIPARPGNADDEESAKRHEAFRIGIFAQPVYGNGDYPDVVKETVGDMLP
ALTDEDKGYIKGSGDIFAIDGYRTDISHAALNGIANCIRNQSDPNWPVCEEGSDPFAHVY
PSGFAIGQSADPLSSWLVNSAPFIRDQLKFLTQTYPAKGGIYFSEFGWAEDAEYDRQLLY
QITWDGLRTQYLTDYLSQLLLAVHKDGINLRGALTWSFVDNWEWGLGMQQKFGFQFVNQS
DPDLTRTFKLSAHAYAQFGRNHL
```

FP#5 aMF-rBHT(Δ1-22)-6XHIS (XhoI-NotI)                          SEQ ID NO. 11

```
ATGAGATTTCCTTCAATTTTTACTGCAGTTTTATTCGCAGCATCCTCCGCATTAGCTGCT
CCAGTCAACACTACAACAGAAGATGAAACGGCACAAATTCCGGCTGAAGCTGTCATCGGT
TACTCAGATTTAGAAGGGGATTTCGATGTTGCTGTTTTGCCATTTTCCAACAGCACAAAT
AACGGGTTATTGTTTATAAATACTACTATTGCCAGCATTGCTGCTAAAGAAGAAGGGGTA
TCTCTCGAGAAAAGAGAGGCTGAAGCT GTTACTTATCCGGGAGCCATTCCTCTGTCCCTG
ACGAGCAATTACGAAACCCAAGTCCGACAGCAATCCCGCTGGAGCCAACACCGACGGCT
ACCGGTACAGCAGAATTAGATGCGCTGTGGAACTTAGTCGAAGCTCAGTACCCAGTTCAA
ACTGCTGCAGTGACAACTTTGGTGACAGTGCCCGATGATTATAAGTTTGAGGCAGATCCA
CCGAGTTATGCATTAGCAGGGTATGAAACAAGCGAGATTGCCGGACTGAAGTTTCCAAAG
GGGTTTAAGTTTGGTGTTGCGGGGGCAGCCATTCAAGTTGAAGGTGCAGCAAAAGCCGAA
GGGCGGGGCCCAAGTACCTGGGATTATCTGTGTCATCACTATGCCAGCACGCAGTGTAAC
AATTATGATCCCGATATTACAACCAACCATTACTACCTGTACCCATTGGACTTTGCGCGC
CTGCAACACCTAGGCATTAACACTTACTCGTTTTCAATTTCATGGACGCGTATTTATCCA
TTGGGCGCAGGCTATGTTAATGAAGCAGGGTTAGCCCACTATGATGCCGTAATCCATAGT
GCCAAGAAGTATGGTCTGGAACCAGTGGGCACCGTTTTTCACTGGGATACGCCACTGTCT
CTGATGCTGAAATACGGTGCCTGGCAAGATACTGGTGACCAAATTGTTAAGGACTTTGTT
ACCTATGCCACAACTGTGTTTAAGCGTTATGGTAATGAAGTCAAGACGTGGTTTACTTTC
AATGAACCACGGGTTTTCTGTTCACAAAATAGTGGTCTGCCATACAATCTGACGTATCCA
GAAGGTATTAACAGCACCTCCGCTGTATTTCGTTGCACCTACAATGTTCTGAAAGCTCAT
GGTCATGCTGTTAAAGTGTATCGGGATCTAGTTGCCTCCGGGACCATTGCGGCAGGTGAA
ATCGGCTTTAAATCCGATGATAACTACCCAATCCCGGCCCGTCCAGGGAACGCCGATGAC
GAGGAATCAGCCAAGCGTCACGAGGCTTTTCGCATTGGGATTTTTGCGCAACCGGTTTAT
GGTAATGGCGATTATCCAGATGTTGTTAAAGAAACTGTTGGAGATATGCTGCCGGCCCTG
```

8. SEQUENCE LISTING

ACGGATGAAGATAAAGGATACATTAAAGGTAGCGGAGATATTTTTGCGATTGACGGGTAT

CGTACCGATATTTCCCATGCGGCTCTGAACGGGATCGCGAATTGTATTCGCAACCAAAGT

GACCCGAATTGGCCAGTGTGTGAAGAAGGGTCAGATCCTTTTGCTCATGTTTACCCATCC

GGGTTTGCTATTGGTCAATCAGCCGATCCACTGTCTTCATGGTTAGTCAACTCAGCCCCG

TTTATCCGCGATCAACTGAAGTTTCTGACACAAACCTACCCTGCTAAGGGTGGTATTTAT

TTCTCGGAATTTGGTTGGGCTGAAGACGCCGAATATGATCGTCAACTGCTGTATCAAATT

ACCTGGGATGGTCTGCGTACGCAATACCTGACGGACTATCTGAGCCAGCTGCTGTTGGCT

GTGCACAAGACGGGATTAATCTGCGAGGCGCGCTGACGTGGAGTTTTGTCGATAATTGG

GAGTGGGGTTTAGGGATGCAACAGAAATTCGGATTTCAGTTTGTTAATCAATCAGATCCC

GATCTGACACGCACGTTTAAACTGAGCGCTCACGCTTACGCCCAATTTGGGCGTAATCAT

CTGCACCACCACCACCACTAA

FP#5 aMF-rBHT(Δ1-22)-6XHIS                                      SEQ ID NO. 12

MRFPSIFTAVLFAASSALAAPVNTTTEDETAQIPAEAVIGYSDLEGDFDVAVLPFSNSTN

NGLLFINTTIASIAAKEEGVSLEKREAEA VTYPGAIPLSLTSNYETPSPTAIPLEPTPTA

TGTAELDALWNLVEAQYPVQTAAVTTLVTVPDDYKFEADPPSYALAGYETSEIAGLKFPK

GFKFGVAGAAIQVEGAAKAEGRGPSTWDYLCHHYASTQCNNYDPDITTNHYYLYPLDFAR

LQHLGINTYSFSISWTRIYPLGAGYVNEAGLAHYDAVIHSAKKYGLEPVGTVFHWDTPLS

LMLKYGAWQDTGDQIVKDFVTYATTVFKRYGNEVKTWFTFNEPRVFCSQNSGLPYNLTYP

EGINSTSAVFRCTYNVLKAHGHAVKVYRDLVASGTIAAGEIGFKSDDNYPIPARPGNADD

EESAKRHEAFRIGIFAQPVYGNGDYPDVVKETVGDMLPALTDEDKGYIKGSGDIFAIDGY

RTDISHAALNGIANCIRNQSDPNWPVCEEGSDPFAHVYPSGFAIGQSADPLSSWLVNSAP

FIRDQLKFLTQTYPAKGGIYFSEFGWAEDAEYDRQLLYQITWDGLRTQYLTDYLSQLLLA

VHKDGINLRGALTWSFVDNWEWGLGMQQKFGFQFVNQSDPDLTRTFKLSAHAYAQFGRNH

LHHHHHH

FP#6 aMF-rBHT(Δ1-22) (XhoI-NotI)                                 SEQ ID NO. 13

ATGAGATTTCCTTCAATTTTTACTGCAGTTTTATTCGCAGCATCCTCCGCATTAGCTGCT

CCAGTCAACACTACAACAGAAGATGAAACGGCACAAATTCCGGCTGAAGCTGTCATCGGT

TACTCAGATTTAGAAGGGGATTTCGATGTTGCTGTTTTGCCATTTTCCAACAGCACAAAT

AACGGGTTATTGTTTATAAATACTACTATTGCCAGCATTGCTGCTAAAGAAGAAGGGGTA

TCTCTCGAGAAAAGAGAGGCTGAAGCT GTTACTTATCCGGGAGCCATTCCTCTGTCCCTG

ACGAGCAATTACGAAACCCCAAGTCCGACAGCAATCCCGCTGGAGCCAACACCGACGGCT

ACCGGTACAGCAGAATTAGATGCGCTGTGGAACTTAGTCGAAGCTCAGTACCCAGTTCAA

ACTGCTGCAGTGACAACTTTGGTGACAGTGCCCGATGATTATAAGTTTGAGGCAGATCCA

CCGAGTTATGCATTAGCAGGGTATGAAACAAGCGAGATTGCCGGACTGAAGTTTCCAAAG

GGGTTTAAGTTTGGTGTTGCGGGGGCAGCCATTCAAGTTGAAGGTGCAGCAAAAGCCGAA

GGGCGGGGCCCAAGTACCTGGGATTATCTGTGTCATCACTATGCCAGCACGCAGTGTAAC

AATTATGATCCCGATATTACAACCAACCATTACTACCTGTACCCATTGGACTTTGCGCGC

CTGCAACACCTAGGCATTAACACTTACTCGTTTTCAATTTCATGGACGCGTATTTATCCA

8. SEQUENCE LISTING

TTGGGCGCAGGCTATGTTAATGAAGCAGGGTTAGCCCACTATGATGCCGTAATCCATAGT
GCCAAGAAGTATGGTCTGGAACCAGTGGGCACCGTTTTTCACTGGGATACGCCACTGTCT
CTGATGCTGAAATACGGTGCCTGGCAAGATACTGGTGACCAAATTGTTAAGGACTTTGTT
ACCTATGCCACAACTGTGTTTAAGCGTTATGGTAATGAAGTCAAGACGTGGTTTACTTTC
AATGAACCACGGGTTTTCTGTTCACAAAATAGTGGTCTGCCATACAATCTGACGTATCCA
GAAGGTATTAACAGCACCTCCGCTGTATTTCGTTGCACCTACAATGTTCTGAAAGCTCAT
GGTCATGCTGTTAAAGTGTATCGGGATCTAGTTGCCTCCGGGACCATTGCGGCAGGTGAA
ATCGGCTTTAAATCCGATGATAACTACCCAATCCCGGCCCGTCCAGGGAACGCCGATGAC
GAGGAATCAGCCAAGCGTCACGAGGCTTTTCGCATTGGGATTTTTGCGCAACCGGTTTAT
GGTAATGGCGATTATCCAGATGTTGTTAAAGAAACTGTTGGAGATATGCTGCCGGCCCTG
ACGGATGAAGATAAAGGATACATTAAAGGTAGCGGAGATATTTTTGCGATTGACGGGTAT
CGTACCGATATTTCCCATGCGGCTCTGAACGGGATCGCGAATTGTATTCGCAACCAAAGT
GACCCGAATTGGCCAGTGTGTGAAGAAGGGTCAGATCCTTTTGCTCATGTTTACCCATCC
GGGTTTGCTATTGGTCAATCAGCCGATCCACTGTCTTCATGGTTAGTCAACTCAGCCCCG
TTTATCCGCGATCAACTGAAGTTTCTGACACAAACCTACCCTGCTAAGGGTGGTATTTAT
TTCTCGGAATTTGGTTGGGCTGAAGACGCCGAATATGATCGTCAACTGCTGTATCAAATT
ACCTGGGATGGTCTGCGTACGCAATACCTGACGGACTATCTGAGCCAGCTGCTGTTGGCT
GTGCACAAAGACGGGATTAATCTGCGAGGCGCGCTGACGTGGAGTTTTGTCGATAATTGG
GAGTGGGGTTTAGGGATGCAACAGAAATTCGGATTTCAGTTTGTTAATCAATCAGATCCC
GATCTGACACGCACGTTTAAACTGAGCGCTCACGCTTACGCCCAATTTGGGCGTAATCAT
CTGTAA

FP#6 aMF-rBHT(Δ1-22)                                          SEQ ID NO. 14

MRFPSIFTAVLFAASSALAAPVNTTTEDETAQIPAEAVIGYSDLEGDFDVAVLPFSNSTN
NGLLFINTTIASIAAKEEGVSLEKREAEA VTYPGAIPLSLTSNYETPSPTAIPLEPTPTA
TGTAELDALWNLVEAQYPVQTAAVTTLVTVPDDYKFEADPPSYALAGYETSEIAGLKFPK
GFKFGVAGAAIQVEGAAKAEGRGPSTWDYLCHHYASTQCNNYDPDITTNHYYLYPLDFAR
LQHLGINTYSFSISWTRIYPLGAGYVNEAGLAHYDAVIHSAKKYGLEPVGTVFHWDTPLS
LMLKYGAWQDTGDQIVKDFVTYATTVFKRYGNEVKTWFTFNEPRVFCSQNSGLPYNLTYP
EGINSTSAVFRCTYNVLKAHGHAVKVYRDLVASGTIAAGEIGFKSDDNYPIPARPGNADD
EESAKRHEAFRIGIFAQPVYGNGDYPDVVKETVGDMLPALTDEDKGYIKGSGDIFAIDGY
RTDISHAALNGIANCIRNQSDPNWPVCEEGSDPFAHVYPSGFAIGQSADPLSSWLVNSAP
FIRDQLKFLTQTYPAKGGIYFSEFGWAEDAEYDRQLLYQITWDGLRTQYLTDYLSQLLLA
VHKDGINLRGALTWSFVDNWEWGLGMQQKFGFQFVNQSDPDLTRTFKLSAHAYAQFGRNH
L

FP#7 rBHT-6XHIS (BamHI-NotI)                                  Seq. ID No. 15

ATGATGCTGCATGCTGCACTGCTAGTAGCGCTGCCATGTGTTGTTTTGGCGCGCCCGGCC
GGAGCGGTTACTTATCCGGGAGCCATTCCTCTGTCCCTGACGAGCAATTACGAAACCCCA
AGTCCGACAGCAATCCCGCTGGAGCCAACACCGACGGCTACCGGTACAGCAGAATTAGAT
GCGCTGTGGAACTTAGTCGAAGCTCAGTACCCAGTTCAAACTGCTGCAGTGACAACTTTG

8. SEQUENCE LISTING

GTGACAGTGCCCGATGATTATAAGTTTGAGGCAGATCCACCGAGTTATGCATTAGCAGGG

TATGAAACAAGCGAGATTGCCGGACTGAAGTTTCCAAAGGGGTTTAAGTTTGGTGTTGCG

GGGGCAGCCATTCAAGTTGAAGGTGCAGCAAAAGCCGAAGGGCGGGGCCCAAGTACCTGG

GATTATCTGTGTCATCACTATGCCAGCACGCAGTGTAACAATTATGATCCCGATATTACA

ACCAACCATTACTACCTGTACCCATTGGACTTTGCGCGCCTGCAACACCTAGGCATTAAC

ACTTACTCGTTTTCAATTTCATGGACGCGTATTTATCCATTGGGCGCAGGCTATGTTAAT

GAAGCAGGGTTAGCCCACTATGATGCCGTAATCCATAGTGCCAAGAAGTATGGTCTGGAA

CCAGTGGGCACCGTTTTTCACTGGGATACGCCACTGTCTCTGATGCTGAAATACGGTGCC

TGGCAAGATACTGGTGACCAAATTGTTAAGGACTTTGTTACCTATGCCACAACTGTGTTT

AAGCGTTATGGTAATGAAGTCAAGACGTGGTTTACTTTCAATGAACCACGGGTTTTCTGT

TCACAAAATAGTGGTCTGCCATACAATCTGACGTATCCAGAAGGTATTAACAGCACCTCC

GCTGTATTTCGTTGCACCTACAATGTTCTGAAAGCTCATGGTCATGCTGTTAAAGTGTAT

CGGGATCTAGTTGCCTCCGGGACCATTGCGGCAGGTGAAATCGGCTTTAAATCCGATGAT

AACTACCCAATCCCGGCCCGTCCAGGGAACGCCGATGACGAGGAATCAGCCAAGCGTCAC

GAGGCTTTTCGCATTGGGATTTTTGCGCAACCGGTTTATGGTAATGGCGATTATCCAGAT

GTTGTTAAAGAAACTGTTGGAGATATGCTGCCGGCCCTGACGGATGAAGATAAAGGATAC

ATTAAAGGTAGCGGAGATATTTTTGCGATTGACGGGTATCGTACCGATATTTCCCATGCG

GCTCTGAACGGGATCGCGAATTGTATTCGCAACCAAAGTGACCCGAATTGGCCAGTGTGT

GAAGAAGGGTCAGATCCTTTTGCTCATGTTTACCCATCCGGGTTTGCTATTGGTCAATCA

GCCGATCCACTGTCTTCATGGTTAGTCAACTCAGCCCCGTTTATCCGCGATCAACTGAAG

TTTCTGACACAAACCTACCCTGCTAAGGGTGGTATTTATTTCTCGGAATTTGGTTGGGCT

GAAGACGCCGAATATGATCGTCAACTGCTGTATCAAATTACCTGGGATGGTCTGCGTACG

CAATACCTGACGGACTATCTGAGCCAGCTGCTGTTGGCTGTGCACAAAGACGGGATTAAT

CTGCGAGGCGCGCTGACGTGGAGTTTTGTCGATAATTGGGAGTGGGGTTTAGGGATGCAA

CAGAAATTCGGATTTCAGTTTGTTAATCAATCAGATCCCGATCTGACACGCACGTTTAAA

CTGAGCGCTCACGCTTACGCCCAATTTGGGCGTAATCATCTGCACCACCACCACCACCAC

TAA

FP#7 rBHT-6XHIS SEQ ID NO. 16

MMLHAALLVALPCVVLARPAGAVTYPGAIPLSLTSNYETPSPTAIPLEPTPTATGTAELD

ALWNLVEAQYPVQTAAVTTLVTVPDDYKFEADPPSYALAGYETSEIAGLKFPKGFKFGVA

GAAIQVEGAAKAEGRGPSTWDYLCHHYASTQCNNYDPDITTNHYYLYPLDFARLQHLGIN

TYSFSISWTRIYPLGAGYVNEAGLAHYDAVIHSAKKYGLEPVGTVFHWDTPLSLMLKYGA

WQDTGDQIVKDFVTYATTVFKRYGNEVKTWFTFNEPRVFCSQNSGLPYNLTYPEGINSTS

AVFRCTYNVLKAHGHAVKVYRDLVASGTIAAGEIGFKSDDNYPIPARPGNADDEESAKRH

EAFRIGIFAQPVYGNGDYPDVVKETVGDMLPALTDEDKGYIKGSGDIFAIDGYRTDISHA

ALNGIANCIRNQSDPNWPVCEEGSDPFAHVYPSGFAIGQSADPLSSWLVNSAPFIRDQLK

FLTQTYPAKGGIYFSEFGWAEDAEYDRQLLYQITWDGLRTQYLTDYLSQLLAVHKDGIN

LRGALTWSFVDNWEWGLGMQQKFGFQFVNQSDPDLTRTFKLSAHAYAQFGRNHLHHHHHH

8. SEQUENCE LISTING

FP#8 rBHT(Δ1-22)-6XHIS (BamHI-NotI)   SEQ ID NO. 17

ATGGTTACTTATCCGGGAGCCATTCCTCTGTCCCTGACGAGCAATTACGAAACCCCAAGT

CCGACAGCAATCCCGCTGGAGCCAACACCGACGGCTACCGGTACAGCAGAATTAGATGCG

CTGTGGAACTTAGTCGAAGCTCAGTACCCAGTTCAAACTGCTGCAGTGACAACTTTGGTG

ACAGTGCCCGATGATTATAAGTTTGAGGCAGATCCACCGAGTTATGCATTAGCAGGGTAT

GAAACAAGCGAGATTGCCGGACTGAAGTTTCCAAAGGGGTTTAAGTTTGGTGTTGCGGGG

GCAGCCATTCAAGTTGAAGGTGCAGCAAAAGCCGAAGGGCGGGGCCCAAGTACCTGGGAT

TATCTGTGTCATCACTATGCCAGCACGCAGTGTAACAATTATGATCCCGATATTACAACC

AACCATTACTACCTGTACCCATTGGACTTTGCGCGCCTGCAACACCTAGGCATTAACACT

TACTCGTTTTCAATTTCATGGACGCGTATTTATCCATTGGGCGCAGGCTATGTTAATGAA

GCAGGGTTAGCCCACTATGATGCCGTAATCCATAGTGCCAAGAAGTATGGTCTGGAACCA

GTGGGCACCGTTTTTCACTGGGATACGCCACTGTCTCTGATGCTGAAATACGGTGCCTGG

CAAGATACTGGTGACCAAATTGTTAAGGACTTTGTTACCTATGCCACAACTGTGTTTAAG

CGTTATGGTAATGAAGTCAAGACGTGGTTTACTTTCAATGAACCACGGGTTTTCTGTTCA

CAAAATAGTGGTCTGCCATACAATCTGACGTATCCAGAAGGTATTAACAGCACCTCCGCT

GTATTTCGTTGCACCTACAATGTTCTGAAAGCTCATGGTCATGCTGTTAAAGTGTATCGG

GATCTAGTTGCCTCCGGGACCATTGCGGCAGGTGAAATCGGCTTTAAATCCGATGATAAC

TACCCAATCCCGGCCCGTCCAGGGAACGCCGATGACGAGGAATCAGCCAAGCGTCACGAG

GCTTTTCGCATTGGGATTTTTGCGCAACCGGTTTATGGTAATGGCGATTATCCAGATGTT

GTTAAAGAAACTGTTGGAGATATGCTGCCGGCCCTGACGGATGAAGATAAAGGATACATT

AAAGGTAGCGGAGATATTTTTGCGATTGACGGGTATCGTACCGATATTTCCCATGCGGCT

CTGAACGGGATCGCGAATTGTATTCGCAACCAAAGTGACCCGAATTGGCCAGTGTGTGAA

GAAGGGTCAGATCCTTTTGCTCATGTTTACCCATCCGGGTTTGCTATTGGTCAATCAGCC

GATCCACTGTCTTCATGGTTAGTCAACTCAGCCCCGTTTATCCGCGATCAACTGAAGTTT

CTGACACAAACCTACCCTGCTAAGGGTGGTATTTATTTCTCGGAATTTGGTTGGGCTGAA

GACGCCGAATATGATCGTCAACTGCTGTATCAAATTACCTGGGATGGTCTGCGTACGCAA

TACCTGACGGACTATCTGAGCCAGCTGCTGTTGGCTGTGCACAAAGACGGGATTAATCTG

CGAGGCGCGCTGACGTGGAGTTTTGTCGATAATTGGGAGTGGGGTTTAGGGATGCAACAG

AAATTCGGATTTCAGTTTGTTAATCAATCAGATCCCGATCTGACACGCACGTTTAAACTG

AGCGCTCACGCTTACGCCCAATTTGGGCGTAATCATCTGCACCACCACCACCACCACTAA

FP#8 rBHT(Δ1-22)-6XHIS   SEQ ID NO. 18

MVTYPGAIPLSLTSNYETPSPTAIPLEPTPTATGTAELDALWNLVEAQYPVQTAAVTTLV

TVPDDYKFEADPPSYALAGYETSEIAGLKFPKGFKFGVAGAAIQVEGAAKAEGRGPSTWD

YLCHHYASTQCNNYDPDITTNHYYLYPLDFARLQHLGINTYSFSISWTRIYPLGAYVNE

AGLAHYDAVIHSAKKYGLEPVGTVFHWDTPLSLMLKYGAWQDTGDQIVKDFVTYATTVFK

RYGNEVKTWFTFNEPRVFCSQNSGLPYNLTYPEGINSTSAVFRCTYNVLKAHGHAVKVYR

DLVASGTIAAGEIGFKSDDNYPIPARPGNADDEESAKRHEAFRIGIFAQPVYGNGDYPDV

VKETVGDMLPALTDEDKGYIKGSGDIFAIDGYRTDISHAALNGIANCIRNQSDPNWPVCE

EGSDPFAHVYPSGFAIGQSADPLSSWLVNSAPFIRDQLKFLTQTYPAKGGIYFSEFGWAE

8. SEQUENCE LISTING

DAEYDRQLLYQITWDGLRTQYLTDYLSQLLLAVHKDGINLRGALTWSFVDNWEWGLGMQQ

KFGFQFVNQSDPDLTRTFKLSAHAYAQFGRNHLHHHHHH

FP#9 aMF-rBHT(Δ1-110)-6XHIS (EcoRI-NotI)     SEQ ID NO. 19

ATGAGATTTCCTTCAATTTTTACTGCAGTTTTATTCGCAGCATCCTCCGCATTAGCTGCT

CCAGTCAACACTACAACAGAAGATGAAACGGCACAAATTCCGGCTGAAGCTGTCATCGGT

TACTCAGATTTAGAAGGGGATTTCGATGTTGCTGTTTTGCCATTTTCCAACAGCACAAAT

AACGGGTTATTGTTTATAAATACTACTATTGCCAGCATTGCTGCTAAAGAAGAAGGGGTA

TCTCTCGAGAAAAGAGAGGCTGAAGCTTACGTAGAATTC ATGTTTCCAAAGGGGTTTAAG

TTTGGTGTTGCGGGGGCAGCCATTCAAGTTGAAGGTGCAGCAAAAGCCGAAGGGCGGGGC

CCAAGTACCTGGGATTATCTGTGTCATCACTATGCCAGCACGCAGTGTAACAATTATGAT

CCCGATATTACAACCAACCATTACTACCTGTACCCATTGGACTTTGCGCGCCTGCAACAC

CTAGGCATTAACACTTACTCGTTTTCAATTTCATGGACGCGTATTTATCCATTGGGCGCA

GGCTATGTTAATGAAGCAGGGTTAGCCCACTATGATGCCGTAATCCATAGTGCCAAGAAG

TATGGTCTGGAACCAGTGGGCACCGTTTTTCACTGGGATACGCCACTGTCTCTGATGCTG

AAATACGGTGCCTGGCAAGATACTGGTGACCAAATTGTTAAGGACTTTGTTACCTATGCC

ACAACTGTGTTTAAGCGTTATGGTAATGAAGTCAAGACGTGGTTTACTTTCAATGAACCA

CGGGTTTTCTGTTCACAAAATAGTGGTCTGCCATACAATCTGACGTATCCAGAAGGTATT

AACAGCACCTCCGCTGTATTTCGTTGCACCTACAATGTTCTGAAAGCTCATGGTCATGCT

GTTAAAGTGTATCGGGATCTAGTTGCCTCCGGGACCATTGCGGCAGGTGAAATCGGCTTT

AAATCCGATGATAACTACCCAATCCCGGCCCGTCCAGGGAACGCCGATGACGAGGAATCA

GCCAAGCGTCACGAGGCTTTTCGCATTGGGATTTTTGCGCAACCGGTTTATGGTAATGGC

GATTATCCAGATGTTGTTAAAGAAACTGTTGGAGATATGCTGCCGGCCCTGACGGATGAA

GATAAAGGATACATTAAAGGTAGCGGAGATATTTTTGCGATTGACGGGTATCGTACCGAT

ATTTCCCATGCGGCTCTGAACGGGATCGCGAATTGTATTCGCAACCAAAGTGACCCGAAT

TGGCCAGTGTGTGAAGAAGGGTCAGATCCTTTTGCTCATGTTTACCCATCCGGGTTTGCT

ATTGGTCAATCAGCCGATCCACTGTCTTCATGGTTAGTCAACTCAGCCCCGTTTATCCGC

GATCAACTGAAGTTTCTGACACAAACCTACCCTGCTAAGGGTGGTATTTATTTCTCGGAA

TTTGGTTGGGCTGAAGACGCCGAATATGATCGTCAACTGCTGTATCAAATTACCTGGGAT

GGTCTGCGTACGCAATACCTGACGGACTATCTGAGCCAGCTGCTGTTGGCTGTGCACAAA

GACGGGATTAATCTGCGAGGCGCGCTGACGTGGAGTTTTGTCGATAATTGGGAGTGGGGT

TTAGGGATGCAACAGAAATTCGGATTTCAGTTTGTTAATCAATCAGATCCCGATCTGACA

CGCACGTTTAAACTGAGCGCTCACGCTTACGCCCAATTTGGGCGTAATCATCTGCACCAC

CACCACCACTAA

FP#9 aMF-rBHT (Δ1-110)-6XHIS     SEQ ID NO. 20

MRFPSIFTAVLFAASSALAAPVNTTTEDETAQIPAEAVIGYSDLEGDFDVAVLPFSNSTN

NGLLFINTTIASIAAKEEGVSLEKREAEAYVEF MFPKGFKFGVAGAAIQVEGAAKAEGRG

PSTWDYLCHHYASTQCNNYDPDITTNHYYLYPLDFARLQHLGINTYSFSISWTRIYPLGA

GYVNEAGLAHYDAVIHSAKKYGLEPVGTVFHWDTPLSLMLKYGAWQDTGDQIVKDFVTYA

-continued

8. SEQUENCE LISTING

TTVFKRYGNEVKTWFTFNEPRVFCSQNSGLPYNLTYPEGINSTSAVFRCTYNVLKAHGHA

VKVYRDLVASGTIAAGEIGFKSDDNYPIPARPGNADDEESAKRHEAFRIGIFAQPVYGNG

DYPDVVKETVGDMLPALTDEDKGYIKGSGDIFAIDGYRTDISHAALNGIANCIRNQSDPN

WPVCEEGSDPFAHVYPSGFAIGQSADPLSSWLVNSAPFIRDQLKFLTQTYPAKGGIYFSE

FGWAEDAEYDRQLLYQITWDGLRTQYLTDYLSQLLLAVHKDGINLRGALTWSFVDNWEWG

LGMQQKFGFQFVNQSDPDLTRTFKLSAHAYAQFGRNHLHHHHHH

---

What is claimed is:

1. An isolated DNA encoding a recombinant β-hexosyl-transferase (rBHT) protein having the amino acid sequence set forth in SEQ ID NO: 12, 14, or 20.

2. The isolated DNA encoding the recombinant β-hexosyl-transferase (rBHT) protein of claim 1 having the amino acid sequence set forth in SEQ ID NO: 12 or 14.

3. The isolated DNA encoding the recombinant β-hexosyl-transferase (rBHT) protein of claim 1, wherein the nucleotide sequence of the DNA has at least 97% sequence identity with the nucleic acid sequence set forth in SEQ ID NO: 11, 13, or 19.

4. The isolated DNA encoding the recombinant β-hexosyl-transferase (rBHT) protein of claim 3, wherein the nucleotide sequence of the DNA has at least 97% sequence identity with the nucleic acid sequence set forth in SEQ ID NO: 13 or 15.

5. A method for producing enzymatically active recombinant β-hexosyl-transferase (rBHT) protein in a cultured eukaryotic host cell which comprises transforming the eukaryotic host cell with a plasmid under the control of a suitable promotor wherein the plasmid contains an isolated DNA encoding a rBHT protein having the amino acid sequence set forth in SEQ ID NO: 12, 14, or 20 wherein the promoter is operably linked to the isolated DNA, and culturing the transformed cell under conditions such that the rBHT protein is produced, wherein the rBHT protein produced by the transformed cell has 3-hexosyl-transferase enzymatic activity.

6. The method of claim 5, wherein the enzymatically active rBHT protein has a specific activity of 8 U/mg at 20° C.

7. The method of claim 5, wherein the eukaryotic host cell is a yeast cell.

8. An isolated DNA encoding a recombinant β-hexosyl-transferase (rBHT) protein wherein the nucleotide sequence of the DNA has at least 99.5% sequence identity with the nucleic acid sequence set forth in SEQ ID NO: 11, 13, or 19 wherein the rBHT protein has β-hexosyl-transferase enzymatic activity.

9. The isolated DNA coding for the recombinant β-hexosyl-transferase (rBHT) protein of claim 8, wherein the nucleotide sequence of the DNA has at least 99.5% sequence identity with the nucleic acid sequence set forth in SEQ ID NO: 11 or 13.

* * * * *

SEQUENCE LISTING

<160> NUMBER OF SEQ ID NOS: 27

<210> SEQ ID NO 1
<211> LENGTH: 1782
<212> TYPE: DNA
<213> ORGANISM: artificial
<220> FEATURE:
<223> OTHER INFORMATION: laboratory synthesized sequence

<400> SEQUENCE: 1

```
atgatgctgc atgctgcact gctagtagcg ctgccatgtg ttgttttggc gcgcccggcc      60
ggagcggtta cttatccggg agccattcct ctgtccctga cgagcaatta cgaaaccccca    120
agtccgacag caatcccgct ggagccaaca ccgacggcta ccggtacagc agaattagat    180
gcgctgtgga acttagtcga agctcagtac ccagttcaaa ctgctgcagt gacaactttg    240
gtgacagtgc ccgatgatta aagtttgag gcagatccac cgagttatgc attagcaggg     300
tatgaaacaa gcgagattgc cggactgaag tttccaaagg ggtttaagtt tggtgttgcg    360
ggggcagcca ttcaagttga aggtgcagca aaagccgaag gcgggggccc aagtacctgg    420
gattatctgt gtcatcacta tgccagcacg cagtgtaaca attatgatcc cgatattaca    480
accaaccatt actacctgta cccattggac tttgcgcgcc tgcaacacct aggcattaac    540
acttactcgt tttcaatttc atggacgcgt atttatccat gggcgcagg ctatgttaat    600
gaagcagggt tagcccacta tgatgccgta atccatagtg ccaagaagta tggtctggaa    660
ccagtgggca ccgttttca ctgggatacg ccactgtctc tgatgctgaa atacggtgcc    720
tggcaagata ctggtgacca aattgttaag gactttgtta cctatgccac aactgtgttt    780
aagcgttatg gtaatgaagt caagacgtgg tttacttcca atgaaccacg ggttttctgt    840
tcacaaaata gtggtctgcc atacaatctg acgtatccag aaggtattaa cagcaccctcc   900
gctgtatttc gttgcaccta caatgttctg aaagctcatg gtcatgctgt aaagtgtat     960
cgggatctag ttgcctccgg gaccattgcg gcaggtgaaa tcggctttaa atccgatgat    1020
aactacccaa tcccggcccg tccagggaac gccgatgacg aggaatcagc caagcgtcac    1080
gaggcttttc gcattgggat ttttgcgcaa ccggttatg gtaatggcga ttatccagat    1140
gttgttaaag aaactgttgg agatatgctg ccggccctga cggatgaaga taaaggatac    1200
attaaaggta gcggagatat ttttgcgatt gacgggtatc gtaccgatat ttcccatgcg    1260
gctctgaacg ggatcgcgaa ttgtattcgc aaccaaagtg acccgaattg gccagtgtgt    1320
gaagaagggt cagatccttt tgctcatgtt tacccatccg ggtttgctat ggtcaatca    1380
gccgatccac tgtcttcatg gttagtcaac tcagccccgt ttatccgcga tcaactgaag    1440
```

```
tttctgacac aaacctaccc tgctaagggt ggtatttatt tctcggaatt tggttgggct    1500
gaagacgccg aatatgatcg tcaactgctg tatcaaatta cctgggatgg tctgcgtacg    1560
caatacctga cggactatct gagccagctg ctgttggctg tgcacaaaga cgggattaat    1620
ctgcgaggcg cgctgacgtg gagttttgtc gataattggg agtggggttt agggatgcaa    1680
cagaaattcg gatttcagtt tgttaatcaa tcagatcccg atctgacacg cacgtttaaa    1740
ctgagcgctc acgcttacgc ccaatttggg cgtaatcatc tg                       1782

<210> SEQ ID NO 2
<211> LENGTH: 594
<212> TYPE: PRT
<213> ORGANISM: artificial
<220> FEATURE:
<223> OTHER INFORMATION: Synthesized sequence

<400> SEQUENCE: 2

Met Met Leu His Ala Ala Leu Leu Val Ala Leu Pro Cys Val Val Leu
1               5                   10                  15

Ala Arg Pro Ala Gly Ala Val Thr Tyr Pro Gly Ala Ile Pro Leu Ser
            20                  25                  30

Leu Thr Ser Asn Tyr Glu Thr Pro Ser Pro Thr Ala Ile Pro Leu Glu
        35                  40                  45

Pro Thr Pro Thr Ala Thr Gly Thr Ala Glu Leu Asp Ala Leu Trp Asn
    50                  55                  60

Leu Val Glu Ala Gln Tyr Pro Val Gln Thr Ala Ala Val Thr Thr Leu
65                  70                  75                  80

Val Thr Val Pro Asp Asp Tyr Lys Phe Glu Ala Asp Pro Pro Ser Tyr
                85                  90                  95

Ala Leu Ala Gly Tyr Glu Thr Ser Glu Ile Ala Gly Leu Lys Phe Pro
            100                 105                 110

Lys Gly Phe Lys Phe Gly Val Ala Gly Ala Ala Ile Gln Val Glu Gly
        115                 120                 125

Ala Ala Lys Ala Glu Gly Arg Gly Pro Ser Thr Trp Asp Tyr Leu Cys
    130                 135                 140

His His Tyr Ala Ser Thr Gln Cys Asn Asn Tyr Asp Pro Asp Ile Thr
145                 150                 155                 160

Thr Asn His Tyr Tyr Leu Tyr Pro Leu Asp Phe Ala Arg Leu Gln His
                165                 170                 175

Leu Gly Ile Asn Thr Tyr Ser Phe Ser Ile Ser Trp Thr Arg Ile Tyr
            180                 185                 190

Pro Leu Gly Ala Gly Tyr Val Asn Glu Ala Gly Leu Ala His Tyr Asp
        195                 200                 205

Ala Val Ile His Ser Ala Lys Lys Tyr Gly Leu Glu Pro Val Gly Thr
    210                 215                 220

Val Phe His Trp Asp Thr Pro Leu Ser Leu Met Leu Lys Tyr Gly Ala
225                 230                 235                 240

Trp Gln Asp Thr Gly Asp Gln Ile Val Lys Asp Phe Val Thr Tyr Ala
                245                 250                 255

Thr Thr Val Phe Lys Arg Tyr Gly Asn Glu Val Lys Thr Trp Phe Thr
            260                 265                 270

Phe Asn Glu Pro Arg Val Phe Cys Ser Gln Asn Ser Gly Leu Pro Tyr
        275                 280                 285

Asn Leu Thr Tyr Pro Glu Gly Ile Asn Ser Thr Ser Ala Val Phe Arg
    290                 295                 300
```

```
Cys Thr Tyr Asn Val Leu Lys Ala His Gly His Ala Val Lys Val Tyr
305                 310                 315                 320
Arg Asp Leu Val Ala Ser Gly Thr Ile Ala Ala Gly Glu Ile Gly Phe
                325                 330                 335
Lys Ser Asp Asn Tyr Pro Ile Pro Ala Arg Pro Gly Asn Ala Asp
            340                 345                 350
Asp Glu Glu Ser Ala Lys Arg His Glu Ala Phe Arg Ile Gly Ile Phe
                355                 360                 365
Ala Gln Pro Val Tyr Gly Asn Gly Asp Tyr Pro Asp Val Val Lys Glu
        370                 375                 380
Thr Val Gly Asp Met Leu Pro Ala Leu Thr Asp Glu Asp Lys Gly Tyr
385                 390                 395                 400
Ile Lys Gly Ser Gly Asp Ile Phe Ala Ile Asp Gly Tyr Arg Thr Asp
                405                 410                 415
Ile Ser His Ala Ala Leu Asn Gly Ile Ala Asn Cys Ile Arg Asn Gln
                420                 425                 430
Ser Asp Pro Asn Trp Pro Val Cys Glu Glu Gly Ser Asp Pro Phe Ala
                435                 440                 445
His Val Tyr Pro Ser Gly Phe Ala Ile Gly Gln Ser Ala Asp Pro Leu
        450                 455                 460
Ser Ser Trp Leu Val Asn Ser Ala Pro Phe Ile Arg Asp Gln Leu Lys
465                 470                 475                 480
Phe Leu Thr Gln Thr Tyr Pro Ala Lys Gly Ile Tyr Phe Ser Glu
                485                 490                 495
Phe Gly Trp Ala Glu Asp Ala Glu Tyr Asp Arg Gln Leu Leu Tyr Gln
                500                 505                 510
Ile Thr Trp Asp Gly Leu Arg Thr Gln Tyr Leu Thr Asp Tyr Leu Ser
                515                 520                 525
Gln Leu Leu Leu Ala Val His Lys Asp Gly Ile Asn Leu Arg Gly Ala
        530                 535                 540
Leu Thr Trp Ser Phe Val Asp Asn Trp Glu Trp Gly Leu Gly Met Gln
545                 550                 555                 560
Gln Lys Phe Gly Phe Gln Phe Val Asn Gln Ser Asp Pro Asp Leu Thr
                565                 570                 575
Arg Thr Phe Lys Leu Ser Ala His Ala Tyr Ala Gln Phe Gly Arg Asn
                580                 585                 590

His Leu

<210> SEQ ID NO 3
<211> LENGTH: 2088
<212> TYPE: DNA
<213> ORGANISM: artificial
<220> FEATURE:
<223> OTHER INFORMATION: laboratory synthesized

<400> SEQUENCE: 3
atgagatttc cttcaatttt tactgcagtt ttattcgcag catcctccgc attagctgct       60
ccagtcaaca ctacaacaga agatgaaacg gcacaaattc cggctgaagc tgtcatcggt      120
tactcagatt tagaagggga tttcgatgtt gctgttttgc catttccaa cagcacaaat       180 aacgggttat tgtttataaa tactactatt gccagcattg ctgctaaaga agaaggggta      240
tctctcgaga aaagagaggc tgaagctcac caccaccacc accacgaaaa cctgtatttt      300
cagatgatgc tgcatgctgc actgctagta gcgctgccat gttgtgtttt ggcgcgcccg      360
gccggagcgg ttacttatcc gggagccatt cctctgtccc tgacgagcaa ttacgaaacc      420
```

```
ccaagtccga cagcaatccc gctggagcca acaccgacgg ctaccggtac agcagaatta     480
gatgcgctgt ggaacttagt cgaagctcag tacccagttc aaactgctgc agtgacaact     540
ttggtgacag tgcccgatga ttataagttt gaggcagatc caccgagtta tgcattagca     600
gggtatgaaa caagcgagat tgccggactg aagtttccaa aggggtttaa gtttggtgtt     660 gcggggggcag ccattcaagt tgaaggtgca gcaaaagccg aagggcgggg cccaagtacc    720
tgggattatc tgtgtcatca ctatgccagc acgcagtgta acaattatga tcccgatatt     780
acaaccaacc attactacct gtacccattg gactttgcgc gcctgcaaca cctaggcatt     840
aacacttact cgttttcaat tcatggacgc gtatttatc cattgggcgc aggctatgtt      900
aatgaagcag ggttagccca ctatgatgcc gtaatccata gtgccaagaa gtatggtctg     960
gaaccagtgg gcaccgtttt tcactgggat acgccactgt ctctgatgct gaaatacggt    1020
gcctggcaag atactggtga ccaaattgtt aaggactttg ttacctatgc cacaactgtg    1080
tttaagcgtt atggtaatga agtcaagacg tggtttactt tcaatgaacc acgggttttc    1140
tgttcacaaa atagtggtct gccatacaat ctgacgtatc cagaaggtat taacagcacc   1200
tccgctgtat ttcgttgcac ctacaatgtt ctgaaagctc atggtcatgc tgttaaagtg    1260
tatcgggatc tagttgcctc cgggaccatt gcggcaggtg aaatcggctt taaatccgat    1320
gataactacc caatcccggc ccgtccaggg aacgccgatg acgaggaatc agccaagcgt    1380
cacgaggctt ttcgcattgg gattttttgcg caaccggttt atggtaatgg cgattatcca   1440
gatgttgtta agaaaactgt tggagatatg ctgccggccc tgacggatga agataaagga    1500
tacattaaag gtagcggaga tattttttgcg attgacgggt atcgtaccga tatttcccat   1560
gcggctctga acgggatcgc cgaattgtat tcgcaaccaaa gtgacccgaa ttggccagtg   1620
tgtgaagaag ggtcagatcc ttttgctcat gtttaccccat ccgggtttgc tattggtcaa   1680
tcagccgatc cactgtcttc atggttagtc aactcagccc cgtttatccg cgatcaactg    1740
aagtttctga cacaaaccta ccctgctaag ggtggtattt atttctcgga atttggttgg    1800
gctgaagacg ccgaatatga tcgtcaactg ctgtatcaaa ttacctggga tggtctgcgt    1860
acgcaatacc tgacggacta tctgagccag ctgctgttgg ctgtgcacaa agacgggatt    1920
aatctgcgag gcgcgctgac gtggagtttt gtcgataatt gggagtgggg tttagggatg    1980
caacagaaat tcggatttca gtttgttaat caatcagatc ccgatctgac acgcacgttt    2040
aaactgagcg ctcacgctta cgcccaattt gggcgtaatc atctgtaa                 2088
```

<210> SEQ ID NO 4
<211> LENGTH: 695
<212> TYPE: PRT
<213> ORGANISM: artificial
<220> FEATURE:
<223> OTHER INFORMATION: laboratory synthesized

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

-continued

```
Phe Ile Asn Thr Thr Ile Ala Ser Ile Ala Ala Lys Glu Glu Gly Val
 65                  70                  75                  80

Ser Leu Glu Lys Arg Glu Ala Glu Ala His His His His His His Glu
                 85                  90                  95

Asn Leu Tyr Phe Gln Met Met Leu His Ala Ala Leu Leu Val Ala Leu
                100                 105                 110

Pro Cys Val Val Leu Ala Arg Pro Ala Gly Ala Val Thr Tyr Pro Gly
            115                 120                 125

Ala Ile Pro Leu Ser Leu Thr Ser Asn Tyr Glu Thr Pro Ser Pro Thr
        130                 135                 140

Ala Ile Pro Leu Glu Pro Thr Pro Thr Ala Thr Gly Thr Ala Glu Leu
145                 150                 155                 160

Asp Ala Leu Trp Asn Leu Val Glu Ala Gln Tyr Pro Val Gln Thr Ala
                165                 170                 175

Ala Val Thr Thr Leu Val Thr Val Pro Asp Asp Tyr Lys Phe Glu Ala
            180                 185                 190

Asp Pro Pro Ser Tyr Ala Leu Ala Gly Tyr Glu Thr Ser Glu Ile Ala
        195                 200                 205

Gly Leu Lys Phe Pro Lys Gly Phe Lys Phe Gly Val Ala Gly Ala Ala
    210                 215                 220

Ile Gln Val Glu Gly Ala Ala Lys Ala Glu Gly Arg Gly Pro Ser Thr
225                 230                 235                 240

Trp Asp Tyr Leu Cys His His Tyr Ala Ser Thr Gln Cys Asn Asn Tyr
                245                 250                 255

Asp Pro Asp Ile Thr Thr Asn His Tyr Tyr Leu Tyr Pro Leu Asp Phe
            260                 265                 270

Ala Arg Leu Gln His Leu Gly Ile Asn Thr Tyr Ser Phe Ser Ile Ser
        275                 280                 285

Trp Thr Arg Ile Tyr Pro Leu Gly Ala Gly Tyr Val Asn Glu Ala Gly
    290                 295                 300

Leu Ala His Tyr Asp Ala Val Ile His Ser Ala Lys Lys Tyr Gly Leu
305                 310                 315                 320

Glu Pro Val Gly Thr Val Phe His Trp Asp Thr Pro Leu Ser Leu Met
                325                 330                 335

Leu Lys Tyr Gly Ala Trp Gln Asp Thr Gly Asp Gln Ile Val Lys Asp
            340                 345                 350

Phe Val Thr Tyr Ala Thr Thr Val Phe Lys Arg Tyr Gly Asn Glu Val
        355                 360                 365

Lys Thr Trp Phe Thr Phe Asn Glu Pro Arg Val Phe Cys Ser Gln Asn
    370                 375                 380

Ser Gly Leu Pro Tyr Asn Leu Thr Tyr Pro Glu Gly Ile Asn Ser Thr
385                 390                 395                 400

Ser Ala Val Phe Arg Cys Thr Tyr Asn Val Leu Lys Ala His Gly His
                405                 410                 415

Ala Val Lys Val Tyr Arg Asp Leu Val Ala Ser Gly Thr Ile Ala Ala
            420                 425                 430

Gly Glu Ile Gly Phe Lys Ser Asp Asp Asn Tyr Pro Ile Pro Ala Arg
        435                 440                 445

Pro Gly Asn Ala Asp Asp Glu Glu Ser Ala Lys Arg His Glu Ala Phe
    450                 455                 460

Arg Ile Gly Ile Phe Ala Gln Pro Val Tyr Gly Asn Gly Asp Tyr Pro
465                 470                 475                 480

Asp Val Val Lys Glu Thr Val Gly Asp Met Leu Pro Ala Leu Thr Asp
```

```
                    485              490              495
Glu Asp Lys Gly Tyr Ile Lys Gly Ser Gly Asp Ile Phe Ala Ile Asp
                500              505              510

Gly Tyr Arg Thr Asp Ile Ser His Ala Ala Leu Asn Gly Ile Ala Asn
                515              520              525

Cys Ile Arg Asn Gln Ser Asp Pro Asn Trp Pro Val Cys Glu Glu Gly
                530              535              540

Ser Asp Pro Phe Ala His Val Tyr Pro Ser Gly Phe Ala Ile Gly Gln
545              550              555              560

Ser Ala Asp Pro Leu Ser Ser Trp Leu Val Asn Ser Ala Pro Phe Ile
                565              570              575

Arg Asp Gln Leu Lys Phe Leu Thr Gln Thr Tyr Pro Ala Lys Gly Gly
                580              585              590

Ile Tyr Phe Ser Glu Phe Gly Trp Ala Glu Asp Ala Glu Tyr Asp Arg
                595              600              605

Gln Leu Leu Tyr Gln Ile Thr Trp Asp Gly Leu Arg Thr Gln Tyr Leu
                610              615              620

Thr Asp Tyr Leu Ser Gln Leu Leu Ala Val His Lys Asp Gly Ile
625              630              635              640

Asn Leu Arg Gly Ala Leu Thr Trp Ser Phe Val Asp Asn Trp Glu Trp
                645              650              655

Gly Leu Gly Met Gln Gln Lys Phe Gly Phe Gln Phe Val Asn Gln Ser
                660              665              670

Asp Pro Asp Leu Thr Arg Thr Phe Lys Leu Ser Ala His Ala Tyr Ala
                675              680              685

Gln Phe Gly Arg Asn His Leu
                690              695

<210> SEQ ID NO 5
<211> LENGTH: 2106
<212> TYPE: DNA
<213> ORGANISM: artificial
<220> FEATURE:
<223> OTHER INFORMATION: laboratory synthesized

<400> SEQUENCE: 5
atgagatttc cttcaattttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgtttttgc catttttccaa cagcacaaat     180 aacgggttat tgtttataaa tactactatt gccagcattg ctgctaaaga agaagggta      240 tctctcgaga aaagagaggc tgaagctcac caccaccacc accacgaaaa cctgtatttt     300
cagatgatgc tgcatgctgc actgctagta gcgctgccat tgttgttttt ggcgcgcccg     360
gccggagcgg ttacttatcc gggagccatt cctctgtccc tgacgagcaa ttacgaaacc     420
ccaagtccga cagcaatccc gctggagcca caccgacgg ctaccggtac agcagaatta     480
gatgcgctgt ggaacttagt cgaagctcag tacccagttc aaactgctgc agtgacaact     540
ttggtgacag tgcccgatga ttataagttt gaggcagatc caccgagtta tgcattagca     600
gggtatgaaa caagcgagat tgccggactg aagtttccaa aggggtttaa gtttggtgtt     660 gcggggggcag ccattcaagt tgaaggtgca gcaaaagccg aagggcgggg cccaagtacc     720
tgggattatc tgtgtcatca ctatgccagc acgcagtgta caattatga tcccgatatt     780 acaaccaacc attactacct gtacccattg gactttgcgc gcctgcaaca cctaggcatt     840
```

```
aacacttact cgttttcaat tcatggacg cgtatttatc cattgggcgc aggctatgtt    900
aatgaagcag ggttagccca ctatgatgcc gtaatccata gtgccaagaa gtatggtctg    960
gaaccagtgg gcaccgtttt tcactgggat acgccactgt ctctgatgct gaaatacggt   1020
gcctggcaag atactggtga ccaaattgtt aaggactttg ttacctatgc cacaactgtg   1080
tttaagcgtt atggtaatga agtcaagacg tggtttactt tcaatgaacc acgggttttc   1140
tgttcacaaa atagtggtct gccatacaat ctgacgtatc cagaaggtat taacagcacc   1200
tccgctgtat ttcgttgcac ctacaatgtt ctgaaagctc atggtcatgc tgttaaagtg   1260
tatcgggatc tagttgcctc cgggaccatt gcggcaggtg aaatcggctt aaatccgat    1320
gataactacc caatcccggc ccgtccaggg aacgccgatg acgaggaatc agccaagcgt   1380
cacgaggctt ttcgcattgg gattttttgcg caaccggttt atggtaatgg cgattatcca   1440
gatgttgtta agaaaactgt tggagatatg ctgccggccc tgacggatga agataaagga   1500
tacattaaag gtagcggaga tatttttgcg attgacgggt atcgtaccga tatttcccat   1560
gcggctctga acgggatcgc gaattgtatt cgcaaccaaa gtgacccgaa ttggccagtg   1620
tgtgaagaag ggtcagatcc ttttgctcat gtttacccat ccgggtttgc tattggtcaa   1680
tcagccgatc cactgtcttc atggttagtc aactcagccc cgtttatccg cgatcaactg   1740
aagtttctga cacaaaccta ccctgctaag ggtggtattt atttctcgga atttggttgg   1800
gctgaagacg ccgaatatga tcgtcaactg ctgtatcaaa ttacctggga tggtctgcgt   1860
acgcaatacc tgacggacta tctgagccag ctgctgttgg ctgtgcacaa agacgggatt   1920
aatctgcgag gcgcgctgac gtggagtttt gtcgataatt gggagtgggg tttagggatg   1980
caacagaaat tcggatttca gtttgttaat caatcagatc ccgatctgac acgcacgttt   2040
aaactgagcg ctcacgctta cgcccaattt gggcgtaatc atctgcacca ccaccaccac   2100
cactaa                                                              2106
```

<210> SEQ ID NO 6
<211> LENGTH: 701
<212> TYPE: PRT
<213> ORGANISM: artificial
<220> FEATURE:
<223> OTHER INFORMATION: laboratory synthesized

<400> SEQUENCE: 6

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala His His His His His His Glu
                85                  90                  95

Asn Leu Tyr Phe Gln Met Met Leu His Ala Ala Leu Leu Val Ala Leu
            100                 105                 110

Pro Cys Val Val Leu Ala Arg Pro Ala Gly Ala Val Thr Tyr Pro Gly
        115                 120                 125

Ala Ile Pro Leu Ser Leu Thr Ser Asn Tyr Glu Thr Pro Ser Pro Thr

-continued

```
            130                 135                 140
Ala Ile Pro Leu Glu Pro Thr Pro Thr Ala Thr Gly Thr Ala Glu Leu
145                 150                 155                 160

Asp Ala Leu Trp Asn Leu Val Glu Ala Gln Tyr Pro Val Gln Thr Ala
                165                 170                 175

Ala Val Thr Thr Leu Val Thr Val Pro Asp Asp Tyr Lys Phe Glu Ala
            180                 185                 190

Asp Pro Pro Ser Tyr Ala Leu Ala Gly Tyr Glu Thr Ser Glu Ile Ala
        195                 200                 205

Gly Leu Lys Phe Pro Lys Gly Phe Lys Phe Gly Val Ala Gly Ala Ala
    210                 215                 220

Ile Gln Val Glu Gly Ala Ala Lys Ala Glu Gly Arg Gly Pro Ser Thr
225                 230                 235                 240

Trp Asp Tyr Leu Cys His His Tyr Ala Ser Thr Gln Cys Asn Asn Tyr
                245                 250                 255

Asp Pro Asp Ile Thr Thr Asn His Tyr Tyr Leu Tyr Pro Leu Asp Phe
            260                 265                 270

Ala Arg Leu Gln His Leu Gly Ile Asn Thr Tyr Ser Phe Ser Ile Ser
        275                 280                 285

Trp Thr Arg Ile Tyr Pro Leu Gly Ala Gly Tyr Val Asn Glu Ala Gly
    290                 295                 300

Leu Ala His Tyr Asp Ala Val Ile His Ser Ala Lys Lys Tyr Gly Leu
305                 310                 315                 320

Glu Pro Val Gly Thr Val Phe His Trp Asp Thr Pro Leu Ser Leu Met
                325                 330                 335

Leu Lys Tyr Gly Ala Trp Gln Asp Thr Gly Asp Gln Ile Val Lys Asp
            340                 345                 350

Phe Val Thr Tyr Ala Thr Thr Val Phe Lys Arg Tyr Gly Asn Glu Val
        355                 360                 365

Lys Thr Trp Phe Thr Phe Asn Glu Pro Arg Val Phe Cys Ser Gln Asn
    370                 375                 380

Ser Gly Leu Pro Tyr Asn Leu Thr Tyr Pro Glu Gly Ile Asn Ser Thr
385                 390                 395                 400

Ser Ala Val Phe Arg Cys Thr Tyr Asn Val Leu Lys Ala His Gly His
                405                 410                 415

Ala Val Lys Val Tyr Arg Asp Leu Val Ala Ser Gly Thr Ile Ala Ala
            420                 425                 430

Gly Glu Ile Gly Phe Lys Ser Asp Asp Asn Tyr Pro Ile Pro Ala Arg
        435                 440                 445

Pro Gly Asn Ala Asp Asp Glu Glu Ser Ala Lys Arg His Glu Ala Phe
    450                 455                 460

Arg Ile Gly Ile Phe Ala Gln Pro Val Tyr Gly Asn Gly Asp Tyr Pro
465                 470                 475                 480

Asp Val Val Lys Glu Thr Val Gly Asp Met Leu Pro Ala Leu Thr Asp
                485                 490                 495

Glu Asp Lys Gly Tyr Ile Lys Gly Ser Gly Asp Ile Phe Ala Ile Asp
            500                 505                 510

Gly Tyr Arg Thr Asp Ile Ser His Ala Ala Leu Asn Gly Ile Ala Asn
        515                 520                 525

Cys Ile Arg Asn Gln Ser Asp Pro Asn Trp Pro Val Cys Glu Glu Gly
    530                 535                 540

Ser Asp Pro Phe Ala His Val Tyr Pro Ser Gly Phe Ala Ile Gly Gln
545                 550                 555                 560
```

```
Ser Ala Asp Pro Leu Ser Ser Trp Leu Val Asn Ser Ala Pro Phe Ile
            565                 570                 575

Arg Asp Gln Leu Lys Phe Leu Thr Gln Thr Tyr Pro Ala Lys Gly Gly
            580                 585                 590

Ile Tyr Phe Ser Glu Phe Gly Trp Ala Glu Asp Ala Glu Tyr Asp Arg
            595                 600                 605

Gln Leu Leu Tyr Gln Ile Thr Trp Asp Gly Leu Arg Thr Gln Tyr Leu
            610                 615                 620

Thr Asp Tyr Leu Ser Gln Leu Leu Ala Val His Lys Asp Gly Ile
625                 630                 635                 640

Asn Leu Arg Gly Ala Leu Thr Trp Ser Phe Val Asp Asn Trp Glu Trp
            645                 650                 655

Gly Leu Gly Met Gln Gln Lys Phe Gly Phe Gln Phe Val Asn Gln Ser
            660                 665                 670

Asp Pro Asp Leu Thr Arg Thr Phe Lys Leu Ser Ala His Ala Tyr Ala
            675                 680                 685

Gln Phe Gly Arg Asn His Leu His His His His His His
            690                 695                 700
```

\<210\> SEQ ID NO 7
\<211\> LENGTH: 2070
\<212\> TYPE: DNA
\<213\> ORGANISM: artificial
\<220\> FEATURE:
\<223\> OTHER INFORMATION: laboratory synthesized

\<400\> SEQUENCE: 7

```
atgagatttc cttcaattttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctcgaga aaagagaggc tgaagctatg atgctgcatg ctgcactgct agtagcgctg     300
ccatgtgttg ttttggcgcg cccggccgga gcggttactt atccgggagc cattcctctg     360
tccctgacga gcaattacga aaccccaagt ccgacagcaa tcccgctgga gccaacaccg     420
acggctaccg gtacagcaga attagatgcg ctgtggaact agtcgaagc tcagtaccca     480
gttcaaactg ctgcagtgac aactttggtg acagtgcccg atgattataa gtttgaggca     540
gatccaccga gttatgcatt agcagggtat gaaacaagcg agattgccgg actgaagttt     600
ccaaagggt ttaagtttgg tgttgcgggg gcagccattc aagttgaagg tgcagcaaaa     660
gccgaagggc ggggcccaag tacctgggat tatctgtgtc atcactatgc cagcacgcag     720
tgtaacaatt atgatcccga tattacaacc aaccattact acctgtaccc attggacttt     780
gcgcgcctgc aacacctagg cattaacact tactcgtttt caatttcatg gacgcgtatt     840
tatccattgg gcgcaggcta tgttaatgaa gcagggttag cccactatga tgccgtaatc     900
catagtgcca agaagtatgg tctggaacca gtgggcaccg ttttcactg ggatacgcca     960
ctgtctctga tgctgaaata cggtgcctgg aagatactg tgaccaaat tgttaaggac    1020
tttgttacct atgccacaac tgtgtttaag cgttatggta atgaagtcaa gacgtggttt    1080
actttcaatg aaccacgggt tttctgttca caaatagtg gtctgccata caatctgacg    1140
tatccagaag gtattaacag cacctccgct gtatttcgtt gcacctacaa tgttctgaaa    1200
gctcatggtc atgctgttaa agtgtatcgg gatctagttg cctccgggac cattgcggca    1260
```

```
ggtgaaatcg gctttaaatc cgatgataac tacccaatcc cggcccgtcc agggaacgcc    1320
gatgacgagg aatcagccaa gcgtcacgag gcttttcgca ttgggatttt tgcgcaaccg    1380
gtttatggta atggcgatta tccagatgtt gttaaagaaa ctgttggaga tatgctgccg    1440
gccctgacgg atgaagataa aggatacatt aaaggtagcg agatatttt tgcgattgac     1500 gggtatcgta ccgatatttc ccatgcggct ctgaacggga tcgcgaattg tattcgcaac    1560
caaagtgacc cgaattggcc agtgtgtgaa gaagggtcag atcctttgc tcatgtttac     1620 ccatccgggt ttgctattgg tcaatcagcc gatccactgt cttcatggtt agtcaactca    1680
gccccgttta ccgcgatca actgaagttt ctgacacaaa cctaccctgc taagggtggt     1740
atttatttct cggaatttgg ttgggctgaa gacgccgaat atgatcgtca actgctgtat    1800
caaattacct gggatggtct gcgtacgcaa tacctgacgg actatctgag ccagctgctg    1860
ttggctgtgc acaaagacgg gattaatctg cgaggcgcgc tgacgtggag ttttgtcgat    1920
aattgggagt ggggtttagg gatgcaacag aaattcggat ttcagtttgt taatcaatca    1980
gatcccgatc tgacacgcac gtttaaactg agcgctcacg cttacgccca atttgggcgt    2040
aatcatctgc accaccacca ccaccactaa                                     2070
```

<210> SEQ ID NO 8
<211> LENGTH: 689
<212> TYPE: PRT
<213> ORGANISM: artificial
<220> FEATURE:
<223> OTHER INFORMATION: laboratory synthesized

<400> SEQUENCE: 8

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Lys Glu Glu Gly Val
65                  70                  75                  80

Ser Leu Glu Lys Arg Glu Ala Glu Ala Met Met Leu His Ala Ala Leu
                85                  90                  95

Leu Val Ala Leu Pro Cys Val Val Leu Ala Arg Pro Ala Gly Ala Val
                100                 105                 110

Thr Tyr Pro Gly Ala Ile Pro Leu Ser Leu Thr Ser Asn Tyr Glu Thr
            115                 120                 125

Pro Ser Pro Thr Ala Ile Pro Leu Glu Pro Thr Pro Thr Ala Thr Gly
        130                 135                 140

Thr Ala Glu Leu Asp Ala Leu Trp Asn Leu Val Glu Ala Gln Tyr Pro
145                 150                 155                 160

Val Gln Thr Ala Ala Val Thr Thr Leu Val Thr Val Pro Asp Asp Tyr
                165                 170                 175

Lys Phe Glu Ala Asp Pro Pro Ser Tyr Ala Leu Ala Gly Tyr Glu Thr
                180                 185                 190

Ser Glu Ile Ala Gly Leu Lys Phe Pro Lys Gly Phe Lys Phe Gly Val
            195                 200                 205

Ala Gly Ala Ala Ile Gln Val Glu Gly Ala Ala Lys Ala Glu Gly Arg
```

```
                210                 215                 220
Gly Pro Ser Thr Trp Asp Tyr Leu Cys His His Tyr Ala Ser Thr Gln
225                 230                 235                 240

Cys Asn Asn Tyr Asp Pro Asp Ile Thr Thr Asn His Tyr Tyr Leu Tyr
                245                 250                 255

Pro Leu Asp Phe Ala Arg Leu Gln His Leu Gly Ile Asn Thr Tyr Ser
                260                 265                 270

Phe Ser Ile Ser Trp Thr Arg Ile Tyr Pro Leu Gly Ala Gly Tyr Val
            275                 280                 285

Asn Glu Ala Gly Leu Ala His Tyr Asp Ala Val Ile His Ser Ala Lys
        290                 295                 300

Lys Tyr Gly Leu Glu Pro Val Gly Thr Val Phe His Trp Asp Thr Pro
305                 310                 315                 320

Leu Ser Leu Met Leu Lys Tyr Gly Ala Trp Gln Asp Thr Gly Asp Gln
                325                 330                 335

Ile Val Lys Asp Phe Val Thr Tyr Ala Thr Thr Val Phe Lys Arg Tyr
                340                 345                 350

Gly Asn Glu Val Lys Thr Trp Phe Thr Phe Asn Glu Pro Arg Val Phe
            355                 360                 365

Cys Ser Gln Asn Ser Gly Leu Pro Tyr Asn Leu Thr Tyr Pro Glu Gly
        370                 375                 380

Ile Asn Ser Thr Ser Ala Val Phe Arg Cys Thr Tyr Asn Val Leu Lys
385                 390                 395                 400

Ala His Gly His Ala Val Lys Val Tyr Arg Asp Leu Val Ala Ser Gly
                405                 410                 415

Thr Ile Ala Ala Gly Glu Ile Gly Phe Lys Ser Asp Asp Asn Tyr Pro
                420                 425                 430

Ile Pro Ala Arg Pro Gly Asn Ala Asp Asp Glu Glu Ser Ala Lys Arg
            435                 440                 445

His Glu Ala Phe Arg Ile Gly Ile Phe Ala Gln Pro Val Tyr Gly Asn
        450                 455                 460

Gly Asp Tyr Pro Asp Val Val Lys Glu Thr Val Gly Asp Met Leu Pro
465                 470                 475                 480

Ala Leu Thr Asp Glu Asp Lys Gly Tyr Ile Lys Gly Ser Gly Asp Ile
                485                 490                 495

Phe Ala Ile Asp Gly Tyr Arg Thr Asp Ile Ser His Ala Ala Leu Asn
                500                 505                 510

Gly Ile Ala Asn Cys Ile Arg Asn Gln Ser Asp Pro Asn Trp Pro Val
            515                 520                 525

Cys Glu Glu Gly Ser Asp Pro Phe Ala His Val Tyr Pro Ser Gly Phe
        530                 535                 540

Ala Ile Gly Gln Ser Ala Asp Pro Leu Ser Ser Trp Leu Val Asn Ser
545                 550                 555                 560

Ala Pro Phe Ile Arg Asp Gln Leu Lys Phe Leu Thr Gln Thr Tyr Pro
                565                 570                 575

Ala Lys Gly Gly Ile Tyr Phe Ser Glu Phe Gly Trp Ala Glu Asp Ala
                580                 585                 590

Glu Tyr Asp Arg Gln Leu Leu Tyr Gln Ile Thr Trp Asp Gly Leu Arg
            595                 600                 605

Thr Gln Tyr Leu Thr Asp Tyr Leu Ser Gln Leu Leu Leu Ala Val His
        610                 615                 620

Lys Asp Gly Ile Asn Leu Arg Gly Ala Leu Thr Trp Ser Phe Val Asp
625                 630                 635                 640
```

Asn Trp Glu Trp Gly Leu Gly Met Gln Gln Lys Phe Gly Phe Gln Phe
            645                 650                 655

Val Asn Gln Ser Asp Pro Asp Leu Thr Arg Thr Phe Lys Leu Ser Ala
        660                 665                 670

His Ala Tyr Ala Gln Phe Gly Arg Asn His Leu His His His His
    675                 680                 685

His

<210> SEQ ID NO 9
<211> LENGTH: 2052
<212> TYPE: DNA
<213> ORGANISM: artificial
<220> FEATURE:
<223> OTHER INFORMATION: laboratory synthesized

<400> SEQUENCE: 9

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattc tgctaaaga agaaggggta      240
tctctcgaga aaagagaggc tgaagctatg atgctgcatg ctgcactgct agtagcgctg     300
ccatgtgttg ttttggcgcg cccggccgga gcggttactt atccgggagc cattcctctg     360
tccctgacga gcaattacga aaccccaagt ccgacagcaa tcccgctgga gccaacaccg     420
acggctaccg gtacagcaga attagatgcg ctgtggaact tagtcgaagc tcagtaccca     480
gttcaaactg ctgcagtgac aactttggtg acagtgcccg atgattataa gtttgaggca     540
gatccaccga gttatgcatt agcagggtat gaaacaagcg agattgccgg actgaagttt     600
ccaaaggggt ttaagtttgg tgttgcgggg gcagccattc aagttgaagg tgcagcaaaa     660
gccgaagggc ggggcccaag tacctgggat tatctgtgtc atcactatgc cagcacgcag     720
tgtaacaatt atgatcccga tattacaacc aaccattact acctgtaccc attggacttt     780
gcgcgcctgc aacacctagg cattaacact tactcgtttt caatttcatg gacgcgtatt     840
tatccattgg gcgcaggcta tgttaatgaa gcagggttag cccactatga tgccgtaatc     900
catagtgcca agaagtatgg tctggaacca gtgggcaccg ttttcactg gatacgcca       960
ctgtctctga tgctgaaata cggtgcctgg aagatactg gtgaccaaat tgttaaggac    1020
tttgttacct atgccacaac tgtgtttaag cgttatggta tgaagtcaa acgtggtttt    1080
actttcaatg aaccacgggt tttctgttca caaaatagtg gtctgccata caatctgacg    1140
tatccagaag gtattaacag cacctccgct gtatttcgtt gcacctacaa tgttctgaaa    1200
gctcatggtc atgctgttaa agtgtatcgg gatctagttg cctccgggac cattgcggca    1260
ggtgaaatcg gctttaaatc cgatgataac tacccaatcc cggcccgtcc agggaacgcc    1320
gatgacgagg aatcagccaa gcgtcacgag gcttttcgca ttgggatttt tgcgcaaccg    1380
gtttatggta atggcgatta tccagatgtt gttaaagaaa ctgttggaga tatgctgccg    1440
gccctgacgg atgaagataa aggatacatt aaaggtagcg gagatatttt tgcgattgac    1500
gggtatcgta ccgatatttc ccatgcggct ctgaacggga tcgcgaattg tattcgcaac    1560
caaagtgacc cgaattggcc agtgtgtgaa gaagggtcag atcctttgc tcatgtttac    1620
ccatccgggt ttgctattgg tcaatcagcc gatccactgt cttcatggtt agtcaactca    1680
gccccgttta tccgcgatca actgaagttt ctgacacaaa cctaccctgc taagggtggt    1740
```

```
atttatttct cggaatttgg ttgggctgaa gacgccgaat atgatcgtca actgctgtat   1800
caaattacct gggatggtct gcgtacgcaa tacctgacgg actatctgag ccagctgctg   1860
ttggctgtgc acaaagacgg gattaatctg cgaggcgcgc tgacgtggag ttttgtcgat   1920
aattgggagt ggggtttagg gatgcaacag aaattcggat tcagtttgt taatcaatca    1980 gatcccgatc tgacacgcac gtttaaactg agcgctcacg cttacgccca atttgggcgt   2040
aatcatctgt aa                                                       2052
```

<210> SEQ ID NO 10
<211> LENGTH: 683
<212> TYPE: PRT
<213> ORGANISM: artificial
<220> FEATURE:
<223> OTHER INFORMATION: laboratory synthesized

<400> SEQUENCE: 10

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Lys Glu Glu Gly Val
65                  70                  75                  80

Ser Leu Glu Lys Arg Glu Ala Glu Ala Met Met Leu His Ala Ala Leu
                85                  90                  95

Leu Val Ala Leu Pro Cys Val Val Leu Ala Arg Pro Ala Gly Ala Val
            100                 105                 110

Thr Tyr Pro Gly Ala Ile Pro Leu Ser Leu Thr Ser Asn Tyr Glu Thr
        115                 120                 125

Pro Ser Pro Thr Ala Ile Pro Leu Glu Pro Thr Pro Thr Ala Thr Gly
    130                 135                 140

Thr Ala Glu Leu Asp Ala Leu Trp Asn Leu Val Glu Ala Gln Tyr Pro
145                 150                 155                 160

Val Gln Thr Ala Ala Val Thr Thr Leu Val Thr Val Pro Asp Asp Tyr
                165                 170                 175

Lys Phe Glu Ala Asp Pro Pro Ser Tyr Ala Leu Ala Gly Tyr Glu Thr
            180                 185                 190

Ser Glu Ile Ala Gly Leu Lys Phe Pro Lys Gly Phe Lys Phe Gly Val
        195                 200                 205

Ala Gly Ala Ala Ile Gln Val Glu Gly Ala Ala Lys Ala Glu Gly Arg
    210                 215                 220

Gly Pro Ser Thr Trp Asp Tyr Leu Cys His His Tyr Ala Ser Thr Gln
225                 230                 235                 240

Cys Asn Asn Tyr Asp Pro Asp Ile Thr Thr Asn His Tyr Tyr Leu Tyr
                245                 250                 255

Pro Leu Asp Phe Ala Arg Leu Gln His Leu Gly Ile Asn Thr Tyr Ser
            260                 265                 270

Phe Ser Ile Ser Trp Thr Arg Ile Tyr Pro Leu Gly Ala Gly Tyr Val
        275                 280                 285

Asn Glu Ala Gly Leu Ala His Tyr Asp Ala Val Ile His Ser Ala Lys
    290                 295                 300
```

```
Lys Tyr Gly Leu Glu Pro Val Gly Thr Val Phe His Trp Asp Thr Pro
305                 310                 315                 320

Leu Ser Leu Met Leu Lys Tyr Gly Ala Trp Gln Asp Thr Gly Asp Gln
            325                 330                 335

Ile Val Lys Asp Phe Val Thr Tyr Ala Thr Thr Val Phe Lys Arg Tyr
            340                 345                 350

Gly Asn Glu Val Lys Thr Trp Phe Thr Phe Asn Glu Pro Arg Val Phe
            355                 360                 365

Cys Ser Gln Asn Ser Gly Leu Pro Tyr Asn Leu Thr Tyr Pro Glu Gly
370                 375                 380

Ile Asn Ser Thr Ser Ala Val Phe Arg Cys Thr Tyr Asn Val Leu Lys
385                 390                 395                 400

Ala His Gly His Ala Val Lys Val Tyr Arg Asp Leu Val Ala Ser Gly
                405                 410                 415

Thr Ile Ala Ala Gly Glu Ile Gly Phe Lys Ser Asp Asp Asn Tyr Pro
            420                 425                 430

Ile Pro Ala Arg Pro Gly Asn Ala Asp Asp Glu Ser Ala Lys Arg
            435                 440                 445

His Glu Ala Phe Arg Ile Gly Ile Phe Ala Gln Pro Val Tyr Gly Asn
450                 455                 460

Gly Asp Tyr Pro Asp Val Val Lys Glu Thr Val Gly Asp Met Leu Pro
465                 470                 475                 480

Ala Leu Thr Asp Glu Asp Lys Gly Tyr Ile Lys Gly Ser Gly Asp Ile
            485                 490                 495

Phe Ala Ile Asp Gly Tyr Arg Thr Asp Ile Ser His Ala Ala Leu Asn
            500                 505                 510

Gly Ile Ala Asn Cys Ile Arg Asn Gln Ser Asp Pro Asn Trp Pro Val
            515                 520                 525

Cys Glu Glu Gly Ser Asp Pro Phe Ala His Val Tyr Pro Ser Gly Phe
530                 535                 540

Ala Ile Gly Gln Ser Ala Asp Pro Leu Ser Ser Trp Leu Val Asn Ser
545                 550                 555                 560

Ala Pro Phe Ile Arg Asp Gln Leu Lys Phe Leu Thr Gln Thr Tyr Pro
            565                 570                 575

Ala Lys Gly Gly Ile Tyr Phe Ser Glu Phe Gly Trp Ala Glu Asp Ala
            580                 585                 590

Glu Tyr Asp Arg Gln Leu Leu Tyr Gln Ile Thr Trp Asp Gly Leu Arg
            595                 600                 605

Thr Gln Tyr Leu Thr Asp Tyr Leu Ser Gln Leu Leu Ala Val His
            610                 615                 620

Lys Asp Gly Ile Asn Leu Arg Gly Ala Leu Thr Trp Ser Phe Val Asp
625                 630                 635                 640

Asn Trp Glu Trp Gly Leu Gly Met Gln Gln Lys Phe Gly Phe Gln Phe
            645                 650                 655

Val Asn Gln Ser Asp Pro Asp Leu Thr Arg Thr Phe Lys Leu Ser Ala
            660                 665                 670

His Ala Tyr Ala Gln Phe Gly Arg Asn His Leu
            675                 680
```

<210> SEQ ID NO 11
<211> LENGTH: 2004
<212> TYPE: DNA
<213> ORGANISM: artificial
<220> FEATURE:

<223> OTHER INFORMATION: laboratory synthesized

<400> SEQUENCE: 11

```
atgagatttc cttcaattttt tactgcagtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaaggggta   240
tctctcgaga aaagagaggc tgaagctgtt acttatccgg gagccattcc tctgtccctg   300
acgagcaatt acgaaacccc aagtccgaca gcaatcccgc tggagccaac accgacggct   360
accggtacag cagaattaga tgcgctgtgg aacttagtcg aagctcagta cccagttcaa   420
actgctgcag tgacaaacttt ggtgacagtg cccgatgatt ataagtttga ggcagatcca   480
ccgagttatg cattagcagg gtatgaaaca agcgagattg ccggactgaa gtttccaaag   540
gggtttaagt ttggtgttgc gggggcagcc attcaagttg aaggtgcagc aaaagccgaa   600
gggcggggcc caagtacctg ggattatctg tgtcatcact atgccagcac gcagtgtaac   660
aattatgatc ccgatattac aaccaaccat tactacctgt acccattgga ctttgcgcgc   720
ctgcaacacc taggcattaa cacttactcg ttttcaattt catggacgcg tatttatcca   780
ttgggcgcag gctatgttaa tgaagcaggg ttagcccact atgatgccgt aatccatagt   840
gccaagaagt atggtctgga accagtgggc accgttttc actgggatac gccactgtct   900
ctgatgctga atacggtgc ctggcaagat actggtgacc aaattgttaa ggactttgtt   960
acctatgcca caactgtgtt taagcgttat ggtaatgaag tcaagacgtg gtttactttc  1020
aatgaaccac gggttttctg ttcacaaaat agtggtctgc catacaatct gacgtatcca  1080
gaaggtatta acagcacctc cgctgtattt cgttgcacct acaatgttct gaaagctcat  1140
ggtcatgctg ttaaagtgta tcgggatcta gttgcctccg gaccattgc ggcaggtgaa  1200
atcggcttta aatccgatga taactaccca atcccggccc gtccagggaa cgccgatgac  1260
gaggaatcag ccaagcgtca cgaggctttt cgcattggga ttttgcgca accggtttat  1320
ggtaatggcg attatccaga tgttgttaaa gaaactgttg gagatatgct gccggccctg  1380
acggatgaag ataaaggata cattaaaggt agcggagata tttttgcgat tgacgggtat  1440
cgtaccgata tttcccatgc ggctctgaac gggatcgcga attgtattcg caaccaaagt  1500
gacccgaatt ggccagtgtg tgaagaaggg tcagatcctt ttgctcatgt ttacccatcc  1560
gggttttgcta ttggtcaatc agccgatcca ctgtcttcat ggttagtcaa ctcagccccg  1620
tttatccgcg atcaactgaa gtttctgaca caaacctacc ctgctaaggg tggtatttat  1680
ttctcggaat tggttgggc tgaagacgcc gaatatgatc gtcaactgct gtatcaaatt  1740
acctgggatg gtctgcgtac gcaataccctg acggactatc tgagccagct gctgttggct  1800
gtgcacaaag acgggattaa tctgcgaggc gcgctgacgt ggagttttgt cgataattgg  1860
gagtggggtt tagggatgca acagaaattc ggatttcagt tgttaatca atcagatccc  1920
gatctgacac gcacgtttaa actgagcgct cacgcttacg cccaatttgg gcgtaatcat  1980
ctgcaccacc accaccacca ctaa                                          2004
```

<210> SEQ ID NO 12
<211> LENGTH: 667
<212> TYPE: PRT
<213> ORGANISM: artificial
<220> FEATURE:
<223> OTHER INFORMATION: laboratory synthesized

<400> SEQUENCE: 12

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Lys Glu Glu Gly Val
65                  70                  75                  80

Ser Leu Glu Lys Arg Glu Ala Glu Ala Val Thr Tyr Pro Gly Ala Ile
                85                  90                  95

Pro Leu Ser Leu Thr Ser Asn Tyr Glu Thr Pro Ser Pro Thr Ala Ile
            100                 105                 110

Pro Leu Glu Pro Thr Pro Thr Ala Thr Gly Thr Ala Glu Leu Asp Ala
            115                 120                 125

Leu Trp Asn Leu Val Glu Ala Gln Tyr Pro Val Gln Thr Ala Ala Val
130                 135                 140

Thr Thr Leu Val Thr Val Pro Asp Asp Tyr Lys Phe Glu Ala Asp Pro
145                 150                 155                 160

Pro Ser Tyr Ala Leu Ala Gly Tyr Glu Thr Ser Glu Ile Ala Gly Leu
                165                 170                 175

Lys Phe Pro Lys Gly Phe Lys Phe Gly Val Ala Gly Ala Ala Ile Gln
            180                 185                 190

Val Glu Gly Ala Ala Lys Ala Glu Gly Arg Gly Pro Ser Thr Trp Asp
            195                 200                 205

Tyr Leu Cys His His Tyr Ala Ser Thr Gln Cys Asn Asn Tyr Asp Pro
210                 215                 220

Asp Ile Thr Thr Asn His Tyr Leu Tyr Pro Leu Asp Phe Ala Arg
225                 230                 235                 240

Leu Gln His Leu Gly Ile Asn Thr Tyr Ser Phe Ser Ile Ser Trp Thr
                245                 250                 255

Arg Ile Tyr Pro Leu Gly Ala Gly Tyr Val Asn Glu Ala Gly Leu Ala
            260                 265                 270

His Tyr Asp Ala Val Ile His Ser Ala Lys Lys Tyr Gly Leu Glu Pro
            275                 280                 285

Val Gly Thr Val Phe His Trp Asp Thr Pro Leu Ser Leu Met Leu Lys
            290                 295                 300

Tyr Gly Ala Trp Gln Asp Thr Gly Asp Gln Ile Val Lys Asp Phe Val
305                 310                 315                 320

Thr Tyr Ala Thr Thr Val Phe Lys Arg Tyr Gly Asn Glu Val Lys Thr
                325                 330                 335

Trp Phe Thr Phe Asn Glu Pro Arg Val Phe Cys Ser Gln Asn Ser Gly
            340                 345                 350

Leu Pro Tyr Asn Leu Thr Tyr Pro Glu Gly Ile Asn Ser Thr Ser Ala
            355                 360                 365

Val Phe Arg Cys Thr Tyr Asn Val Leu Lys Ala His Gly His Ala Val
            370                 375                 380

Lys Val Tyr Arg Asp Leu Val Ala Ser Gly Thr Ile Ala Ala Gly Glu
385                 390                 395                 400

Ile Gly Phe Lys Ser Asp Asp Asn Tyr Pro Ile Pro Ala Arg Pro Gly

```
                405                 410                 415
Asn Ala Asp Asp Glu Glu Ser Ala Lys Arg His Glu Ala Phe Arg Ile
            420                 425                 430

Gly Ile Phe Ala Gln Pro Val Tyr Gly Asn Gly Asp Tyr Pro Asp Val
            435                 440                 445

Val Lys Glu Thr Val Gly Asp Met Leu Pro Ala Leu Thr Asp Glu Asp
450                 455                 460

Lys Gly Tyr Ile Lys Gly Ser Gly Asp Ile Phe Ala Ile Asp Gly Tyr
465                 470                 475                 480

Arg Thr Asp Ile Ser His Ala Ala Leu Asn Gly Ile Ala Asn Cys Ile
                485                 490                 495

Arg Asn Gln Ser Asp Pro Asn Trp Pro Val Cys Glu Glu Gly Ser Asp
            500                 505                 510

Pro Phe Ala His Val Tyr Pro Ser Gly Phe Ala Ile Gly Gln Ser Ala
            515                 520                 525

Asp Pro Leu Ser Ser Trp Leu Val Asn Ser Ala Pro Phe Ile Arg Asp
530                 535                 540

Gln Leu Lys Phe Leu Thr Gln Thr Tyr Pro Ala Lys Gly Gly Ile Tyr
545                 550                 555                 560

Phe Ser Glu Phe Gly Trp Ala Glu Asp Ala Glu Tyr Asp Arg Gln Leu
                565                 570                 575

Leu Tyr Gln Ile Thr Trp Asp Gly Leu Arg Thr Gln Tyr Leu Thr Asp
            580                 585                 590

Tyr Leu Ser Gln Leu Leu Leu Ala Val His Lys Asp Gly Ile Asn Leu
            595                 600                 605

Arg Gly Ala Leu Thr Trp Ser Phe Val Asp Asn Trp Glu Trp Gly Leu
610                 615                 620

Gly Met Gln Gln Lys Phe Gly Phe Gln Phe Val Asn Gln Ser Asp Pro
625                 630                 635                 640

Asp Leu Thr Arg Thr Phe Lys Leu Ser Ala His Ala Tyr Ala Gln Phe
                645                 650                 655

Gly Arg Asn His Leu His His His His His His
            660                 665

<210> SEQ ID NO 13
<211> LENGTH: 1986
<212> TYPE: DNA
<213> ORGANISM: artificial
<220> FEATURE:
<223> OTHER INFORMATION: laboratory synthesized

<400> SEQUENCE: 13
atgagatttc cttcaattt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggggta    240 tctctcgaga aaagagaggc tgaagctgtt acttatccgg gagccattcc tctgtccctg     300
acgagcaatt acgaaacccc aagtccgaca gcaatcccgc tggagccaac accgacggct     360
accggtacag cagaattaga tgcgctgtgg aacttagtcg aagctcagta cccagttcaa     420
actgctgcag tgacaacttt ggtgacagtg cccgatgatt ataagtttga ggcagatcca     480
ccgagttatg cattagcagg gtatgaaaca agcgagattc cggactgaa gtttccaaag     540 gggtttaagt tggtgtttgc gggggcagcc attcaagttg aaggtgcagc aaaagccgaa     600
```

```
gggcggggcc caagtacctg ggattatctg tgtcatcact atgccagcac gcagtgtaac    660
aattatgatc ccgatattac aaccaaccat tactacctgt acccattgga ctttgcgcgc    720
ctgcaacacc taggcattaa cacttactcg ttttcaattt catggacgcg tatttatcca    780
ttgggcgcag gctatgttaa tgaagcaggg ttagcccact atgatgccgt aatccatagt    840
gccaagaagt atggtctgga accagtgggc accgtttttc actgggatac gccactgtct    900
ctgatgctga atacggtgc ctggcaagat actggtgacc aaattgttaa ggactttgtt     960
acctatgcca caactgtgtt taagcgttat ggtaatgaag tcaagacgtg gtttactttc    1020
aatgaaccac gggttttctg ttcacaaaat agtggtctgc catacaatct gacgtatcca    1080
gaaggtatta acagcacctc cgctgtattt cgttgcacct acaatgttct gaaagctcat    1140
ggtcatgctg ttaaagtgta tcgggatcta gttgcctccg ggaccattgc ggcaggtgaa    1200
atcggcttta atccgatga taactaccca atcccggccc gtccagggaa cgccgatgac    1260
gaggaatcag ccaagcgtca cgaggctttt cgcattggga ttttgcgca accggtttat     1320 ggtaatggcg attatccaga tgttgttaaa gaaactgttg agatatgct gccggccctg      1380 acggatgaag ataaaggata cattaaaggt agcggagata ttttgcgat tgacgggtat     1440 cgtaccgata tttcccatgc ggctctgaac gggatcgcga attgtattcg caaccaaagt    1500
gacccgaatt ggccagtgtg tgaagaaggg tcagatcctt ttgctcatgt ttacccatcc    1560
gggtttgcta ttggtcaatc agccgatcca ctgtcttcat ggttagtcaa ctcagccccg    1620
tttatccgcg atcaactgaa gtttctgaca caaacctacc ctgctaaggg tggtatttat    1680
ttctcggaat ttggttgggc tgaagacgcc gaatatgatc gtcaactgct gtatcaaatt    1740
acctgggatg gtctgcgtac gcaataccctg acggactatc tgagccagct gctgttggct    1800
gtgcacaaag acgggattaa tctgcgaggc gcgctgacgt ggagttttgt cgataattgg    1860 gagtgggggtt tagggatgca acagaaattc ggatttcagt ttgttaatca atcagatccc    1920
gatctgacac gcacgtttaa actgagcgct cacgcttacg cccaatttgg gcgtaatcat    1980
ctgtaa                                                             1986
```

<210> SEQ ID NO 14
<211> LENGTH: 661
<212> TYPE: PRT
<213> ORGANISM: artificial
<220> FEATURE:
<223> OTHER INFORMATION: laboratory synthesized

<400> SEQUENCE: 14

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Val Thr Tyr Pro Gly Ala Ile
                85                  90                  95

Pro Leu Ser Leu Thr Ser Asn Tyr Glu Thr Pro Ser Pro Thr Ala Ile
            100                 105                 110

```
Pro Leu Glu Pro Thr Pro Thr Ala Thr Gly Thr Ala Glu Leu Asp Ala
        115                 120                 125
Leu Trp Asn Leu Val Glu Ala Gln Tyr Pro Val Gln Thr Ala Ala Val
    130                 135                 140
Thr Thr Leu Val Thr Val Pro Asp Asp Tyr Lys Phe Glu Ala Asp Pro
145                 150                 155                 160
Pro Ser Tyr Ala Leu Ala Gly Tyr Glu Thr Ser Glu Ile Ala Gly Leu
                165                 170                 175
Lys Phe Pro Lys Gly Phe Lys Phe Gly Val Ala Gly Ala Ala Ile Gln
            180                 185                 190
Val Glu Gly Ala Ala Lys Ala Glu Gly Arg Gly Pro Ser Thr Trp Asp
        195                 200                 205
Tyr Leu Cys His His Tyr Ala Ser Thr Gln Cys Asn Asn Tyr Asp Pro
    210                 215                 220
Asp Ile Thr Thr Asn His Tyr Leu Tyr Pro Leu Asp Phe Ala Arg
225                 230                 235                 240
Leu Gln His Leu Gly Ile Asn Thr Tyr Ser Phe Ser Ile Ser Trp Thr
            245                 250                 255
Arg Ile Tyr Pro Leu Gly Ala Gly Tyr Val Asn Glu Ala Gly Leu Ala
        260                 265                 270
His Tyr Asp Ala Val Ile His Ser Ala Lys Lys Tyr Gly Leu Glu Pro
    275                 280                 285
Val Gly Thr Val Phe His Trp Asp Thr Pro Leu Ser Leu Met Leu Lys
    290                 295                 300
Tyr Gly Ala Trp Gln Asp Thr Gly Asp Gln Ile Val Lys Asp Phe Val
305                 310                 315                 320
Thr Tyr Ala Thr Thr Val Phe Lys Arg Tyr Gly Asn Glu Val Lys Thr
            325                 330                 335
Trp Phe Thr Phe Asn Glu Pro Arg Val Phe Cys Ser Gln Asn Ser Gly
            340                 345                 350
Leu Pro Tyr Asn Leu Thr Tyr Pro Glu Gly Ile Asn Ser Thr Ser Ala
        355                 360                 365
Val Phe Arg Cys Thr Tyr Asn Val Leu Lys Ala His Gly His Ala Val
        370                 375                 380
Lys Val Tyr Arg Asp Leu Val Ala Ser Gly Thr Ile Ala Ala Gly Glu
385                 390                 395                 400
Ile Gly Phe Lys Ser Asp Asp Asn Tyr Pro Ile Pro Ala Arg Pro Gly
            405                 410                 415
Asn Ala Asp Asp Glu Glu Ser Ala Lys Arg His Glu Ala Phe Arg Ile
            420                 425                 430
Gly Ile Phe Ala Gln Pro Val Tyr Gly Asn Gly Asp Tyr Pro Asp Val
        435                 440                 445
Val Lys Glu Thr Val Gly Asp Met Leu Pro Ala Leu Thr Asp Glu Asp
    450                 455                 460
Lys Gly Tyr Ile Lys Gly Ser Gly Asp Ile Phe Ala Ile Asp Gly Tyr
465                 470                 475                 480
Arg Thr Asp Ile Ser His Ala Ala Leu Asn Gly Ile Ala Asn Cys Ile
            485                 490                 495
Arg Asn Gln Ser Asp Pro Asn Trp Pro Val Cys Glu Glu Gly Ser Asp
            500                 505                 510
Pro Phe Ala His Val Tyr Pro Ser Gly Phe Ala Ile Gly Gln Ser Ala
        515                 520                 525
```

Asp Pro Leu Ser Ser Trp Leu Val Asn Ser Ala Pro Phe Ile Arg Asp
    530                 535                 540

Gln Leu Lys Phe Leu Thr Gln Thr Tyr Pro Ala Lys Gly Gly Ile Tyr
545                 550                 555                 560

Phe Ser Glu Phe Gly Trp Ala Glu Asp Ala Glu Tyr Asp Arg Gln Leu
                565                 570                 575

Leu Tyr Gln Ile Thr Trp Asp Gly Leu Arg Thr Gln Tyr Leu Thr Asp
            580                 585                 590

Tyr Leu Ser Gln Leu Leu Ala Val His Lys Asp Gly Ile Asn Leu
        595                 600                 605

Arg Gly Ala Leu Thr Trp Ser Phe Val Asp Asn Trp Glu Trp Gly Leu
    610                 615                 620

Gly Met Gln Gln Lys Phe Gly Phe Gln Phe Val Asn Gln Ser Asp Pro
625                 630                 635                 640

Asp Leu Thr Arg Thr Phe Lys Leu Ser Ala His Ala Tyr Ala Gln Phe
                645                 650                 655

Gly Arg Asn His Leu
            660

<210> SEQ ID NO 15
<211> LENGTH: 1803
<212> TYPE: DNA
<213> ORGANISM: artificial
<220> FEATURE:
<223> OTHER INFORMATION: laboratory synthesized

<400> SEQUENCE: 15
atgatgctgc atgctgcact gctagtagcg ctgccatgtg ttgttttggc gcgcccggcc      60
ggagcggtta cttatccggg agccattcct ctgtccctga cgagcaatta cgaaaccccca    120 agtccgacag caatcccgct ggagccaaca ccgacggcta ccggtacagc agaattagat    180
gcgctgtgga acttagtcga agctcagtac ccagttcaaa ctgctgcagt gacaactttg    240
gtgacagtgc ccgatgatta aagtttgag gcagatccac cgagttatgc attagcaggg     300
tatgaaacaa gcgagattgc cggactgaag tttccaaagg ggtttaagtt tggtgttgcg    360
ggggcagcca ttcaagttga aggtgcagca aaagccgaag gcgggggccc aagtacctgg    420
gattatctgt gtcatcacta tgccagcacg cagtgtaaca attatgatcc cgatattaca    480
accaaccatt actacctgta cccattggac tttgcgcgcc tgcaacacct aggcattaac    540
acttactcgt tttcaatttc atggacgcgt atttatccat gggcgcagg ctatgttaat     600 gaagcagggt tagcccacta tgatgccgta atccatagtg ccaagaagta tggtctggaa    660
ccagtgggca ccgttttttca ctgggatacg ccactgtctc tgatgctgaa atacggtgcc    720
tggcaagata ctggtgacca aattgttaag gactttgtta cctatgccac aactgtgttt    780
aagcgttatg gtaatgaagt caagacgtgg tttactttca tgaaccacg ggttttctgt     840 tcacaaaata gtggtctgcc atacaatctg acgtatccag aaggtattaa cagcacctcc    900
gctgtatttc gttgcaccta caatgttctg aaagctcatg gtcatgctgt taaagtgtat    960
cgggatctag ttgcctccgg gaccattgcg gcaggtgaaa tcggctttaa atccgatgat   1020
aactacccaa tcccggcccg tccagggaac gccgatgacg aggaatcagc caagcgtcac   1080
gaggcttttc gcattgggat ttttgcgcaa ccggtttatg gtaatggcga ttatccagat   1140
gttgttaaag aaactgttgg agatatgctg ccggccctga cggatgaaga taaaggatac   1200
attaaaggta gcggagatat ttttgcgatt gacgggtatc gtaccgatat ttcccatgcg   1260

```
gctctgaacg ggatcgcgaa ttgtattcgc aaccaaagtg acccgaattg gccagtgtgt    1320
gaagaagggt cagatccttt tgctcatgtt tacccatccg ggtttgctat tggtcaatca    1380
gccgatccac tgtcttcatg gttagtcaac tcagccccgt ttatccgcga tcaactgaag    1440
tttctgacac aaacctaccc tgctaagggt ggtatttatt tctcggaatt tggttgggct    1500
gaagacgccg aatatgatcg tcaactgctg tatcaaatta cctgggatgg tctgcgtacg    1560 caataccctga cggactatct gagccagctg ctgttggctg tgcacaaaga cgggattaat    1620
ctgcgaggcg cgctgacgtg gagttttgtc gataattggg agtggggttt agggatgcaa    1680
cagaaattcg gatttcagtt tgttaatcaa tcagatcccg atctgacacg cacgtttaaa    1740
ctgagcgctc acgcttacgc ccaatttggg cgtaatcatc tgcaccacca ccaccaccac    1800
taa                                                                   1803
```

```
<210> SEQ ID NO 16
<211> LENGTH: 600
<212> TYPE: PRT
<213> ORGANISM: artificial
<220> FEATURE:
<223> OTHER INFORMATION: laboratory synthesized

<400> SEQUENCE: 16

Met Met Leu His Ala Ala Leu Leu Val Ala Leu Pro Cys Val Val Leu
1               5                   10                  15

Ala Arg Pro Ala Gly Ala Val Thr Tyr Pro Gly Ala Ile Pro Leu Ser
            20                  25                  30

Leu Thr Ser Asn Tyr Glu Thr Pro Ser Pro Thr Ala Ile Pro Leu Glu
        35                  40                  45

Pro Thr Pro Thr Ala Thr Gly Thr Ala Glu Leu Asp Ala Leu Trp Asn
    50                  55                  60

Leu Val Glu Ala Gln Tyr Pro Val Gln Thr Ala Val Thr Thr Leu
65                  70                  75                  80

Val Thr Val Pro Asp Asp Tyr Lys Phe Glu Ala Asp Pro Pro Ser Tyr
                85                  90                  95

Ala Leu Ala Gly Tyr Glu Thr Ser Glu Ile Ala Gly Leu Lys Phe Pro
            100                 105                 110

Lys Gly Phe Lys Phe Gly Val Ala Gly Ala Ala Ile Gln Val Glu Gly
        115                 120                 125

Ala Ala Lys Ala Glu Gly Arg Gly Pro Ser Thr Trp Asp Tyr Leu Cys
    130                 135                 140

His His Tyr Ala Ser Thr Gln Cys Asn Asn Tyr Asp Pro Asp Ile Thr
145                 150                 155                 160

Thr Asn His Tyr Tyr Leu Tyr Pro Leu Asp Phe Ala Arg Leu Gln His
                165                 170                 175

Leu Gly Ile Asn Thr Tyr Ser Phe Ser Ile Ser Trp Thr Arg Ile Tyr
            180                 185                 190

Pro Leu Gly Ala Gly Tyr Val Asn Glu Ala Gly Leu Ala His Tyr Asp
        195                 200                 205

Ala Val Ile His Ser Ala Lys Lys Tyr Gly Leu Glu Pro Val Gly Thr
    210                 215                 220

Val Phe His Trp Asp Thr Pro Leu Ser Leu Met Leu Lys Tyr Gly Ala
225                 230                 235                 240

Trp Gln Asp Thr Gly Asp Gln Ile Val Lys Asp Phe Val Thr Tyr Ala
                245                 250                 255

Thr Thr Val Phe Lys Arg Tyr Gly Asn Glu Val Lys Thr Trp Phe Thr
```

```
                  260                 265                 270
Phe Asn Glu Pro Arg Val Phe Cys Ser Gln Asn Ser Gly Leu Pro Tyr
            275                 280                 285
Asn Leu Thr Tyr Pro Glu Gly Ile Asn Ser Thr Ser Ala Val Phe Arg
            290                 295                 300
Cys Thr Tyr Asn Val Leu Lys Ala His Gly His Ala Val Lys Val Tyr
305                 310                 315                 320
Arg Asp Leu Val Ala Ser Gly Thr Ile Ala Ala Gly Glu Ile Gly Phe
                        325                 330                 335
Lys Ser Asp Asp Asn Tyr Pro Ile Pro Ala Arg Pro Gly Asn Ala Asp
                        340                 345                 350
Asp Glu Glu Ser Ala Lys Arg His Glu Ala Phe Arg Ile Gly Ile Phe
                        355                 360                 365
Ala Gln Pro Val Tyr Gly Asn Gly Asp Tyr Pro Asp Val Val Lys Glu
                        370                 375                 380
Thr Val Gly Asp Met Leu Pro Ala Leu Thr Asp Glu Asp Lys Gly Tyr
385                 390                 395                 400
Ile Lys Gly Ser Gly Asp Ile Phe Ala Ile Asp Gly Tyr Arg Thr Asp
                        405                 410                 415
Ile Ser His Ala Ala Leu Asn Gly Ile Ala Asn Cys Ile Arg Asn Gln
                        420                 425                 430
Ser Asp Pro Asn Trp Pro Val Cys Glu Glu Gly Ser Asp Pro Phe Ala
                        435                 440                 445
His Val Tyr Pro Ser Gly Phe Ala Ile Gly Gln Ser Ala Asp Pro Leu
                        450                 455                 460
Ser Ser Trp Leu Val Asn Ser Ala Pro Phe Ile Arg Asp Gln Leu Lys
465                 470                 475                 480
Phe Leu Thr Gln Thr Tyr Pro Ala Lys Gly Gly Ile Tyr Phe Ser Glu
                        485                 490                 495
Phe Gly Trp Ala Glu Asp Ala Glu Tyr Asp Arg Gln Leu Leu Tyr Gln
                        500                 505                 510
Ile Thr Trp Asp Gly Leu Arg Thr Gln Tyr Leu Thr Asp Tyr Leu Ser
                        515                 520                 525
Gln Leu Leu Leu Ala Val His Lys Asp Gly Ile Asn Leu Arg Gly Ala
            530                 535                 540
Leu Thr Trp Ser Phe Val Asp Asn Trp Glu Trp Gly Leu Gly Met Gln
545                 550                 555                 560
Gln Lys Phe Gly Phe Gln Phe Val Asn Gln Ser Asp Pro Asp Leu Thr
                        565                 570                 575
Arg Thr Phe Lys Leu Ser Ala His Ala Tyr Ala Gln Phe Gly Arg Asn
                        580                 585                 590
His Leu His His His His His
            595                 600

<210> SEQ ID NO 17
<211> LENGTH: 1740
<212> TYPE: DNA
<213> ORGANISM: artificial
<220> FEATURE:
<223> OTHER INFORMATION: laboratory synthesized

<400> SEQUENCE: 17
atggttactt atccgggagc cattcctctg tccctgacga gcaattacga aaccccaagt      60
ccgacagcaa tcccgctgga gccaacaccg acggctaccg gtacagcaga attagatgcg     120
```

```
ctgtggaact tagtcgaagc tcagtaccca gttcaaactg ctgcagtgac aactttggtg    180
acagtgcccg atgattataa gtttgaggca gatccaccga gttatgcatt agcagggtat    240
gaaacaagcg agattgccgg actgaagttt ccaaaggggt ttaagtttgg tgttgcgggg    300
gcagccattc aagttgaagg tgcagcaaaa gccgaagggc ggggcccaag tacctgggat    360
tatctgtgtc atcactatgc cagcacgcag tgtaacaatt atgatcccga tattacaacc    420
aaccattact acctgtaccc attggacttt gcgcgcctgc aacacctagg cattaacact    480
tactcgtttt caatttcatg gacgcgtatt tatccattgg gcgcaggcta tgttaatgaa    540
gcagggttag cccactatga tgccgtaatc catagtgcca agaagtatgg tctggaacca    600
gtgggcaccg ttttcactg ggatacgcca ctgtctctga tgctgaaata cggtgcctgg    660
caagatactg gtgaccaaat tgttaaggac tttgttacct atgccacaac tgtgtttaag    720
cgttatggta atgaagtcaa gacgtggttt actttcaatg aaccacgggt tttctgttca    780
caaaatagtg gtctgccata caatctgacg tatccagaag gtattaacag cacctccgct    840
gtatttcgtt gcacctacaa tgttctgaaa gctcatggtc atgctgttaa agtgtatcgg    900
gatctagttg cctccgggac cattgcggca ggtgaaatcg ctttaaatc gatgataac    960
tacccaatcc cggcccgtcc agggaacgcc gatgacgagg aatcagccaa gcgtcacgag   1020
gcttttcgca ttgggatttt tgcgcaaccg gtttatggta atggcgatta tccagatgtt   1080
gttaaagaaa ctgttggaga tatgctgccg gccctgacgg atgaagataa aggatacatt   1140
aaaggtagcg gagatatttt tgcgattgac gggtatcgta ccgatatttc ccatgcggct   1200
ctgaacggga tcgcgaattg tattcgcaac caaagtgacc cgaattggcc agtgtgtgaa   1260
gaagggtcag atccttttgc tcatgtttac ccatccgggt ttgctattgg tcaatcagcc   1320
gatccactgt cttcatggtt agtcaactca gccccgttta ccgcgatca actgaagttt   1380
ctgacacaaa cctaccctgc taagggtggt attatttct cggaatttgg ttgggctgaa   1440
gacgccgaat atgatcgtca actgctgtat caaattaccct gggatggtct gcgtacgcaa   1500
tacctgacgg actatctgag ccagctgctg ttggctgtgc acaaagacgg gattaatctg   1560
cgaggcgcgc tgacgtggag ttttgtcgat aattgggagt ggggtttagg gatgcaacag   1620
aaattcggat ttcagtttgt taatcaatca gatcccgatc tgacacgcac gtttaaactg   1680
agcgctcacg cttacgccca atttgggcgt aatcatctgc accaccacca ccaccactaa   1740
```

<210> SEQ ID NO 18
<211> LENGTH: 579
<212> TYPE: PRT
<213> ORGANISM: artificial
<220> FEATURE:
<223> OTHER INFORMATION: laboratory synthesized

<400> SEQUENCE: 18

```
Met Val Thr Tyr Pro Gly Ala Ile Pro Leu Ser Leu Thr Ser Asn Tyr
1               5                   10                  15

Glu Thr Pro Ser Pro Thr Ala Ile Pro Leu Glu Pro Thr Pro Thr Ala
            20                  25                  30

Thr Gly Thr Ala Glu Leu Asp Ala Leu Trp Asn Leu Val Glu Ala Gln
        35                  40                  45

Tyr Pro Val Gln Thr Ala Ala Val Thr Thr Leu Val Thr Val Pro Asp
    50                  55                  60

Asp Tyr Lys Phe Glu Ala Asp Pro Pro Ser Tyr Ala Leu Ala Gly Tyr
65                  70                  75                  80
```

-continued

Glu Thr Ser Glu Ile Ala Gly Leu Lys Phe Pro Lys Gly Phe Lys Phe
            85                  90                  95
Gly Val Ala Gly Ala Ala Ile Gln Val Glu Gly Ala Ala Lys Ala Glu
            100                 105                 110
Gly Arg Gly Pro Ser Thr Trp Asp Tyr Leu Cys His His Tyr Ala Ser
        115                 120                 125
Thr Gln Cys Asn Asn Tyr Asp Pro Asp Ile Thr Thr Asn His Tyr Tyr
    130                 135                 140
Leu Tyr Pro Leu Asp Phe Ala Arg Leu Gln His Leu Gly Ile Asn Thr
145                 150                 155                 160
Tyr Ser Phe Ser Ile Ser Trp Thr Arg Ile Tyr Pro Leu Gly Ala Gly
                165                 170                 175
Tyr Val Asn Glu Ala Gly Leu Ala His Tyr Asp Ala Val Ile His Ser
            180                 185                 190
Ala Lys Lys Tyr Gly Leu Glu Pro Val Gly Thr Val Phe His Trp Asp
        195                 200                 205
Thr Pro Leu Ser Leu Met Leu Lys Tyr Gly Ala Trp Gln Asp Thr Gly
    210                 215                 220
Asp Gln Ile Val Lys Asp Phe Val Thr Tyr Ala Thr Thr Val Phe Lys
225                 230                 235                 240
Arg Tyr Gly Asn Glu Val Lys Thr Trp Phe Thr Phe Asn Glu Pro Arg
                245                 250                 255
Val Phe Cys Ser Gln Asn Ser Gly Leu Pro Tyr Asn Leu Thr Tyr Pro
            260                 265                 270
Glu Gly Ile Asn Ser Thr Ser Ala Val Phe Arg Cys Thr Tyr Asn Val
        275                 280                 285
Leu Lys Ala His Gly His Ala Val Lys Val Tyr Arg Asp Leu Val Ala
    290                 295                 300
Ser Gly Thr Ile Ala Ala Gly Glu Ile Gly Phe Lys Ser Asp Asp Asn
305                 310                 315                 320
Tyr Pro Ile Pro Ala Arg Pro Gly Asn Ala Asp Asp Glu Glu Ser Ala
                325                 330                 335
Lys Arg His Glu Ala Phe Arg Ile Gly Ile Phe Ala Gln Pro Val Tyr
            340                 345                 350
Gly Asn Gly Asp Tyr Pro Asp Val Val Lys Glu Thr Val Gly Asp Met
        355                 360                 365
Leu Pro Ala Leu Thr Asp Glu Asp Lys Gly Tyr Ile Lys Gly Ser Gly
    370                 375                 380
Asp Ile Phe Ala Ile Asp Gly Tyr Arg Thr Asp Ile Ser His Ala Ala
385                 390                 395                 400
Leu Asn Gly Ile Ala Asn Cys Ile Arg Asn Gln Ser Asp Pro Asn Trp
                405                 410                 415
Pro Val Cys Glu Glu Gly Ser Asp Pro Phe Ala His Val Tyr Pro Ser
            420                 425                 430
Gly Phe Ala Ile Gly Gln Ser Ala Asp Pro Leu Ser Ser Trp Leu Val
        435                 440                 445
Asn Ser Ala Pro Phe Ile Arg Asp Gln Leu Lys Phe Leu Thr Gln Thr
    450                 455                 460
Tyr Pro Ala Lys Gly Ile Tyr Phe Ser Glu Phe Gly Trp Ala Glu
465                 470                 475                 480
Asp Ala Glu Tyr Asp Arg Gln Leu Leu Tyr Gln Ile Thr Trp Asp Gly
                485                 490                 495
Leu Arg Thr Gln Tyr Leu Thr Asp Tyr Leu Ser Gln Leu Leu Leu Ala

```
                500             505             510
Val His Lys Asp Gly Ile Asn Leu Arg Gly Ala Leu Thr Trp Ser Phe
            515             520             525

Val Asp Asn Trp Glu Trp Gly Leu Gly Met Gln Gln Lys Phe Gly Phe
        530             535             540

Gln Phe Val Asn Gln Ser Asp Pro Asp Leu Thr Arg Thr Phe Lys Leu
545             550             555             560

Ser Ala His Ala Tyr Ala Gln Phe Gly Arg Asn His Leu His His His
            565             570             575

His His His
```

<210> SEQ ID NO 19
<211> LENGTH: 1755
<212> TYPE: DNA
<213> ORGANISM: artificial
<220> FEATURE:
<223> OTHER INFORMATION: laboratory synthesized

<400> SEQUENCE: 19

```
atgagatttc cttcaattttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattc tgctaaagaa agaaggggta     240
tctctcgaga aaagagaggc tgaagcttac gtagaattca tgtttccaaa ggggtttaag     300
tttggtgttg cggggggcagc cattcaagtt gaaggtgcag caaaagccga agggcggggc     360
ccaagtacct gggattatct gtgtcatcac tatgccagca cgcagtgtaa caattatgat     420
cccgatatta caaccaacca ttactacctg tacccattgg actttgcgcg cctgcaacac     480
ctaggcatta acacttactc gttttcaatt tcatggacgc gtatttatcc attgggcgca     540
ggctatgtta tgaagcagg gttagcccac tatgatgccg taatccatag tgccaagaag     600
tatggtctgg aaccagtggg caccgttttt cactgggata cgccactgtc tctgatgctg     660
aaatacggtg cctggcaaga tactggtgac caaattgtta aggactttgt tacctatgcc     720
acaactgtgt ttaagcgtta tggtaatgaa gtcaagacgt ggtttacttt caatgaacca     780
cgggttttct gttcacaaaa tagtggtctg ccatacaatc tgacgtatcc agaaggtatt     840
aacagcacct ccgctgtatt tcgttgcacc tacaatgttc tgaaagctca tggtcatgct     900
gttaaagtgt atcgggatct agttgcctcc gggaccattg cggcaggtga atcggctttt     960
aaatccgatg ataactaccc aatcccggcc cgtccaggga cgccgatga cgaggaatca    1020
gccaagcgtc acgaggcttt tcgcattggg atttttgcgc aaccggttta tggtaatggc    1080
gattatccag atgttgttaa agaaactgtt ggagatatgc tgccggccct gacggatgaa    1140
gataaaggat acattaaagg tagcggagat attttttgcga ttgacgggta tcgtaccgat    1200
atttcccatg cggctctgaa cgggatcgcg aattgtattc gcaaccaaag tgacccgaat    1260
tggccagtgt gtgaagaagg gtcagatcct tttgctcatg tttacccatc cgggtttgct    1320
attggtcaat cagccgatcc actgtcttca tggttagtca actcagcccc gtttatccgc    1380
gatcaactga gtttctgac acaaacctac cctgctaagg gtggtattta tttctcggaa    1440
tttggttggg ctgaagacgc cgaatatgat cgtcaactgc tgtatcaaat tacctgggat    1500
ggtctgcgta cgcaatacct gacggactat ctgagccagc tgctgttggc tgtgcacaaa    1560
gacgggatta atctgcgagg cgcgctgacg tggagttttg tcgataattg ggagtggggt    1620
```

-continued

```
ttagggatgc aacagaaatt cggatttcag tttgttaatc aatcagatcc cgatctgaca    1680
cgcacgttta aactgagcgc tcacgcttac gcccaatttg ggcgtaatca tctgcaccac    1740
caccaccacc actaa                                                    1755
```

<210> SEQ ID NO 20
<211> LENGTH: 584
<212> TYPE: PRT
<213> ORGANISM: artificial
<220> FEATURE:
<223> OTHER INFORMATION: laboratory synthesized

<400> SEQUENCE: 20

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Tyr Val Glu Phe Met Phe Pro
                85                  90                  95

Lys Gly Phe Lys Phe Gly Val Ala Gly Ala Ala Ile Gln Val Glu Gly
            100                 105                 110

Ala Ala Lys Ala Glu Gly Arg Gly Pro Ser Thr Trp Asp Tyr Leu Cys
        115                 120                 125

His His Tyr Ala Ser Thr Gln Cys Asn Asn Tyr Asp Pro Asp Ile Thr
    130                 135                 140

Thr Asn His Tyr Leu Tyr Pro Leu Asp Phe Ala Arg Leu Gln His
145                 150                 155                 160

Leu Gly Ile Asn Thr Tyr Ser Phe Ser Ile Ser Trp Thr Arg Ile Tyr
                165                 170                 175

Pro Leu Gly Ala Gly Tyr Val Asn Glu Ala Gly Leu Ala His Tyr Asp
            180                 185                 190

Ala Val Ile His Ser Ala Lys Lys Tyr Gly Leu Glu Pro Val Gly Thr
        195                 200                 205

Val Phe His Trp Asp Thr Pro Leu Ser Leu Met Leu Lys Tyr Gly Ala
    210                 215                 220

Trp Gln Asp Thr Gly Asp Gln Ile Val Lys Asp Phe Val Thr Tyr Ala
225                 230                 235                 240

Thr Thr Val Phe Lys Arg Tyr Gly Asn Glu Val Lys Thr Trp Phe Thr
                245                 250                 255

Phe Asn Glu Pro Arg Val Phe Cys Ser Gln Asn Ser Gly Leu Pro Tyr
            260                 265                 270

Asn Leu Thr Tyr Pro Glu Gly Ile Asn Ser Thr Ser Ala Val Phe Arg
        275                 280                 285

Cys Thr Tyr Asn Val Leu Lys Ala His Gly His Ala Val Lys Val Tyr
    290                 295                 300

Arg Asp Leu Val Ala Ser Gly Thr Ile Ala Ala Gly Glu Ile Gly Phe
305                 310                 315                 320

Lys Ser Asp Asp Asn Tyr Pro Ile Pro Ala Arg Pro Gly Asn Ala Asp
                325                 330                 335
```

```
Asp Glu Glu Ser Ala Lys Arg His Glu Ala Phe Arg Ile Gly Ile Phe
                340                 345                 350

Ala Gln Pro Val Tyr Gly Asn Gly Asp Tyr Pro Asp Val Lys Glu
            355                 360                 365

Thr Val Gly Asp Met Leu Pro Ala Leu Thr Asp Glu Asp Lys Gly Tyr
        370                 375                 380

Ile Lys Gly Ser Gly Asp Ile Phe Ala Ile Asp Gly Tyr Arg Thr Asp
385                 390                 395                 400

Ile Ser His Ala Ala Leu Asn Gly Ile Ala Asn Cys Ile Arg Asn Gln
                405                 410                 415

Ser Asp Pro Asn Trp Pro Val Cys Glu Glu Gly Ser Asp Pro Phe Ala
            420                 425                 430

His Val Tyr Pro Ser Gly Phe Ala Ile Gly Gln Ser Ala Asp Pro Leu
        435                 440                 445

Ser Ser Trp Leu Val Asn Ser Ala Pro Phe Ile Arg Asp Gln Leu Lys
450                 455                 460

Phe Leu Thr Gln Thr Tyr Pro Ala Lys Gly Ile Tyr Phe Ser Glu
465                 470                 475                 480

Phe Gly Trp Ala Glu Asp Ala Glu Tyr Asp Arg Gln Leu Leu Tyr Gln
                485                 490                 495

Ile Thr Trp Asp Gly Leu Arg Thr Gln Tyr Leu Thr Asp Tyr Leu Ser
            500                 505                 510

Gln Leu Leu Leu Ala Val His Lys Asp Gly Ile Asn Leu Arg Gly Ala
        515                 520                 525

Leu Thr Trp Ser Phe Val Asp Asn Trp Glu Trp Gly Leu Gly Met Gln
530                 535                 540

Gln Lys Phe Gly Phe Gln Phe Val Asn Gln Ser Asp Pro Asp Leu Thr
545                 550                 555                 560

Arg Thr Phe Lys Leu Ser Ala His Ala Tyr Ala Gln Phe Gly Arg Asn
                565                 570                 575

His Leu His His His His His
            580

<210> SEQ ID NO 21
<211> LENGTH: 82
<212> TYPE: DNA
<213> ORGANISM: artificial
<220> FEATURE:
<223> OTHER INFORMATION: laboratory synthesized

<400> SEQUENCE: 21
ccgctcgaga aaagagaggc tgaagctcac caccaccacc accacgaaaa cctgtatttt      60
cagatgatgc tgcatgctgc ac                                              82

<210> SEQ ID NO 22
<211> LENGTH: 42
<212> TYPE: DNA
<213> ORGANISM: artificial
<220> FEATURE:
<223> OTHER INFORMATION: laboratory synthesized

<400> SEQUENCE: 22
aaggaaaaaa gcggccgctt acagatgatt acgcccaaat tg                        42

<210> SEQ ID NO 23
<211> LENGTH: 24
<212> TYPE: DNA
```

```
<213> ORGANISM: artificial
<220> FEATURE:
<223> OTHER INFORMATION: laboratory synthesized

<400> SEQUENCE: 23
atcactatgc cagcacgcag tgta                                          24

<210> SEQ ID NO 24
<211> LENGTH: 24
<212> TYPE: DNA
<213> ORGANISM: artificial
<220> FEATURE:
<223> OTHER INFORMATION: laboratory synthesized

<400> SEQUENCE: 24
tttaaagccg atttcacctg ccgc                                          24

<210> SEQ ID NO 25
<211> LENGTH: 21
<212> TYPE: DNA
<213> ORGANISM: artificial
<220> FEATURE:
<223> OTHER INFORMATION: laboratory synthesized

<400> SEQUENCE: 25
gactggttcc aattgacaag c                                             21

<210> SEQ ID NO 26
<211> LENGTH: 21
<212> TYPE: DNA
<213> ORGANISM: artificial
<220> FEATURE:
<223> OTHER INFORMATION: laboratory synthesized

<400> SEQUENCE: 26
gcaaatggca ttctgacatc c                                             21

<210> SEQ ID NO 27
<211> LENGTH: 21
<212> TYPE: DNA
<213> ORGANISM: artificial
<220> FEATURE:
<223> OTHER INFORMATION: laboratory synthesized

<400> SEQUENCE: 27
tactattgcc agcattgctg c                                             21
```